(12) United States Patent
Kahne et al.

(10) Patent No.: US 9,273,084 B2
(45) Date of Patent: Mar. 1, 2016

(54) MOENOMYCIN ANALOGS, METHODS OF SYNTHESIS, AND USES THEREOF

(71) Applicant: President and Fellows of Harvard College, Cambridge, MA (US)

(72) Inventors: Daniel Evan Kahne, Brookline, MA (US); Suzanne Walker Kahne, Brookline, MA (US); Hirokazu Tsukamoto, Sendai (JP)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 14/390,811

(22) PCT Filed: Apr. 5, 2013

(86) PCT No.: PCT/US2013/035416
§ 371 (c)(1),
(2) Date: Oct. 6, 2014

(87) PCT Pub. No.: WO2013/152277
PCT Pub. Date: Oct. 10, 2013

(65) Prior Publication Data
US 2015/0119354 A1    Apr. 30, 2015

Related U.S. Application Data

(60) Provisional application No. 61/621,161, filed on Apr. 6, 2012.

(51) Int. Cl.
*C07H 5/06* (2006.01)
*C07H 13/12* (2006.01)
*C07F 9/6558* (2006.01)

(52) U.S. Cl.
CPC ............ *C07H 13/12* (2013.01); *C07F 9/65586* (2013.01); *C07H 5/06* (2013.01)

(58) Field of Classification Search
None
See application file for complete search history.

(56) References Cited

U.S. PATENT DOCUMENTS 3,949,070 A    4/1976   Arai et al.
3,992,263 A    11/1976  Dietrich et al.
(Continued)

FOREIGN PATENT DOCUMENTS

EP    0 652 205 A2    5/1995
EP    1 069 130 A1    1/2001
(Continued)

OTHER PUBLICATIONS

Wolff, Manfred E., "Burger's Medicinal Chemistry, 5ed, Part I", John Wiley & Sons, 1995, pp. 975-977.*

Banker, G.S. et al, "Modern Pharmaceutics, 3ed.", Marcel Dekker, New York, 1996, p. 596.*
Riedel et al., Tetrahedron, vol. 55, 1999, pp. 1921-1936.*
Extended European Search Report for EP 08834841.2, mailed Jul. 2, 2013.
International Search Report and Written Opinion for PCT/US2008/078771, mailed Mar. 10, 2009.
International Preliminary Report on Patentability for PCT/US2008/078771, mailed Apr. 15, 2010.
Invitation to Pay Additional Fees for PCT/US2013/035416, mailed Jun. 10, 2013.
(Continued)

*Primary Examiner* — Traviss C McIntosh, III
(74) *Attorney, Agent, or Firm* — Wolf, Greenfield & Sacks, P.C.

(57) ABSTRACT

The present invention provides compounds of Formula (I); or a pharmaceutically acceptable form thereof; wherein $R^1, R^2, R^3, R^6, R^7, R^{12}, R^a$, and $R^b$ are as defined herein, and G is a group of Formula (a), (b), or (c): Formula (II), wherein $X_1$; $X_2, X_3, X_4, X_5, X_6, X_7, Y, R^C, R^d, R^z$, a, d, e, x, n, and m are as defined herein. The present invention further provides pharmaceutical compositions comprising a compound of Formula (I), kits comprising such compositions, methods of use and treatment, and preparative methods.

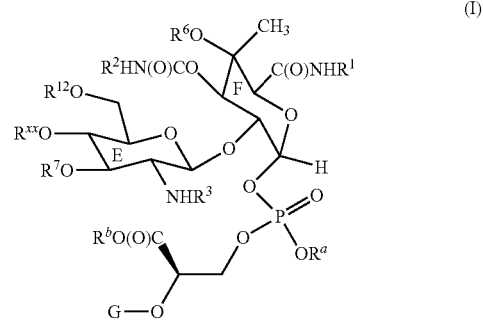

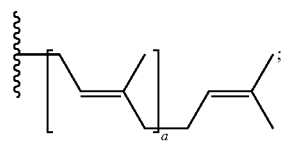

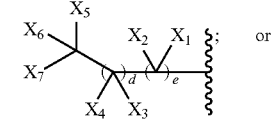

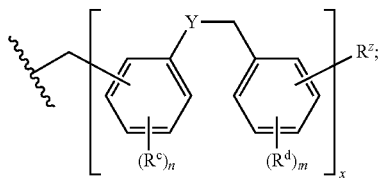

24 Claims, No Drawings

(56) References Cited

U.S. PATENT DOCUMENTS

| | | | |
|---|---|---|---|
| 4,270,537 A | 6/1981 | Romaine | |
| 4,522,811 A | 6/1985 | Eppstein et al. | |
| 4,596,556 A | 6/1986 | Morrow et al. | |
| 4,684,626 A | 8/1987 | Welzel et al. | |
| 4,790,824 A | 12/1988 | Morrow et al. | |
| 4,842,857 A | 6/1989 | Meyers et al. | |
| 4,886,499 A | 12/1989 | Cirelli et al. | |
| 4,940,460 A | 7/1990 | Casey et al. | |
| 4,941,880 A | 7/1990 | Burns | |
| 5,015,235 A | 5/1991 | Crossman | |
| 5,064,413 A | 11/1991 | McKinnon et al. | |
| 5,141,496 A | 8/1992 | Dalto et al. | |
| 5,190,521 A | 3/1993 | Hubbard et al. | |
| 5,206,405 A | 4/1993 | Aretz et al. | |
| 5,260,051 A | 11/1993 | Cho | |
| 5,260,206 A | 11/1993 | Aretz et al. | |
| 5,312,335 A | 5/1994 | McKinnon et al. | |
| 5,315,038 A | 5/1994 | Aretz et al. | |
| 5,316,929 A | 5/1994 | Aretz et al. | |
| 5,328,483 A | 7/1994 | Jacoby | |
| 5,334,144 A | 8/1994 | Alchas et al. | |
| 5,339,163 A | 8/1994 | Homma et al. | |
| 5,383,851 A | 1/1995 | McKinnon, Jr. et al. | |
| 5,417,662 A | 5/1995 | Hjertman et al. | |
| 5,454,971 A | 10/1995 | Sakai et al. | |
| 5,466,220 A | 11/1995 | Brenneman | |
| 5,480,381 A | 1/1996 | Weston | |
| 5,503,627 A | 4/1996 | McKinnon et al. | |
| 5,506,140 A | 4/1996 | Aretz et al. | |
| 5,520,639 A | 5/1996 | Peterson et al. | |
| 5,527,288 A | 6/1996 | Gross et al. | |
| 5,569,189 A | 10/1996 | Parsons | |
| 5,599,302 A | 2/1997 | Lilley et al. | |
| 5,649,912 A | 7/1997 | Peterson | |
| 5,704,911 A | 1/1998 | Parsons | |
| 5,736,533 A | 4/1998 | Simon et al. | |
| 5,888,721 A | 3/1999 | Rothstein et al. | |
| 5,893,397 A | 4/1999 | Peterson et al. | |
| 5,986,089 A | 11/1999 | Vertesy et al. | |
| 5,993,412 A | 11/1999 | Deily et al. | |
| 6,077,830 A | 6/2000 | Vertesy et al. | |
| 6,114,309 A | 9/2000 | Allanson et al. | |
| 6,153,381 A | 11/2000 | Rothstein | |
| 6,207,820 B1 | 3/2001 | Allanson et al. | |
| 6,242,424 B1 | 6/2001 | Riess et al. | |
| 6,274,716 B1 | 8/2001 | Allanson et al. | |
| 6,461,829 B1 | 10/2002 | Kahne | |
| 6,534,278 B1 | 3/2003 | Rothstein | |
| 6,911,318 B2 | 6/2005 | Kahne | |
| 6,913,895 B1 | 7/2005 | Goldman et al. | |
| 7,129,229 B2 | 10/2006 | Raddatz et al. | |
| 7,186,813 B1 | 3/2007 | Schweitzer et al. | |
| 8,604,004 B2 | 12/2013 | Kahne et al. | |
| 2003/0108969 A1 | 6/2003 | DeSousa et al. | |
| 2003/0129683 A1 | 7/2003 | Kahne | |
| 2003/0158093 A1 | 8/2003 | Sun et al. | |
| 2004/0018582 A1 | 1/2004 | Eggert et al. | |
| 2004/0042981 A1 | 3/2004 | Vertesy et al. | |
| 2004/0127403 A1 | 7/2004 | Parenti et al. | |
| 2004/0147441 A1 | 7/2004 | Leach et al. | |
| 2005/0026214 A1 | 2/2005 | Biton et al. | |
| 2005/0106555 A1 | 5/2005 | Desousa | |
| 2005/0186653 A1 | 8/2005 | Helmann et al. | |
| 2005/0287181 A1 | 12/2005 | Murthy | |
| 2005/0287198 A1 | 12/2005 | Murthy | |
| 2005/0287200 A1 | 12/2005 | Murthy | |
| 2005/0287219 A1 | 12/2005 | Murthy | |
| 2005/0287220 A1 | 12/2005 | Murthy | |
| 2006/0040891 A1 | 2/2006 | Jiang et al. | |
| 2006/0093632 A1 | 5/2006 | Murthy | |
| 2006/0094669 A1 | 5/2006 | Murthy | |
| 2006/0142217 A1 | 6/2006 | Meutermans et al. | |
| 2007/0060506 A1 | 3/2007 | Walsh et al. | |
| 2010/0279980 A1 | 11/2010 | Walker et al. | |
| 2011/0136759 A1 | 6/2011 | Kahne et al. | |
| 2015/0079618 A1 | 3/2015 | Kahne et al. | |

FOREIGN PATENT DOCUMENTS

| | | |
|---|---|---|
| WO | WO 97/13537 A1 | 4/1997 |
| WO | WO 97/37705 A1 | 10/1997 |
| WO | WO 99/26956 A1 | 6/1999 |
| WO | WO 99/34850 A1 | 7/1999 |
| WO | WO 00/52035 A1 | 9/2000 |
| WO | WO 00/64915 A1 | 11/2000 |
| WO | WO 03/020962 A2 | 3/2003 |
| WO | WO 2008/021367 A2 | 2/2008 |
| WO | WO 2009/046314 A2 | 4/2009 |
| WO | WO 2013/151697 A1 | 10/2013 |
| WO | WO 2013/152277 A2 | 10/2013 |
| WO | WO 2013/152279 A1 | 10/2013 |

OTHER PUBLICATIONS

International Search Report and Written Opinion for PCT/US2013/035416, mailed Oct. 15, 2013.

International Preliminary Report on Patentability for PCT/US2013/035416, mailed Oct. 16, 2014.

International Search Report and Written Opinion for PCT/US2013/030800, mailed Jun. 18, 2013.

International Preliminary Report on Patentability for PCT/US2013/030800, mailed Oct. 16, 2014.

International Search Report and Written Opinion for PCT/US2007/017999, mailed Sep. 30, 2008.

International Preliminary Report on Patentability for PCT/US2007/017999, mailed Feb. 26, 2009.

International Search Report and Written Opinion for PCT/US2013/035427, mailed Jun. 28, 2013.

International Preliminary Report on Patentability for PCT/US2013/035427, mailed Oct. 16, 2014.

Adachi et al., Degradation and reconstruction of moenomycin A and derivatives: dissecting the function of the isoprenoid chain. J Am Chem Soc. Nov. 1, 2006;128(43):14012-3.

Arai et al., Pholipomycin, a new member of phosphoglycolipid antibiotics. I. Taxonomy of producing organism and fermentation and isolation of pholipomycin. J Antibiot (Tokyo). Dec. 1977;30(12):1049-54.

Baizman et al., Antibacterial activity of synthetic analogues based on the disaccharide structure of moenomycin, an inhibitor of bacterial transglycosylase. Microbiology. Dec. 2000;146 Pt 12:3129-40.

Bardone et al., Teichomycins, new antibiotics from Actinoplanes teichomyceticus nov. sp. II. Extraction and chemical characterization. J Antibiot (Tokyo). Mar. 1978;31(3):170-7.

Barrett et al., Kinetic characterization of the glycosyltransferase module of Staphylococcus aureus PBP2. J Bacteriol. Mar. 2005;187(6):2215-7.

Belanger et al., Functional analysis of genes responsible for the synthesis of the B-band O antigen of Pseudomonas aeruginosa serotype O6 lipopolysaccharide. Microbiology. Dec. 1999;145 ( Pt 12):3505-21.

Bentley et al., Complete genome sequence of the model actinomycete Streptomyces coelicolor A3(2). Nature. May 9, 2002;417(6885):141-7.

Berge et al., Pharmaceutical salts. J Pharm Sci. Jan. 1977;66(1):1-19.

Bibb, Regulation of secondary metabolism in streptomycetes. Curr Opin Microbiol. Apr. 2005;8(2):208-15.

Bierman et al., Plasmid cloning vectors for the conjugal transfer of DNA from Escherichia coli to Streptomyces spp. Gene. Jul. 1, 1992;116(1):43-9.

Blackman et al., Tetrazine ligation: fast bioconjugation based on inverse-electron-demand Diels-Alder reactivity. J Am Chem Soc. Oct. 15, 2008;130(41):13518-9. Epub Sep. 18, 2008.

Blondelet-Rouault et al., Antibiotic resistance gene cassettes derived from the omega interposon for use in E. coli and Streptomyces. Gene. May 6, 1997;190(2):315-7.

Castro-Palomino et al., N-Tetrachlorophthaloyl-Protected Trichloroacetimidate of Glucosamine as Glycosyl Donor in Oligosaccharide Synthesis. Tetrahedron Lett. 1995;36:5343-46.

(56) References Cited

OTHER PUBLICATIONS

Chaffin et al., CpsK of *Streptococcus agalactiae* exhibits alpha2,3-sialyltransferase activity in Haemophilus ducreyi. Mol Microbiol. Jul. 2002;45(1):109-22.
Chang, Multidrug resistance ABC transporters. FEBS Lett. Nov. 27, 2003;555(1):102-5.
Chater, Streptomyces inside-out: a new perspective on the bacteria that provide us with antibiotics. Philos Trans R Soc Lond B Biol Sci. May 29, 2006;361(1469):761-8.
Chen et al., Vancomycin analogues active against vanA-resistant strains inhibit bacterial transglycosylase without binding substrate. Proc Natl Acad Sci U S A. May 13, 2003;100(10):5658-63. Epub Apr. 24, 2003.
Cheng et al., Domain requirement of moenomycin binding to bifunctional transglycosylases and development of high-throughput discovery of antibiotics. Proc Natl Acad Sci U S A. Jan. 15, 2008;105(2):431-6. Epub Jan. 8, 2008.
Coates et al., Stereoselective Synthesis of Moenocinol and Assignment of Its Carbon-13 Nuclear Magnetic Resonance Spectrum. J Org Chem. 1980;45:2685-97.
Crich et al., Are Glycosyl Triflates Intermediates in the Sulfoxide Glycosylation Method? A Chemical and 1H, 13C, and 19F NMR Spectroscopic Investigation. J Am Chem Soc. 1997;119:11217-23.
Crich et al., Chapter 2. Gylcosylation with Sulfoxides and Sulfinates as Donors or Promoters. Org React. 2004;64:115-251.
Crich et al., Why are the hydroxy groups of partially protected N-acetylglucosamine derivatives such poor glycosyl acceptors, and what can be done about it? A comparative study of the reactivity of N-acetyl-, N-phthalimido-, and 2-azido-2-deoxy-glucosamine derivatives in glycosylation. 2-Picolinyl ethers as reactivity-enhancing replacements for benzyl ethers. J Am Chem Soc. Jul. 18, 2001;123(28):6819-25.
Daghish et al., Tetrafunctional photoaffinity labels based on Nakanishi's m-nitroalkoxy-substituted phenyltrifluoromethyldiazirine. Angew Chem Int Ed Engl. Jul. 2, 2002;41(13):2293-7.
Dairi, Studies on biosynthetic genes and enzymes of isoprenoids produced by actinomycetes. J Antibiot (Tokyo). Apr. 2005;58(4):227-43.
Datsenko et al., One-step inactivation of chromosomal genes in *Escherichia coli* K-12 using PCR products. Proc Natl Acad Sci U S A. Jun. 6, 2000;97(12):6640-5.
Debenham et al., Two New Orthogonal Amine-Protecting Groups That Can Be Cleaved under Mild or Neutral Conditions. J Am Chem Soc. 1995;117:3302-03.
Decker et al., A general approach for cloning and characterizing dNDP-glucose dehydratase genes from actinomycetes. FEMS Microbiol Lett. Aug. 1, 1996;141(2-3):195-201.
Dirksen et al., Rapid oxime and hydrazone ligations with aromatic aldehydes for biomolecular labeling. Bioconjug Chem. Dec. 2008;19(12):2543-8.
Du et al., Identification and functional analysis of dTDP-glucose-4,6-dehydratase gene and its linked gene cluster in an aminoglycoside antibiotics producer of Streptomyces tenebrarius H6. Curr Microbiol. Aug. 2004;49(2):99-107.
Durr et al., Biosynthesis of the terpene phenalinolactone in *Streptomyces* sp. Tü6071: analysis of the gene cluster and generation of derivatives. Chem Biol. Apr. 2006;13(4):365-77.
Ebenezer, Colabomycin Co-Metabolites. Synthesis of 2880-II, A Metabolite Related to Ferulic Acid. J Synth Commun. 1991;21:351-58.
Eichhorn et al., Characterization of moenomycin antibiotics from medicated chicken feed by ion-trap mass spectrometry with electrospray ionization. Rapid Commun Mass Spectrom. 2005;19(15):2179-86.
El-Abadla et al., Moenomycin A: The Role of the Methyl Group in the Moenuronamide Unit and a General Discussion of Structure-Activity Relationships. Tetrahedron. 1999;55(3):699-722.
Ellervik et al., A High Yielding Chemical Synthesis of Sialyl Lewis x Tetrasaccharide and Lewis x Trisaccharide; Examples of Regio-and Stereodifferentiated Glycosylations. J Org Chem. 1998;63:9314-22.
Fehlhaber et al., Moenomycin A: A Structural Revision and New Structure-Activity Relations. Tetrahedron. 1990;46(5):1557-68.
Feng et al., Structure of the Shigella dysenteriae 7 O antigen gene cluster and identification of its antigen specific genes. Microb Pathog. Feb. 2004;36(2):109-15.
Flett et al., High efficiency intergeneric conjugal transfer of plasmid DNA from *Escherichia coli* to methyl DNA-restricting streptomycetes. FEMS Microbiol Lett. Oct. 15, 1997;155(2):223-9.
Fuse et al., Functional and Structural Analysis of a Key Region of the Cell Wall Inhibitor Moenomycin. ACS Chem Biol. 2010;5(7):701-711.
Gampe et al., Tuning the moenomycin pharmacophore to enable discovery of bacterial cell wall synthesis inhibitors. J Am Chem Soc. Mar. 13, 2013;135(10):3776-9. doi: 10.1021/ja4000933. Epub Mar. 4, 2013.
Garegg et al., Formation of Internucleotidic Bonds via Phosphonate Intermediates. Chem Scr. 1985;25:280-82.
Garneau et al., Synthesis of mono- and disaccharide analogs of moenomycin and lipid II for inhibition of transglycosylase activity of penicillin-binding protein 1b. Bioorg Med Chem. Dec. 15, 2004;12(24):6473-94.
Genbank Submission; NIH/NCBI, Accession No. AAF24002; Belanger et al.; Jan. 12, 2000.
Genbank Submission; NIH/NCBI, Accession No. AAG34163; Yoo et al.; Mar. 6, 2001.
Genbank Submission; NIH/NCBI, Accession No. AAO06921; Rascher et al.; Feb. 21, 2003.
Genbank Submission; NIH/NCBI, Accession No. AAU93096; Ward et al; Nov. 21, 2011.
Genbank Submission; NIH/NCBI, Accession No. AAX98210; McAlpine et al.; Apr. 25, 2005.
Genbank Submission; NIH/NCBI, Accession No. AY240962; Petricek et al.; Jul. 5, 2006.
Genbank Submission; NIH/NCBI, Accession No. BAC68501; Omura et al.; Dec. 21, 2007.
Genbank Submission; NIH/NCBI, Accession No. BAC68502; Omura et al.; Dec. 21, 2007.
Genbank Submission; NIH/NCBI, Accession No. BAC70368; Omura et al.; Dec. 21, 2007.
Genbank Submission; NIH/NCBI, Accession No. CAA22758; Bentley et al.; Oct. 23, 2008.
Genbank Submission; NIH/NCBI, Accession No. CAC01594; Bentley et al.; Oct. 23, 2008.
Genbank Submission; NIH/NCBI, Accession No. CAC37544; Bentley et al.; Oct. 23, 2008.
Genbank Submission; NIH/NCBI, Accession No. CAC37545; Bentley et al.; Oct. 23, 2008.
Genbank Submission; NIH/NCBI, Accession No. CAI08539; Rabus et al.; Sep. 11, 2009.
Genbank Submission; NIH/NCBI, Accession No. EAM38951; Jun. 15, 2005.
Genbank Submission; NIH/NCBI, Accession No. EAO07657; Jul. 26, 2005.
Genbank Submission; NIH/NCBI, Accession No. EAS11435; Apr. 9, 2007.
Genbank Submission; NIH/NCBI, Accession No. EAS23724; Mar. 22, 2006.
Genbank Submission; NIH/NCBI, Accession No. EAS99725; Apr. 18, 2006.
Genbank Submission; NIH/NCBI, Accession No. JC7965; Nemoto et al.; Mar. 15, 2004.
Genbank Submission; NIH/NCBI, Accession No. NP_142754; Kawarabayasi et al.; Jan. 19, 2012.
Genbank Submission; NIH/NCBI, Accession No. NP_220145; Griffiths et al.; Sep. 15, 2011.
Genbank Submission; NIH/NCBI, Accession No. NP_630535; Hsiao et al.; Jan. 19, 2012.
Genbank Submission; NIH/NCBI, Accession No. YP_074610; Ueda et al.; Jan. 23, 2012.

(56) References Cited

OTHER PUBLICATIONS

Genbank Submission; NIH/NCBI, Accession No. YP_075255; Ueda et al.; Jan. 23, 2012.
Genbank Submission; NIH/NCBI, Accession No. YP_075256; Ueda et al.; Jan. 23, 2012.
Genbank Submission; NIH/NCBI, Accession No. ZP_00616987; Heuts et al.; Jun. 28, 2007.
Gildersleeve et al., Scavenging Byproducts in the Sulfoxide Glycosylation Reaction: Application to the Synthesis of Ciclamycin O. J Am Chem Soc. 1999;121:6176-82.
Gildersleeve et al., Sulfenate Intermediates in the Sulfoxide Glycosylation Reaction. J Am Chem Soc. 1998;120:5961-69.
Goldman et al., Differential antibacterial activity of moenomycin analogues on gram-positive bacteria. Bioorg Med Chem Lett. Oct. 16, 2000;10(20):2251-4.
Goldman et al., Inhibition of transglycosylation involved in bacterial peptidoglycan synthesis. Curr Med Chem. Aug. 2000;7(8):801-20.
Gromyko et al., Generation of Streptomyces globisporus SMY622 strain with increased landomycin E production and it's initial characterization. J Antibiot (Tokyo). Jun. 2004;57(6):383-9.
Gust et al., PCR-targeted *Streptomyces* gene replacement identifies a protein domain needed for biosynthesis of the sesquiterpene soil odor geosmin. Proc Natl Acad Sci U S A. Feb. 18, 2003;100(4):1541-6. Epub Jan. 31, 2003.
Halliday et al., Targeting the forgotten transglycosylases. Biochem Pharmacol. Mar. 30, 2006;71(7):957-67. Epub Nov. 18, 2005.
Hang et al., Probing Glycosyltransferase Activities with the Staudinger Ligation. J Am Chem Soc. 2004;126(1):6-7.
Hang et al., Small molecule inhibitors of mucin-type O-linked glycosylation from a uridine-based library. Chem Biol. Mar. 2004;11(3):337-45.
Hang et al., The chemistry and biology of mucin-type O-linked glycosylation. Bioorg Med Chem. Sep. 1, 2005;13(17):5021-34.
He et al., Isolation and structural elucidation of AC326-alpha, a new member of the moenomycin group. J Antibiot (Tokyo). Feb. 2000;53(2):191-5.
Hebler-Klintz et al., The First Moenomycin Antibiotic Without the Methyl-Branched Uronic Acid Constituent.- Unexpected Structure Activity Relations. Tetrahedron. 1993;35:7667-78.
Hernández-Torres et al., Temperature-controlled regioselectivity in the reductive cleavage of p-methoxybenzylidene acetals. J Org Chem. Oct. 15, 2004;69(21):7206-11.
Hodgson, Primary metabolism and its control in streptomycetes: a most unusual group of bacteria. Adv Microb Physiol. 2000;42:47-238.
Hong et al., A signal transduction system in Streptomyces coelicolor that activates the expression of a putative cell wall glycan operon in response to vancomycin and other cell wall-specific antibiotics. Mol Microbiol. Jun. 2002;44(5):1199-1211.
Hong et al., Inactivation of the carbamoyltransferase gene refines post-polyketide synthase modification steps in the biosynthesis of the antitumor agent geldanamycin. J Am Chem Soc. Sep. 15, 2004;126(36):11142-3.
Hopwood, Soil to genomics: the Streptomyces chromosome. Annu Rev Genet. 2006;40:1-23.
Ishikawa et al., FramePlot: a new implementation of the frame analysis for predicting protein-coding regions in bacterial DNA with a high G + C content. FEMS Microbiol Lett. May 15, 1999;174(2):251-3.
Iyobe et al., Sex pili mutants isolated by macarbomycin treatment. Antimicrob Agents Chemother. May 1973;3(5):614-20.
Jabbouri et al., Involvement of nodS in N-methylation and nodU in 6-O-carbamoylation of *Rhizobium* sp. NGR234 nod factors. J Biol Chem. Sep. 29, 1995;270(39):22968-73.
Jansson et al., 2-(Trimethylsilyl)ethyl Glycosides. Synthesis, Anomeric Deblocking, and Transformation into 1,2-Trans 1-O-Acyl Sugars. J Org Chem. 1988;53:5629-47.
Kahne et al., Glycosylation of Unreactive Substrates. J Am Chem Soc. 1989;111:6881-82.

Kaplan et al., Genes involved in the synthesis and degradation of matrix polysaccharide in Actinobacillus actinomycetemcomitans and Actinobacillus pleuropneumoniae biofilms. J Bacteriol. Dec. 2004;186(24):8213-20.
Kartha et al., Iodine: A Versatile Reagent in Carboyhydrate Chemistry III. Efficient Activation of Glycosyl Halides in Combination with DDQ1. Tetrahedron Lett. 1996;37:8807-10.
Kaur, Expression and characterization of DrrA and DrrB proteins of Streptomyces peucetius in *Escherichia coli*: DrrA is an ATP binding protein. J Bacteriol. Feb. 1997;179(3):569-75.
Kawasaki et al., Biosynthesis of a natural polyketide-isoprenoid hybrid compound, furaquinocin A: identification and heterologous expression of the gene cluster. J Bacteriol. Feb. 2006;188(4):1236-44.
Kawasaki et al., Interconversion of the product specificity of type I eubacterial farnesyl diphosphate synthase and geranylgeranyl diphosphate synthase through one amino acid substitution. J Biochem. Jan. 2003;133(1):83-91.
Khidekel et al., A chemoenzymatic approach toward the rapid and sensitive detection of O-GlcNAc posttranslational modifications. J Am Chem Soc. Dec. 31, 2003;125(52):16162-3.
Knirel et al., Somatic antigens of Shigella: structure of the O-specific polysaccharide chain of the Shigella dysenteriae type 7 lipopolysaccharide. Carbohydr Res. Aug. 15, 1988;179:51-60.
Kudo et al., A new family of glucose-1-phosphate/glucosamine-1-phosphate nucleotidylyltransferase in the biosynthetic pathways for antibiotics. J Am Chem Soc. Feb. 16, 2005;127(6):1711-8.
Kuiper et al., A Selective and Mild Synthetic Route to Dialkyl Phosphates. Synthesis. 2003;5:695-98.
Lay et al., Synthesis of N-acetylglucosamine containing Lewis A and Lewis X building blocks based on N-tetrachlorophthaloyl protection—synthesis of Lewis X pentasaccharide. Carbohydr Res. Aug. 1998;310(3):157-71.
Lehtovaara et al., A new method for random mutagenesis of complete genes: enzymatic generation of mutant libraries in vitro. Protein Eng. Apr. 1998;2(1):63-8.
Leimkuhler et al., Differential inhibition of *Staphylococcus aureus* PBP2 by lycopeptides antibiotics. J Am Chem Soc. Mar. 16, 2005;127(10):3250-1.
Leskiw et al., Accumulation of bldA-specified tRNA is temporally regulated in Streptomyces coelicolor A3(2). J Bacteriol. Apr. 1993;175(7):1995-2005.
Leskiw et al., TTA codons in some genes prevent their expression in a class of developmental, antibiotic-negative, Streptomyces mutants. Proc Natl Acad Sci U S A. Mar. 15, 1991;88(6):2461-5.
Lin et al., Sequence analysis and molecular characterization of genes required for the biosynthesis of type 1 capsular polysaccharide in *Staphylococcus aureus*. J Bacteriol. Nov. 1994;176(22):7005-16.
Linnett et al., Additional antibiotic inhibitors of peptidoglycan synthesis. Antimicrob Agents Chemother. Sep. 1973;4(3):231-6.
Liu et al., Acceptor specificity and inhibition of the bacterial cell-wall glycosyltransferase MurG. Chembiochem. Jul. 7, 2003;4(7):603-9.
Lombo et al., The mithramycin gene cluster of *Streptomyces argillaceus* contains a positive regulatory gene and two repeated DNA sequences that are located at both ends of the cluster. J Bacteriol. Jan. 1999;181(2):642-7.
Lovering et al., Structural insight into the transglycosylation step of bacterial cell-wall biosynthesis. Science. Mar. 9, 2007;315(5817):1402-5.
Luning et al., Moenomycin-Type Transglycosylase Inhibitors: Inhibiting Activity vs. Topology around the Phosphoric Acid Diester Group. Tetrahedron Lett. 1994;35(12):1859-62.
Luzhetskii et al., [Interspecies conjugation of *Escherichia coli*-Streptomyces globisporus 1912 using integrative plasmid pSET152 and its derivatives]. Genetika. Oct. 2001;37(10):1340-7. Russian.
Luzhetskyy et al., Iteratively acting glycosyltransferases involved in the hexasaccharide biosynthesis of landomycin A. Chem Biol. Jul. 2005;12(7):725-9.
Marzian et al., Moenomycin A: Reactions at the Lipid Part. New Structure-Activity Relations. Tetrahedron. 1994;50:5299-308.
McAlpine et al., Microbial genomics as a guide to drug discovery and structural elucidation: ECO-02301, a novel antifungal agent, as an example. J Nat Prod. Apr. 2005;68(4):493-6.

(56) References Cited

OTHER PUBLICATIONS

McKeegan et al., The structure and function of drug pumps: an update. Trends Microbiol. Jan. 2003;11(1):21-9.
Men et al., Substrate Synthesis and Activity Assay for MurG. J. Am. Chem. Soc. Feb. 1998;120(10):2484-2485.
Mendez et al., The role of ABC transporters in antibiotic-producing organisms: drug secretion and resistance mechanisms. Res Microbiol. Apr.-May 2001;152(3-4):341-50.
Metten et al., The First Enzymatic Degradation Products of the Antibiotic Moenomycin A. Tetrahedron. 1992;48:8401-18.
Meyers et al., The Diumycins. New Members of an Antibiotic Family Having Prolonged In Vivo Activity. J Antibiot. 1969;22:490-93.
Müller et al., Utility of Glycosyl Phosphites as Glycosyl Donors-Fructofuranosyl and 2-Deoxyhexopyranosyl Phosphites in Glycoside Bond Formation. Tetrahedron Lett. 1994;35:4763-66.
Murrell et al., Biochemical characterization of the SgcA1 alpha-D-glucopyranosyl-1-phosphate thymidylyltransferase from the enediyne antitumor antibiotic C-1027 biosynthetic pathway and overexpression of sgcA1 in Streptomyces globisporus to improve C-1027 production. J Nat Prod. Feb. 2004;67(2):206-13.
Muth et al., A vector sytem with temperature-sensitive replication for gene disruption and mutational cloning in streptomycetes. Mol Gen Genet. 1989;219:341-48.
Nakagawa et al., Biosynthesis of asukamycin. Formation of the 2-amino-3-hydroxycyclopent-2-enone-moiety. J Chem Soc Chem Commun. 1985:519-21.
Nemoto et al., Purification and characterization of geranylgeranylglyceryl phosphate synthase from a thermoacidophilic archaeon, Thermoplasma acidophilum. J Biochem. May 2003;133(5):651-7.
Neundorf et al., Evidence for the combined participation of a C10 and a C15 precursor in the biosynthesis of moenocinol, the lipid part of the moenomycin antibiotics. Chembiochem. Nov. 7, 2003;4(11):1201-5.
Oh et al., Denaturation of circular or linear DNA facilitates targeted integrative transformation of Streptomyces coelicolor A3(2): possible relevance to other organisms. J Bacteriol. Jan. 1997;179(1):122-7.
Ostash et al., A streamlined metabolic pathway for the biosynthesis of moenomycin A. Chem Biol. Mar. 2007;14(3):257-67.
Ostash et al., Bacterial transglycosylase inhibitors. Curr Opin Chem Biol. Oct. 2005;9(5):459-66.
Ostash et al., Complete characterization of the seventeen step moenomycin biosynthetic pathway. Biochemistry. Sep. 22, 2009;48(37):8830-41.
Pacholec et al., Characterization of the aminocoumarin ligase SimL from the simocyclinone pathway and tandem incubation with NovM,P,N from the novobiocin pathway. Biochemistry. Mar. 29, 2005;44(12):4949-56.
Paton et al., Molecular characterization of the locus encoding biosynthesis of the lipopolysaccharide O antigen of *Escherichia coli* serotype O113. Infect Immun. Nov. 1999;67(11):5930-7.
Paulsen, Advances in Selective Chemical Syntheses of Complex Oligosaccharides. Angew Chem Int Ed Engl. 1982;21:155-73.
Petricek et al., Occurrence of two 5-aminolevulinate biosynthetic pathways in *Streptomyces nodosus* subsp. *Asukaensis* is linked with the production of asukamycin. J Bacteriol. Jul. 2006;188(14):5113-23.
Pfaller, Flavophospholipol use in animals: positive implications for antimicrobial resistance based on its microbiologic properties. Diagn Microbiol Infect Dis. Oct. 2006;56(2):115-21. Epub May 15, 2006.
Ramakrishnan et al., alpha-Lactalbumin (LA) stimulates milk beta-1,4-galactosyltransferase I (beta 4Gal-T1) to transfer glucose from UDP-glucose to N-acetylglucosamine. Crystal structure of beta 4Gal-T1 x LA complex with UDP-Glc. J Biol Chem. Oct. 5, 2001;276(40):37665-71. Epub Aug. 2, 2001.
Ramakrishnan et al., Structure-based design of beta 1,4-galactosyltransferase I (beta 4Gal-T1) with equally efficient N-acetylgalactosaminyltransferase activity: point mutation broadens beta 4Gal-T1 donor specificity. J Biol Chem. Jun. 7, 2002;277(23):20833-9. Epub Mar. 26, 2002.
Rascher et al., Cloning and characterization of a gene cluster for geldanamycin production in Streptomyces hygroscopicus NRRL 3602. FEMS Microbiol Lett. Jan. 28, 2003;218(2):223-30.
Rebets et al., Expression of the regulatory protein LndI for landomycin E production in Streptomyces globisporus 1912 is controlled by the availability of tRNA for the rare UUA codon. FEMS Microbiol Lett. Mar. 2006;256(1):30-7.
Redenbach et al., The Streptomyces lividans 66 chromosome contains a 1 MB deletogenic region flanked by two amplifiable regions. Mol Gen Genet. Nov. 1993;241(3-4):255-62.
Riedl et al., Impact of flavophospholipol and vancomycin on conjugational transfer of vancomycin resistance plasmids. Antimicrob Agents Chemother. Nov. 2000;44(11):3189-92.
Ritzeler et al., Search for new moenomycin structure-activity relationships Synthesis of a trisaccharide precursor of a moenomycin analogue. Tetrahedron. 1997;53:1665-74.
Rose et al., Consensus-degenerate hybrid oligonucleotide primers for amplification of distantly related sequences. Nucleic Acids Res. Apr. 1, 1998;26(7):1628-35.
Rühl et al., A trifunctional reagent for photoaffinity labeling. Tetrahedron Lett. 2000;41(23):4555-58.
Schmidt et al., Nitriles as Solvents in Glycosylation Reactions: Highly Selective β-Glycoside Synthesis. Synlett. 1990;11:694-96.
Schurer et al., Fluorescence correlation spectroscopy as a new method for the investigation of aptamer/target interactions. Biol Chem. Mar. 2001;382(3):479-81.
Schuricht et al., Studies on the Biosynthesis of the Antibiotic Moenomycin A. J Prakt Chem. 2000;342(8):761-72.
Schuricht et al., The Biosynthesis of Moenocinol, the Lipid Part of the Moenomycin Antibiotics. Tetrahedron Lett. 2001;42:3835-37.
Sekurova et al., In vivo analysis of the regulatory genes in the nystatin biosynthetic gene cluster of Streptomyces noursei ATCC 11455 reveals their differential control over antibiotic biosynthesis. J Bacteriol. Mar. 2004;186(5):1345-54.
Shin et al., Total synthesis and structure of the ramoplanin A1 and A3 aglycons: two minor components of the ramoplanin complex. Proc Natl Acad Sci U S A. Aug. 17, 2004;101(33):11977-9. Epub Jun. 2, 2004.
Sletten et al., A bioorthogonal quadricyclane ligation. J Am Chem Soc. Nov. 9, 2011;133(44):17570-3. Epub Oct. 17, 2011.
Slusarchyk et al., The Structure of a Novel Lipid from the Antibiotic Diumycin. J Am Chem Soc. 1970;92:4486-88.
Slusarchyk et al., The structure of the lipid portion of the antibiotic prasinomycin. Tetrahedron Lett. Feb. 1969;8:659-62.
Smith et al., The cps genes of *Streptococcus suis* serotypes 1, 2, and 9: development of rapid serotype-specific PCR assays. J Clin Microbiol. Oct. 1999;37(10):3146-52.
Soderberg et al., Geranylgeranylglyceryl phosphate synthase. Characterization of the recombinant enzyme from Methanobacterium thermoautotrophicum. Biochemistry. Dec. 11, 2001;40(49):14847-54.
Sosio et al., The gene cluster for the biosynthesis of the glycopeptide antibiotic A40926 by *nonomuraea* species. Chem Biol. Jun. 2003;10(6):541-9.
Srivastava et al., Combined chemical-enzymic synthesis of deoxygenated oligosaccharide analogs: transfer of deoxygenated D-GlcpNAc residues from their UDP-GlcpNAc derivatives using N-acetylglucosaminyltransferase I. Carbohydr Res. Oct. 25, 1990;207(2):259-76.
Stawinski, Chapter 8. Some Aspects of H-Phosphonate Chemistry. In: Handbook of Organophosphorus Chemistry. R. Engel ed. Marcel Dekker, New York. 1992:377-434.
Stumpp et al., Synthesis of Moenocinol. Tetrahedron. 1986;42:5941-48.
Subramaniam-Niehaus et al., Isolation and analysis of moenomycin and its biosynthetic intermediates from Streptomyces ghanaensis (ATCC 14672) wildtype and selected mutants. Z Naturforsch C. Mar.-Apr. 1997;52(3-4):217-26.
Tachibana et al., Novel prenyltransferase gene encoding farnesylgeranyl diphosphate synthase from a hyperthermophilic

(56) References Cited

OTHER PUBLICATIONS archaeon, Aeropyrum pernix. Molecular evolution with alteration in product specificity. Eur J Biochem. Jan. 2000;267(2):321-8.

Tahlan et al., Three unlinked gene clusters are involved in clavam metabolite biosynthesis in Streptomyces clavuligerus. Can J Microbiol. Oct. 2004;50(10):803-10.

Tai et al., Parallel identification of O-GlcNAc-modified proteins from cell lysates. J Am Chem Soc. Sep. 1, 2004;126(34):10500-1.

Takahashi et al., A two-stage one-pot enzymatic synthesis of TDP-L-mycarose from thymidine and glucose-l-phosphate. J Am Chem Soc. Feb. 8, 2006;128(5):1432-3.

Takahashi et al., Macarbomycin, a new antibiotic containing phosphorus. J Antibiot (Tokyo). Jan. 1970;23(1):48-50.

Taylor et al., The total synthesis of moenomycin A. J Am Chem Soc. Nov. 29, 2006;128(47):15084-5.

Thuy et al., Functional characterizations of novWUS involved in novobiocin biosynthesis from Streptomyces spheroides. Arch Biochem Biophys. Apr. 1, 2005;436(1):161-7.

Tirado et al., Stereochemistry of the Iodocarbonation of cis- and trans-3-Methyl-4-pentene-1,2-diols: The Unusual Formation of Several Anti Iodo Carbonates. J Org Chem. 1993;58:5666-73.

Trepanier et al., The positive activator of cephamycin C and clavulanic acid production in Streptomyces clavuligerus is mistranslated in a bldA mutant. Microbiology. Mar. 2002;148(Pt 3):643-56.

Tschesche et al., Uber den Lipoidteil Moenocinol des Antibiotikums Moenomycin. Tetrahedron Letters. 1968;24:2905-09.

Van Heijenoort, Formation of the glycan chains in the synthesis of bacterial peptidoglycan. Glycobiology. Mar. 2001;11(3):25R-36R.

Vocadlo et al., A chemical approach for identifying O-GlcNAc-modified proteins in cells. Proc Natl Acad Sci U S A. Aug. 5, 2003;100(16):9116-21. Epub Jul. 21, 2003.

Vocadlo et al., A strategy for functional proteomic analysis of glycosidase activity from cell lysates. Angew Chem Int Ed Engl. Oct. 11, 2004;43(40):5338-42.

Vogel et al., Moenomycin analogues with modified lipid side chains from indium-mediated Barbier-type reaction. Tetrahedron. 2001;57:4139-46.

Vogel et al., Some selective reactions of moenomycin A. Bioorg Med Chem Lett. Sep. 4, 2000;10(17):1963-5.

Volke et al., Characterisation of antibiotic moenomycin A interaction with phospholipid model membranes. Chem Phys Lipids. Feb. 28, 1997;85(2):115-23.

Volke et al., On Penicillin-Binding Protein 1b Affinity-Labeling Reagents. Helvetica Chimica Acta. 2003;86(12):4214-32.

Wallhausser et al., Moenomycin, a new antibiotic. I. Fermentation and isolation. Antimicrob Agents Chemother (Bethesda). 1965;5:734-6.

Wang et al., The pgaABCD locus of *Escherichia coli* promotes the synthesis of a polysaccharide adhesin required for biofilm formation. J Bacteriol. May 2004;186(9):2724-34.

Weber et al., Exploiting the genetic potential of polyketide producing streptomycetes. J Biotechnol. Dec. 19, 2003;106(2-3):221-32.

Weisenborn et al., The prasinomycins: antibiotics containing phosphorus. Nature. Mar. 18, 1967;213(5081):1092-4.

Welzel et al., [Moenomycin A: Spaltung Des Antibiotikums Mit Trifluoressigsaure/2-Propanol Und Bestimmung Der Verknupfung Von D-Glucose Und 2-Acetamido-2-Desoxy-D-Glucose.] Tetrahedron. 1981;37:97-104. German.

Welzel et al., [Zur Struktur Eines 2-Amino-Cyclopentandion-1,3, Galakturonsaure and Chinovos-Amin Enthaltenden Hydrolyseruchstucks Des Antibiotikums Moenomycin A.] Tetrahedron Lett. 1973;3:227-30. German.

Welzel et al., Moenomycin A: Minimum Structural Requirements for Biological Activity. Tetrahedron. 1987;43:585-98.

Welzel, Syntheses around the transglycosylation step in peptidoglycan biosynthesis. Chem Rev. Dec. 2005;105(12):4610-60.

Welzel, Transglycosylase Inhibition. In: Antibiotics and antiviral compounds- chemical synthesis and modification. Krohn et al., eds. Weinheim, Germany. 1993:373-78.

Westerduin et al., Synthesis of the Fragment GlcNAc-α(1-P-6)-GlcNac of the Cell Wall Polymer of *Staphylococcus lactis* Having Repeating N-Acetyl-D-Glucosamine Phosphate Units. Tetrahedron Lett. 1986;27:6271-74.

Westrich et al., Cloning and characterization of a gene cluster from Streptomyces cyanogenus S136 probably involved in landomycin biosynthesis. FEMS Microbiol Lett. Jan. 15, 1999;170(2):381-7.

White et al., New oligomeric catalyst for the hydrolytic kinetic resolution of terminal epoxides under solvent-free conditions. Tetrahedron Asymm 2003;14:3633-38.

Wilen et al., Strategies in Optical Resolutions. Tetrahedron. 1977;33:2725-36.

Wilen, Tables of Resolving Agents and Optical Resolutions. E.L. Eliel, ed. Universtify of Notre Dame Press, Notre Dame, IN. 1972:268-98.

Wilson et al., Molecular analysis of tlrB, an antibiotic-resistance gene from tylosin-producing Streptomyces fradiae, and discovery of a novel resistance mechanism. J Antibiot (Tokyo). Mar. 1999;52(3):288-96.

Wolff, Burger's Medicinal Chemistry. 5th ed., Part 1. John Wiley & Sons, 1995, pp. 975-977.

Xiang et al., The crystal structure of *Escherichia coli* MoeA and its relationship to the multifunctional protein gephyrin. Structure. Apr. 4, 2001;9(4):299-310.

Ye et al., Better substrates for bacterial transglycosylases. J Am Chem Soc. Apr. 4, 2001;123(13):3155-6.

Yu et al., The biosynthetic gene cluster of the maytansinoid antitumor agent ansamitocin from Actinosynnema pretiosum. Proc Natl Acad Sci U S A. Jun. 11, 2002;99(12):7968-73.

Yuan et al., Crystal structure of a peptidoglycan glycosyltransferase suggests a model for processive glycan chain synthesis. Proc Natl Acad Sci U S A. Mar. 27, 2007;104(13):5348-53. Epub Mar. 8, 2007.

Zalkin et al., Enzymes utilizing glutamine as an amide donor. Adv Enzymol Relat Areas Mol Biol. 1998;72:87-144.

Zehl et al., Characterization of moenomycin antibiotic complex by multistage MALDI-IT/RTOF-MS and ESI-IT-MS. J Am Soc Mass Spectrom. Aug. 2006;17(8):1081-90. Epub May 30, 2006.

Zhang et al., A Simple Statistical Parameter for Use in Evaluation and Validation of High Throughput Screening Assays. J Biomol Screen. 1999;4(2):67-73.

Zhang et al., Molecular and chemical characterization of the lipopolysaccharide O-antigen and its role in the virulence of Yersinia enterocolitica serotype O:8. Mol Microbiol. Jan. 1997;23(1):63-76.

Zhu et al., Identification of the function of gene lndM2 encoding a bifunctional oxygenase-reductase involved in the biosynthesis of the antitumor antibiotic landomycin E by Streptomyces globisporus 1912 supports the originally assigned structure for landomycinone. J Org Chem. Jan. 21, 2005;70(2):631-8.

\* cited by examiner

MOENOMYCIN ANALOGS, METHODS OF SYNTHESIS, AND USES THEREOF

RELATED APPLICATIONS

The present application is a national stage filing under 35 U.S.C. §371 of international PCT application, PCT/US2013/035416, filed Apr. 5, 2013, which claims priority under 35 U.S.C. §119(e) to U.S. provisional patent application, U.S. Ser. No. 61/621,161, filed Apr. 6, 2012, each of which is incorporated herein by reference.

GOVERNMENT FUNDING

This invention was made with U.S. Government support under grant GM066174 awarded by the National Institutes of Health. The U.S. Government has certain rights in the invention.

BACKGROUND OF THE INVENTION

Bacteria have the ability to generate resistance to antibiotics through lateral gene transfer, mutation of enzymes, or the expression of enzymes which actively pump the antibiotic out of the cell or break it down. Over the past 10 years, resistance to existing antibiotics has become a significant problem in many countries. Vancomycin is currently the drug of last resort to combat multi-drug-resistant Gram-positive bacteria. In many places vancomycin-resistant *Staphylococcus aureus* and Enterococci (VRE) have been discovered. There is thus a desperate need for a new antibiotic drug to replace this drug of last resort.

There are a host of cytoplasmic targets for the development of new antibacterials, such as gyrase inhibitors, protein synthesis inhibitors, muramyl cascade inhibitors, and many more. The major hurdle in designing such drugs is that in addition to enzyme based activity these drugs need to cross the bacterial cell wall to exert their antibacterial effect. On the other hand, enzymes involved in synthesis of the bacterial cell wall exist on the cell wall exterior, and therefore drugs inhibiting these enzymes can exert their bactericidal or bacteriostatic effect without having to cross the cell wall. For example, penicillins, cephalosporins, and moenomycin are antibiotics that interact with bacterial transpeptidase enzymes. Vancomycin does not interact with bacterial transpeptidase enzymes but rather sequesters the substrate of the enzyme.

Moenomycin is the only known natural product that directly inhibits the synthesis of bacterial peptidoglycan (PG). The biological activity of moenomycin is remarkable compared with that of most other natural antibiotics: it is 10-1000 times more potent than vancomycin against Gram-positive organisms. See, e.g., Ostash and Walker, *Curr. Opin. Chem. Biol.* (2005) 9:459-466; Goldman et al., *Curr. Med. Chem.* (2000) 7:801-820. Structure-activity relationship studies of Moneomycin analogs conducted on the saccharide portion of the molecule have revealed that moenomycins with at least three carbohydrate units (C, E, and F) are active in vivo against Gram-positive bacteria. See, e.g., Garneau et al., *Bioorganic & Medicinal Chemistry* (2004) 12:6473-6494. Furthermore, while the phosporyl group and the carboxylate group of the phosphoglycerate linker are now considered important for bioactivity, the moenocinol chain is also considered to be an important structural component of the molecule and probably contributes to target binding both by direct interactions with the hydrophobic funnel that leads to the membrane and by membrane anchoring. See, e.g., Fuse et al., *Chemical Biology* (2010) 5:701-711. However, at the same time, the moenocinol chain is also credited with poor pharmacokinetic properties and high serum binding of meonomycin, e.g., its absorption upon oral administration is relatively poor. See, e.g., van Heijenoort, *Glycobiology* (2001) 11:25R-36R.

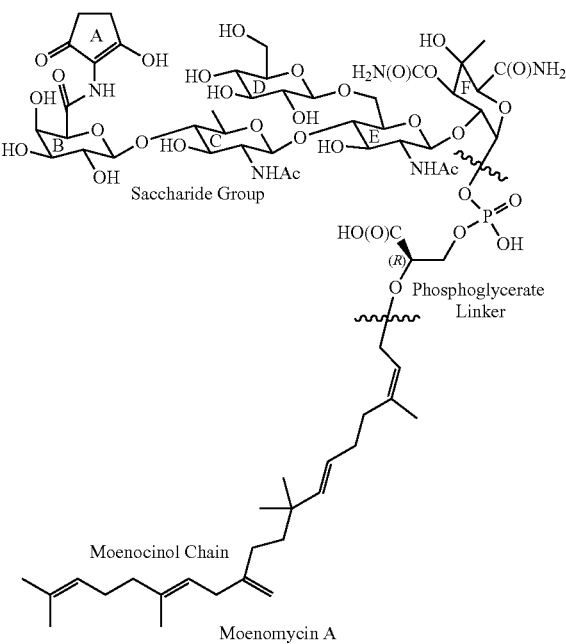

SUMMARY OF THE INVENTION

Previous work established that, although $C_{10}$ analogues of the moenocinol chain are too short to retain biological activity, the $C_{25}$ moenocinol chain of Moenomycin A is longer than required for activity. See, e.g., Ostash et al., *Biochemistry* (2009) 48:8830-8841. The inventors evaluated groups of intermediate length, structure, and hydrophobicity, e.g., $C_{15}$-farnesyl, in an effort to explore the structure activity relationship (SAR) of the moenocinol chain. See, e.g., PCT Application Publication No. WO 2009/046314, incorporated herein by reference. The inventors now believe that groups with lengths greater than $C_{15}$-farnesyl, chains substituted with halogen atoms, and chains comprising multiple aryl moieties, will provide increasingly more potent anti-bacterial compounds.

Thus, in one aspect, provided is a moenomycin A analog wherein the moenocinol chain is replaced with a group G, e.g., of the Formula (I),

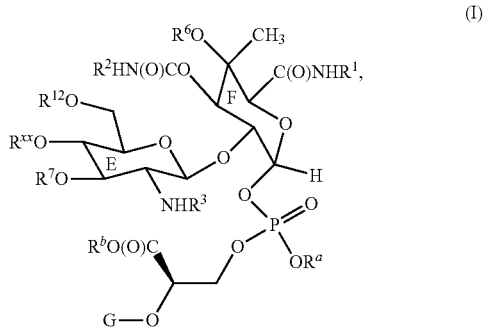

or a pharmaceutically acceptable form thereof;
wherein Rings A, B, C and D of moenomycin A are optionally present, e.g., wherein $R^{XX}$ is hydrogen, a hydroxyl protecting group, or a group of Formula:

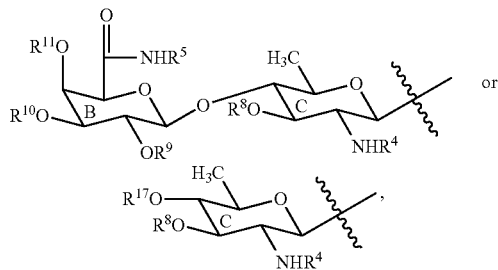

and $R^{12}$ is hydrogen, a hydroxyl protecting group, or the group (D):

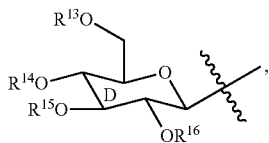

and wherein G is a group of Formula (a), (b), or (c):

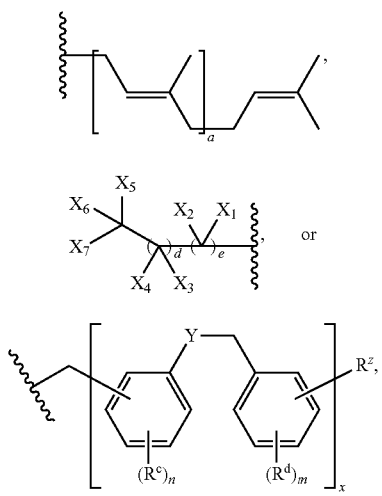

wherein:
a is 3, 4, or 5;
$X_1$, $X_2$, $X_3$, $X_4$, $X_5$, $X_6$, and $X_7$ are each independently hydrogen or halogen;
d is an integer between 1 and 25, inclusive;
e is an integer of between 2 and 25, inclusive;
provided the sum of d and e is greater than 16;
Y is —O—, —S—, —NR$^Y$—, or an optionally substituted methylene group, wherein R$^Y$ is hydrogen, optionally substituted aliphatic, or an amino protecting group;
each instance of R$^c$ is independently —F, —Br, —I, —Cl, optionally substituted aliphatic, optionally substituted heteroaliphatic, optionally substituted carbocycyl, optionally substituted heterocycyl, optionally substituted aryl, optionally substituted heteroaryl, —OR$^e$, —SR$^e$, —NHR$^e$, or —N(R$^e$)$_2$, wherein each instance of R$^e$ is independently hydrogen, optionally substituted aliphatic, optionally substituted heteroaliphatic, optionally substituted carbocycyl, optionally substituted heterocycyl, optionally substituted aryl, or optionally substituted heteroaryl, or two R$^e$ groups are joined to form a 5- to 6-membered optionally substituted heterocycyl or optionally substituted heteroaryl ring;
each instance of R$^d$ is independently —F, —Br, —I, —Cl, optionally substituted aliphatic, optionally substituted heteroaliphatic, optionally substituted carbocycyl, optionally substituted heterocycyl, optionally substituted aryl, optionally substituted heteroaryl, —OR$^f$, —SR$^f$, —NHR$^f$, or —N(R$^f$)$_2$, wherein each instance of R$^f$ is independently hydrogen, optionally substituted aliphatic, optionally substituted heteroaliphatic, optionally substituted carbocycyl, optionally substituted heterocycyl, optionally substituted aryl, or optionally substituted heteroaryl, or two R$^f$ groups are joined to form a 5- to 6-membered optionally substituted heterocycyl or optionally substituted heteroaryl ring;
R$^z$ is hydrogen, —F, —Br, —I, —Cl, optionally substituted aliphatic, optionally substituted heteroaliphatic, optionally substituted carbocycyl, optionally substituted heterocycyl, optionally substituted aryl, optionally substituted heteroaryl, —OR$^g$, —SR$^g$, —NHR$^g$, or —N(R$^g$)$_2$, wherein each instance of R$^g$ is independently hydrogen, optionally substituted aliphatic, optionally substituted heteroaliphatic, optionally substituted carbocycyl, optionally substituted heterocycyl, optionally substituted aryl, or optionally substituted heteroaryl or two R$^g$ groups are joined to form a 5- to 6-membered optionally substituted heterocycyl or optionally substituted heteroaryl ring;
each instance of n is, independently, 0, 1, 2, 3, or 4;
each instance of m is, independently, 0, 1, 2, 3, or 4; and
x is 1, 2, 3, 4, 5, or 6;
wherein R$^1$, R$^2$, R$^3$, R$^4$, R$^5$, R$^6$, R$^7$, R$^8$, R$^9$, R$^{10}$, R$^{11}$, R$^{13}$, R$^{14}$, R$^{15}$, R$^{16}$, R$^{17}$, R$^a$, and R$^b$ are as defined herein.
For example, in one embodiment of Formula (I), provided is a compound of Formula (II):

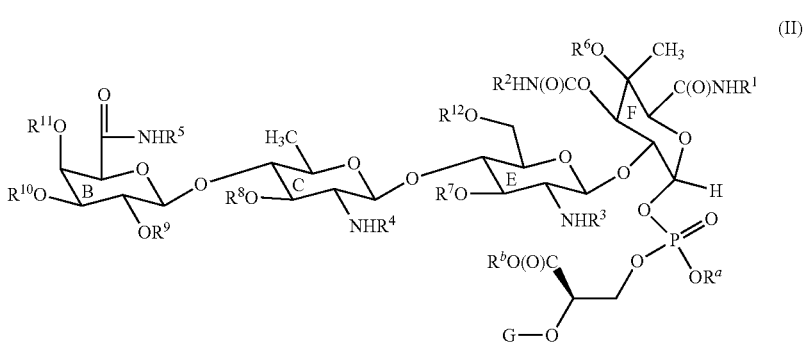

or a pharmaceutically acceptable form thereof; wherein $R^1$, $R^2$, $R^3$, $R^4$, $R^5$, $R^6$, $R^7$, $R^8$, $R^9$, $R^{10}$, $R^{11}$, $R^{12}$, $R^a$, and $R^b$ are as defined herein, and G is a group of Formula (a), (b), or (c) as defined herein.

In another embodiment of Formula (I), provided is a compound of Formula (III):

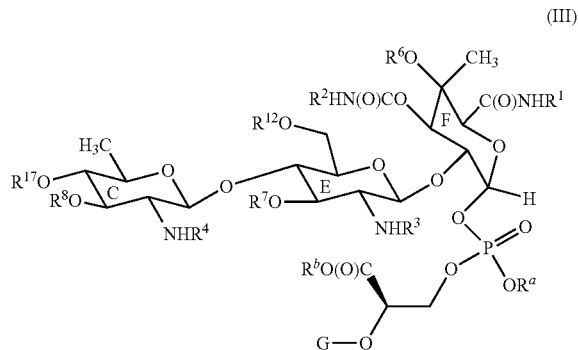

(III)

or a pharmaceutically acceptable form thereof; wherein $R^1$, $R^2$, $R^3$, $R^4$, $R^5$, $R^6$, $R^7$, $R^8$, $R^{12}$, $R^{17}$, $R^a$, and $R^b$ are as defined herein, and G is a group of Formula (a, (b), or (c) as defined herein.

In yet another embodiment of Formula (I), provided is a compound of Formula (IV):

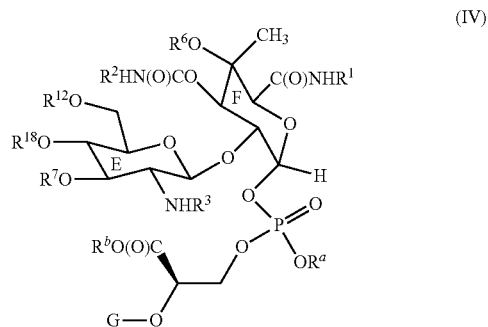

(IV)

or a pharmaceutically acceptable form thereof; wherein $R^1$, $R^2$, $R^3$, $R^6$, $R^7$, $R^{12}$, $R^{18}$, $R^a$, and $R^b$, are as defined herein, and G is a group of Formula (a), (b), or (c) as defined herein.

The present invention further provides pharmaceutical compositions comprising a compound of Formula (I), (II), (III), or (IV), and kits comprising such compositions. The present invention further provides methods of use and treatment, and preparative methods.

The details of one or more embodiments of the invention are set forth in the Detailed Description of Certain Embodiments, as described below. Other features, objects, and advantages of the invention will be apparent from the Definitions, Examples, and Claims.

DEFINITIONS

Definitions of specific functional groups and chemical terms are described in more detail below. For purposes of this invention, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March March's Advanced Organic Chemistry, 5th Edition, John Wiley & Sons, Inc., New York, 2001; Larock, Comprehensive Organic Transformations, VCH Publishers, Inc., New York, 1989; Carruthers, Some Modern Methods of Organic Synthesis, 3rd Edition, Cambridge University Press, Cambridge, 1987; the entire contents of each of which are incorporated herein by reference.

The compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Where an isomer/enantiomer is preferred, it may, in some embodiments, be provided substantially free of the corresponding enantiomer, and may also be referred to as "optically enriched." "Optically enriched," as used herein, means that the compound is made up of a significantly greater proportion of one enantiomer. In certain embodiments the compound of the present invention is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques, et al., Enantiomers, Racemates and Resolutions (Wiley Interscience, New York, 1981); Wilen, S. H., et al., Tetrahedron 33:2725 (1977); Eliel, E. L. Stereochemistry of Carbon Compounds (McGraw-Hill, NY, 1962); Wilen, S. H. Tables of Resolving Agents and Optical Resolutions p. 268 (E. L. Eliel, Ed., Univ. of Notre Dame Press, Notre Dame, Ind. 1972).

When a range of values is listed, it is intended to encompass each value and sub-range within the range. For example, an "alkyl group having from 1 to 6 carbons" (also referred to herein as "$C_{1-6}$ alkyl") is intended to encompass 1 ($C_1$ alkyl), 2 ($C_2$ alkyl), 3 ($C_3$ alkyl), 4 ($C_4$ alkyl), 5 ($C_5$ alkyl) and 6 ($C_6$ alkyl) carbons, and a range of 1 to 6 ($C_{1-6}$ alkyl), 1 to 5 ($C_{1-5}$ alkyl), 1 to 4 ($C_{1-4}$ alkyl), 1 to 3 ($C_{1-3}$ alkyl), 1 to 2 ($C_{1-2}$ alkyl), 2 to 6 ($C_{2-6}$ alkyl), 2 to 5 ($C_{2-5}$ alkyl), 2 to 4 ($C_{2-4}$ alkyl), 2 to 3 ($C_{2-3}$ alkyl), 3 to 6 ($C_{3-6}$ alkyl), 3 to 5 ($C_{3-5}$ alkyl), 3 to 4 ($C_{3-4}$ alkyl), 4 to 6 ($C_{4-6}$ alkyl), 4 to 5 ($C_{4-5}$ alkyl), and 5 to 6 ($C_{5-6}$ alkyl) carbons.

The term "aliphatic," as used herein, refers to a monoradical of a non-aromatic, saturated or unsaturated, unbranched ("straight-chain") or branched, substituted or unsubstituted, acyclic hydrocarbon having 1-50 carbon atoms (i.e., $C_{1-50}$ aliphatic). Thus, as used herein, the term "aliphatic" encompasses the groups "alkyl", "alkynyl", and "alkenyl" as defined herein. In certain embodiments, aliphatic refers to a $C_2$-$C_{30}$ aliphatic group. In certain embodiments, aliphatic refers to a $C_5$-$C_{25}$ aliphatic group. In certain embodiments, aliphatic refers to a $C_1$-$C_{10}$ aliphatic group. In certain embodiments, aliphatic refers to a $C_{10}$-$C_{20}$ aliphatic group. In certain embodiments, aliphatic refers to a $C_{11}$-$C_{15}$ aliphatic group. Unless otherwise specified, each instance of aliphatic is independently unsubstituted ("unsubstituted aliphatic") or substituted ("substituted aliphatic") with 1, 2, 3, 4, 5, 6, 7, 8, 9, 10, or more substituents as described herein. Aliphatic group substituents include, but are not limited to, any of the monovalent or divalent substituents described herein, that result in the formation of a stable moiety.

The term "alkyl," as used herein, refers to a monoradical of a nonaromatic, saturated, unbranched ("straight-chain") or branched, substituted or unsubstituted, acyclic hydrocarbon having 1-50 carbon atoms (i.e., $C_{1-50}$ alkyl). In certain embodiments, alkyl refers to a $C_2$-$C_{30}$ alkyl group. In certain embodiments, alkyl refers to a $C_5$-$C_{25}$ alkyl group. In certain embodiments, alkyl refers to a $C_{10}$-$C_{20}$ alkyl group. In certain embodiments, alkyl refers to a $C_1$-$C_{10}$ alkyl group. In certain embodiments, alkyl refers to a $C_{11}$-$C_{15}$ alkyl group. Exemplary alkyl groups include, without limitation, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, tridecyl, tetradecyl, pentadecyl, hexadecyl, heptadecyl, octadecyl, nonadecyl, eicosyl, and the like, which may bear one or more substituents. Unless otherwise specified, each instance of alkyl is independently unsubstituted ("unsubstituted alkyl") or substituted ("substituted alkyl") with 1, 2, 3, 4, 5, 6, 7, 8, 9, 10, or more substituents as described herein. Alkyl group substituents include, but are not limited to, any of the monovalent or divalent substituents described herein, that result in the formation of a stable moiety.

"Methylene" refers to a divalent $C_1$-alkyl group as defined herein.

The term "fluoroalkyl," as used herein, refers to an alkyl group having from 1 to 50 carbon atoms wherein at least one hydrogen is replaced with a fluorine atom ("$C_{1-50}$ fluoroalkyl"). In certain embodiments, the fluoroalkyl group has 1 to 8 carbon atoms ("$C_{1-8}$ fluoroalkyl"). In certain embodiments, the fluoroalkyl group has 1 to 6 carbon atoms ("$C_{1-6}$ fluoroalkyl"). In certain embodiments, the fluoroalkyl group has 1 to 4 carbon atoms ("$C_{1-4}$ fluoroalkyl"). In certain embodiments, the fluoroalkyl group has 1 to 3 carbon atoms ("$C_{1-3}$ fluoroalkyl"). In certain embodiments, the fluoroalkyl group has 1 to 2 carbon atoms ("$C_{1-2}$ fluoroalkyl"). In certain embodiments, one hydrogen atom is replaced with a fluorine atom. In certain embodiments, two hydrogen atoms are replaced with fluorine atoms. In certain embodiments, three hydrogen atoms are replaced with fluorine atoms. In certain embodiments, four hydrogen atoms are replaced with fluorine atoms. In certain embodiments, five hydrogen atoms are replaced with fluorine atoms. In certain embodiments, all of the hydrogen atoms are replaced with fluorine atoms (also referred to as a "perfluoroalkyl" group). Exemplary fluoroalkyl groups include, but are not limited to, —$CH_2F$, —$CF_2H$, —$CF_3$, —$CH_2CF_3$, —$CF_2CF_3$, —$CH_2CH_2CF_3$, —$CH_2CF_2CF_3$, —$CF_2CF_2CF_3$, and the like.

The term "alkenyl," as used herein, refers to a monoradical of a nonaromatic, unbranched ("straight-chain") or branched, substituted or unsubstituted, acyclic hydrocarbon having at least one carbon-carbon double bond, having zero carbon-carbon triple bonds, and having 2-50 carbon atoms (i.e., $C_{2-50}$ alkenyl). In certain embodiments, alkenyl refers to a $C_5$-$C_{25}$ alkenyl group. In certain embodiments, alkenyl refers to a $C_{10}$-$C_{20}$ alkenyl group. In certain embodiments, alkenyl refers to a $C_2$-$C_{10}$ alkenyl group. In certain embodiments, alkenyl refers to a $C_{11}$-$C_{15}$ alkenyl group. Exemplary alkenyl groups include, without limitation, ethenyl, propenyl, butenyl, 1-methyl-2-buten-1-yl, and the like, which may bear one or more substituents. Unless otherwise specified, each instance of alkenyl is independently unsubstituted ("unsubstituted alkenyl") or substituted ("substituted alkenyl") with 1, 2, 3, 4, 5, 6, 7, 8, 9, 10, or more substituents as described herein. Alkenyl group substituents include, but are not limited to, any of the monovalent or divalent substituents described herein, that result in the formation of a stable moiety.

The term "alkynyl," as used herein, refers to a monoradical of a nonaromatic, unbranched ("straight-chain") or branched, substituted or unsubstituted, acyclic hydrocarbon having at least one carbon-carbon triple bond, optionally containing one or more carbon-carbon double bonds, and having 2-50 carbon atoms (i.e., $C_{2-50}$ alkynyl). In certain embodiments, alkynyl refers to a $C_5$-$C_{25}$ alkynyl group. In certain embodiments, alkynyl refers to a $C_2$-$C_{10}$ alkynyl group. In certain embodiments, alkynyl refers to a $C_{10}$-$C_{20}$ alkynyl group. In certain embodiments, alkynyl refers to a $C_{11}$-$C_{15}$ alkynyl group. Exemplary alkynyl groups include, without limitation, ethynyl, 2-propynyl(propargyl), 1-propynyl, and the like, which may bear one or more substituents. Unless otherwise specified, each instance of alkynyl is independently unsubstituted ("unsubstituted alkynyl") or substituted ("substituted alkynyl") with 1, 2, 3, 4, 5, 6, 7, 8, 9, 10, or more substituents as described herein. Alkynyl group substituents include, but are not limited to, any of the monovalent or divalent substituents described herein, that result in the formation of a stable moiety.

The term "heteroaliphatic," as used herein, refers to a $C_{1-50}$ aliphatic group wherein one, two or three methylene units of the hydrocarbon chain are independently replaced with one or more oxygen, sulfur or nitrogen atoms. Thus, as used herein, the term "heteroaliphatic" encompasses the groups "heteroalkyl", "heteroalkynyl", and "heteroalkenyl" as defined herein. Unless otherwise specified, each instance of heteroaliphatic is independently unsubstituted ("unsubstituted heteroaliphatic") or substituted ("substituted heteroaliphatic") with 1, 2, 3, 4, 5, 6, 7, 8, 9, 10, or more substituents as described herein. Heteroaliphatic group substituents include, but are not limited to, any of the monovalent or divalent substituents described herein, that result in the formation of a stable moiety.

The term "heteroalkyl," as used herein, refers to a $C_{1-50}$ alkyl group wherein one, two or three methylene units of the hydrocarbon chain are independently replaced with one or more oxygen, sulfur or nitrogen atoms. Unless otherwise specified, each instance of heteroalkyl is independently unsubstituted ("unsubstituted heteroalkyl") or substituted ("substituted heteroalkyl") with 1, 2, 3, 4, 5, 6, 7, 8, 9, 10, or more substituents as described herein. Heteroalkyl group substituents include, but are not limited to, any of the monovalent or divalent substituents described herein, that result in the formation of a stable moiety.

The term "heteroalkenyl," as used herein, refers to a $C_{2-50}$ alkenyl group wherein one, two or three methylene units of the hydrocarbon chain are independently replaced with one or more oxygen, sulfur or nitrogen atoms. Unless otherwise specified, each instance of heteroalkenyl is independently unsubstituted ("unsubstituted heteroalkenyl") or substituted ("substituted heteroalkenyl") with 1, 2, 3, 4, 5, 6, 7, 8, 9, 10, or more substituents as described herein. Heteroalkenyl group substituents include, but are not limited to, any of the monovalent or divalent substituents described herein, that result in the formation of a stable moiety.

The term "heteroalkynyl," as used herein, refers to a $C_{2-50}$ alkynyl group wherein one, two or three methylene units of the hydrocarbon chain are independently replaced with one or more oxygen, sulfur or nitrogen atoms. Unless otherwise specified, each instance of heteroalkynyl is independently unsubstituted ("unsubstituted heteroalkynyl") or substituted ("substituted heteroalkynyl") with 1, 2, 3, 4, 5, 6, 7, 8, 9, 10, or more substituents as described herein. Heteroalkynyl group substituents include, but are not limited to, any of the monovalent or divalent substituents described herein, that result in the formation of a stable moiety.

The terms "carbocyclic" or "carbocyclyl," as used herein, refer to a monoradical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$) and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$) and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups, as defined herein, wherein the point of attachment is on the carbocyclyl ring; in such instances, the number of carbons continues to designate the number of carbons in the carbocyclic ring system. Unless otherwise specified, each instance of a carbocyclyl group is independently unsubstituted ("unsubstituted carbocyclyl") or substituted ("substituted carbocyclyl") with 1, 2, 3, 4, 5, 6, 7, 8, 9, 10, or more substituents as described herein. Carbocyclyl group substituents include, but are not limited to, any of the monovalent or divalent substituents described herein, that result in the formation of a stable moiety.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Exemplary $C_{5-6}$ cycloalkyl groups include, without limitation, cyclopentyl ($C_5$) and cyclohexyl ($C_5$). Exemplary $C_{3-6}$ cycloalkyl groups include, without limitation, the aforementioned $C_{5-6}$ cycloalkyl groups as well as cyclopropyl ($C_3$) and cyclobutyl ($C_4$). Exemplary $C_{3-8}$ cycloalkyl groups include, without limitation, the aforementioned $C_{3-6}$ cycloalkyl groups as well as cycloheptyl ($C_7$) and cyclooctyl ($C_8$). Unless otherwise specified, each instance of a cycloalkyl group is independently unsubstituted ("unsubstituted cycloalkyl") or substituted ("substituted cycloalkyl") with 1, 2, 3, 4, 5, 6, 7, 8, 9, 10, or more substituents as described herein. Cycloalkyl group substituents include, but are not limited to, any of the monovalent or divalent substituents described herein, that result in the formation of a stable moiety.

The terms "heterocyclic" or "heterocyclyl," as used herein, refer to a radical of a 3- to 14-membered nonaromatic ring system having ring carbon atoms and 1 to 4 ring heteroatoms, wherein each heteroatom is independently selected from the group consisting of nitrogen, oxygen and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" includes ring systems wherein the heterocycyl ring, as defined above, is fused with one or more carbocycyl groups wherein the point of attachment is either on the carbocycyl or heterocyclyl ring; in such instances, the number of ring members continues to designate the number of ring members in the heterocyclyl ring system. Heterocycyl also includes ring systems wherein the heterocyclyl ring, as defined above, is fused with one or more aryl or heteroaryl groups, wherein the point of attachment is on the heterocyclyl ring; in such instances, the number of ring members continues to designate the number of ring members in the heterocyclyl ring system. In some embodiments, a heterocyclyl group is a 5-10 membered nonaromatic ring system having ring carbon atoms and 1-4 ring heteroatoms, wherein each heteroatom is independently selected from the group consisting of nitrogen, oxygen and sulfur ("5-10 membered heterocyclyl"). In some embodiments, a heterocyclyl group is a 5-8 membered nonaromatic ring system having ring carbon atoms and 1-4 ring heteroatoms, wherein each heteroatom is independently selected from the group consisting of nitrogen, oxygen and sulfur ("5-8 membered heterocyclyl"). In some embodiments, a heterocyclyl group is a 5-6 membered nonaromatic ring system having ring carbon atoms and 1-4 ring heteroatoms, wherein each heteroatom is independently selected from the group consisting of nitrogen, oxygen and sulfur ("5-6 membered heterocyclyl"). In some embodiments, the 5-6 membered heterocyclyl has 1-3 ring heteroatoms selected from the group consisting of nitrogen, oxygen and sulfur. In some embodiments, the 5-6 membered heterocyclyl has 1-2 ring heteroatoms selected from the group consisting of nitrogen, oxygen and sulfur. In some embodiments, the 5-6 membered heterocyclyl has 1 ring heteroatom selected from the group consisting of nitrogen, oxygen and sulfur. Exemplary 3-membered heterocyclyls containing 1 heteroatom include, without limitation, azirdinyl, oxiranyl, thiorenyl. Exemplary 4-membered heterocyclyls containing 1 heteroatom include, without limitation, azetidinyl, oxetanyl and thietanyl. Exemplary 5-membered heterocyclyls containing 1 heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyls containing 2 heteroatoms include, without limitation, dioxolanyl, oxathiolanyl and dithiolanyl. Exemplary 5-membered heterocyclyls containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo-[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like. Unless otherwise specified, each instance of heterocyclyl is independently unsubstituted ("unsubstituted heterocyclyl") or substituted ("substituted heterocyclyl") with 1, 2, 3, 4, 5, 6, 7, 8, 9, 10, or more substituents as described herein. Heterocyclyl group substituents include, but are not limited to, any of the monovalent or divalent substituents described herein, that result in the formation of a stable moiety.

The term "aryl," as used herein, refers to a radical of a monocyclic or polycyclic (e.g., bicyclic or tricyclic) aromatic ring system (e.g., having 6, 10 or 14π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring; in such instances, the number of carbon atoms continues to designate the number of carbon atoms in the aryl ring system. Unless otherwise specified, each instance of an aryl group is independently unsubstituted ("unsubstituted aryl") or substituted ("substituted aryl") with 1, 2, 3, 4, 5, 6, 7, 8, 9, 10, or more substituents as described herein. Aryl group substituents include, but are not limited to, any of the monovalent substituents described herein, that result in the formation of a stable moiety.

The terms "aralkyl" or "arylalkyl" are a subset of "alkyl" and refer to an alkyl group, as defined herein, substituted by an aryl group, as defined herein, wherein the point of attachment is on the alkyl moiety.

The term "heteroaryl," as used herein, refers to a radical of a 5-14 membered monocyclic or polycyclic (e.g., bicyclic or tricyclic) aromatic ring system (e.g., having 6, 10 or 14π electrons shared in a cyclic array) having ring carbon atoms and 1-4 ring heteroatoms provided in the aromatic ring system, wherein each heteroatom is independently selected from the group consisting of nitrogen, oxygen and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocycyl or heterocycyl groups wherein the point of attachment is on the heteroaryl ring; in such instances, the number of ring members continues to designate the number of ring members in the heteroaryl ring system. "Heteroaryl" also includes ring systems wherein the heteroaryl ring, as defined above, is fused with one or more aryl groups wherein the point of attachment is either on the aryl or on the heteroaryl ring; in such instances, the number of ring members designates the number of ring members in the fused polycyclic (arylheteroaryl) ring system. For example, polycyclic heteroaryl groups wherein one ring does not contain a heteroatom (e.g., indolyl, quinolinyl, carbazolyl and the like) the point of attachment can be on either ring, i.e., either the ring bearing a heteroatom (e.g., 2-indolyl) or the ring that does not contain a heteroatom (e.g., 5-indolyl). In some embodiments, a heteroaryl group is a 5-10 membered aromatic ring system having ring carbon atoms and 1-4 ring heteroatoms provided in the aromatic ring system, wherein each heteroatom is independently selected from the group consisting of nitrogen, oxygen and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from the group consisting of nitrogen, oxygen and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from the group consisting of nitrogen, oxygen and sulfur ("5-6 membered heteroaryl"). In some embodiments, the 5-6 membered heteroaryl has 1-3 ring heteroatoms selected from the group consisting of nitrogen, oxygen and sulfur. In some embodiments, the 5-6 membered heteroaryl has 1-2 ring heteroatoms selected from the group consisting of nitrogen, oxygen and sulfur. In some embodiments, the 5-6 membered heteroaryl has 1 ring heteroatom selected from the group consisting of nitrogen, oxygen and sulfur. Exemplary 5-membered heteroaryls containing 1 heteroatom include, without limitation, pyrrolyl, furanyl and thiophenyl. Exemplary 5-membered heteroaryls containing 2 heteroatoms include, without limitation, imidazolyl, pyrazolyl, oxazolyl, isoxazolyl, thiazolyl, and isothiazolyl. Exemplary 5-membered heteroaryls containing 3 heteroatoms include, without limitation, triazolyl, oxadiazolyl, thiadiazolyl. Exemplary 5-membered heteroaryls containing 4 heteroatoms include, without limitation, tetrazolyl. Exemplary 6-membered heteroaryls containing 1 heteroatom include, without limitation, pyridinyl. Exemplary 6-membered heteroaryls containing 2 heteroatoms include, without limitation, pyridazinyl, pyrimidinyl and pyrazinyl. Exemplary 6-membered heteroaryls containing 3 or 4 heteroatoms include, without limitation, triazinyl and tetrazinyl, respectively. Exemplary 7 membered heteroaryls containing 1 heteroatom include, without limitation, azepinyl, oxepinyl and thiepinyl. Exemplary 5,6-bicyclic heteroaryls include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryls include, without limitation, naphthyridinyl, pteridinyl, quinolinyl, isoquinolinyl, cinnolinyl, quinoxalinyl, phthalazinyl and quinazolinyl. Exemplary tricyclic heteroaryls include, without limitation, phenanthridinyl, dibenzofuranyl, carbazolyl, acridinyl, phenothiazinyl, phenoxazinyl and phenazinyl. Unless otherwise specified, each instance of a heteroaryl group is independently unsubstituted ("unsubstituted heteroaryl") or substituted ("substituted heteroaryl") 1, 2, 3, 4, 5, 6, 7, 8, 9, 10, or more substituents as described herein. Heteroaryl group substituents include, but are not limited to, any of the monovalent substituents described herein, that result in the formation of a stable moiety.

The terms "heteroarylalkyl" or "heteroaralkyl" are a subset of "alkyl" and refer to an alkyl group, as defined herein, substituted by a heteroaryl group, as defined herein, wherein the point of attachment is on the alkyl moiety.

As used herein, the term "partially unsaturated" refers to a ring moiety that includes at least one double or triple bond. The term "partially unsaturated" is intended to encompass rings having multiple sites of unsaturation, but is not intended to include aromatic groups (e.g., aryl or heteroaryl moieties) as defined herein.

Unless otherwise specified, aliphatic (e.g., alkyl, alkenyl, alkynyl), heteroaliphatic (e.g., heteroalkyl, heteroalkenyl, heteroalkynyl), carbocyclyl, heterocyclyl, aryl and heteroaryl groups, as defined herein, are optionally substituted (e.g., "substituted" or "unsubstituted" aliphatic, "substituted" or "unsubstituted" alkyl, "substituted" or "unsubstituted" alkenyl, "substituted" or "unsubstituted" alkynyl, "substituted" or "unsubstituted" heteroaliphatic, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl, or "substituted" or "unsubstituted" heteroaryl group). In general, the term "substituted" means that at least one hydrogen present on a group (e.g., a carbon or nitrogen atom etc.) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position.

Exemplary monovalent carbon atoms substituents include, but are not limited to, halo/halogen (i.e., —F, —Br, —Cl, —I), —NC, —CN, —NO$_2$, —N$_3$, —CO$_2$H, —CHO, —SO$_2$H, —SO$_3$H, —S(=O)OH, acyl (e.g., —C(=O)R$^A$, —CO$_2$R$^A$, —C(=O)—O—C(=O)R$^A$, —C(=O)SR$^A$, —C(=O)N(R$^B$)$_2$, —C(=O)NR$^B$SO$_2$R$^A$, —C(=NR$^B$)R$^A$, —C(=NR$^B$)OR$^A$, —C(=NR$^B$)N(R$^B$)$_2$, —C(=S)R$^A$, —C(=S)N(R$^A$)$_2$, —C(=S)SR$^A$), amino (e.g., —NH$_2$, —N(OR$^B$)R$^B$, —N(R$^B$)$_2$, —NR$^B$SO$_2$R$^A$, —NR$^B$C(=O)R$^A$, —NR$^B$CO$_2$R$^A$, —NR$^B$C(=O)N(R$^B$)$_2$, —NR$^B$C(=NR$^B$)N(R$^B$)$_2$), thio (e.g., —SH, —SR$^A$, —SSR$^B$), oxy (e.g., —OH, —OR$^A$, —ON(R$^B$)$_2$, —OSO$_2$R$^A$, —OS(=O)R$^A$, —OC(=O)R$^A$, —OCO$_2$R$^A$, —OC(=O)N(R$^B$)$_2$, —OC(=NR$^B$)R$^A$, —OC(=NR$^B$)OR$^A$, —OC(=NR$^B$)N(R$^B$)$_2$), sulfonyl (e.g., —SO$_2$R$^A$, —SO$_2$OR$^A$, —SO$_2$N(R$^B$)$_2$), sulfinyl (e.g., —S(=O)R$^A$), silyl (e.g., —Si(R$^A$)$_3$), C$_{1-10}$ alkyl, C$_{1-10}$ fluoroalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each aliphatic, heteroaliphatic, carbocyclyl, heterocyclyl, aryl, and heteroaryl is independently substituted with 0, 1, 2, 3, 4, or 5 R$^D$ groups;

each instance of R$^A$ is, independently, selected from the group consisting of C$_{1-10}$ alkyl, C$_{1-10}$ fluoroalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each aliphatic, heteroaliphatic, carbocyclyl, heterocyclyl, aryl, and heteroaryl is independently substituted with 0, 1, 2, 3, 4, or 5 R$^D$ groups;

each instance of R$^B$ is, independently, selected from the group consisting of hydrogen, —OH, —OR$^A$, —N(R$^C$)$_2$, —CN, —C(=O)R$^A$, —C(=O)N(R$^C$)$_2$, —CO$_2$R$^A$, —SO$_2$R$^A$, —C(=NR$^C$)OR$^A$, —C(=NR$^C$)N(R$^C$)$_2$, —SO$_2$N(R$^C$)$_2$, —SO$_2$R$^C$, —SO$_2$OR$^C$, —SOR$^A$, —C(=S)N(R$^C$)$_2$, —C(=O)SR$^C$, —C(=S)SR$^C$, C$_{1-10}$ alkyl, C$_{1-10}$ fluoroalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^B$ groups attached to an N atom are joined to form a 3-14 membered heterocyclyl or 5-14 membered heteroaryl ring, wherein each aliphatic, heteroaliphatic, carbocyclyl, heterocyclyl, aryl, and heteroaryl is independently substituted with 0, 1, 2, 3, 4, or 5 R$^D$ groups;

each instance of R$^C$ is, independently, selected from the group consisting of hydrogen, C$_{1-10}$ alkyl, C$_{1-10}$ fluoroalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^C$ groups attached to an N atom are joined to form a 3-14 membered heterocyclyl or 5-14 membered heteroaryl ring, wherein each aliphatic, heteroaliphatic, carbocyclyl, heterocyclyl, aryl, and heteroaryl is independently substituted with 0, 1, 2, 3, 4, or 5 R$^D$ groups; and each instance of R$^D$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$alkyl), —OC(=NH)OC$_{1-6}$alkyl, —C(=NH)N(C$_{1-6}$alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —S(=O)C$_{1-6}$ alkyl, C$_{1-6}$ alkyl, C$_{1-6}$ fluoroalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal R$^D$ substituents are joined to form =O, =S or =NR$^B$.

Exemplary divalent carbon atom substituents include, but are not limited to =O, =S, and =NR$^B$, wherein R$^B$ is as defined herein.

Nitrogen atoms can be substituted or unsubstituted as valency permits, and include primary, secondary, tertiary and quarternary nitrogen atoms. Exemplary nitrogen atom substituents include, but are not limited to, =NR$^B$, —CHO, —C(=O)R$^A$, —CO$_2$R$^A$, —C(=O)SR$^A$, —C(=O)N(R$^B$)$_2$, —C(=O)NR$^B$SO$_2$R$^A$, —C(=NR$^B$)R$^A$, —C(=NR$^B$)OR$^A$, —C(=NR$^B$)N(R$^B$)$_2$, —C(=S)R$^A$, —C(=S)N(R$^A$)$_2$, —C(=S)SR$^A$, —NH$_2$, —N(OR$^B$)R$^B$, —N(R$^B$)$_2$, —NR$^B$SO$_2$R$^A$, —NR$^B$C(=O)R$^A$, —NR$^B$CO$_2$R$^A$, —NR$^B$C(=O)N(R$^B$)$_2$, —NR$^B$C(=NR$^B$)N(R$^B$)$_2$, —OH, —OR$^A$, —SO$_2$R$^A$, —SO$_2$OR$^A$, —SO$_2$N(R$^B$)$_2$, —S(=O)R$^A$), —Si(R$^A$)$_3$, C$_{1-10}$ alkyl, C$_{1-10}$ fluoroalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^D$ groups.

In certain embodiments, nitrogen atom substituents, as described above, are also referred to as "amino protecting groups" or "nitrogen protecting groups". Amino protecting groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference.

Exemplary amino protecting groups include, but are not limited to, methyl carbamate, ethyl carbamate, acetyl (—C(═O)CH$_3$, —Ac), 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Exemplary oxygen substituents include, but are not limited to, —C(═O)R$^A$, —CO$_2$R$^A$, —C(═O)—O—C(═O)R$^A$, —C(═O)SR$^A$, —C(═O)N(R$^B$)$_2$, —C(═O)NR$^B$SO$_2$R$^A$, —C(═NR$^B$)R$^A$, —C(═NR$^B$)OR$^A$, —C(═NR$^B$)N(R$^B$)$_2$, —C(═S)R$^A$, —C(═S)N(R$^A$)$_2$, —C(═S)SR$^A$, —SO$_2$R$^A$, —SO$_2$OR$^A$, —SO$_2$N(R$^B$)$_2$, —S(═O)R$^A$, —Si(R$^A$)$_3$, —C$_{1-10}$ alkyl, C$_{1-10}$ fluoroalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 $R^D$ groups.

In certain embodiments, oxygen atom substituents, as described above, are also referred to as "hydroxyl protecting groups" or "oxygen protecting groups". Hydroxyl protecting groups are well known in the art and include those described in detail in *Protecting Groups in Organic Synthesis*, T. W. Greene and P. G. M. Wuts, $3^{rd}$ edition, John Wiley & Sons, 1999, the entirety of which is incorporated herein by reference.

Exemplary hydroxyl protecting groups include, but are not limited to, acetyl (—C(=O)CH$_3$, —Ac), methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri (p-methoxyphenyl)methyl, 4-(4'-bromophenacyloxyphenyl) diphenylmethyl, 4,4',4''-tris(4,5-dichlorophthalimidophenyl) methyl, 4,4',4''-tris(levulinoyloxyphenyl)methyl, 4,4',4''-tris (benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio)ethyl carbonate (Peoc), isobutyl carbonate, vinyl carbonate, allyl carbonate, p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxylnapththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl) phenoxyacetate, chlorodiphenylacetate, isobutyrate, monosuccinoate, (E)-2-methyl-2-butenoate, o-(methoxycarbonyl)benzoate, α-naphthoate, N,N,N',N'-tetramethylphosphorodiamidate, N-phenylcarbamate, dimethylphosphinothioyl, 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl) ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino) ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

The term "pharmaceutically acceptable form thereof" as used herein refers to pharmaceutically acceptable salts, solvates, hydrates, prodrugs, tautomers, isomers, enantiomers, diastereomers, and/or polymorphs of a compound of the present invention.

In certain embodiments, the pharmaceutically acceptable form is a pharmaceutically acceptable salt. The term "pharmaceutically acceptable salt" as used herein refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower-alkyl sulfonate and aryl sulfonate.

In certain embodiments, the pharmaceutically acceptable form is a hydrate or solvate. The term "hydrate" as used herein refers to a compound non-covalently associated with one or more molecules of water. Likewise, the term "solvate" refers to a compound non-covalently associated with one or more molecules of an organic solvent.

In certain embodiments, the pharmaceutically acceptable form is a prodrug. The term "prodrug" as used herein refers to a derivative of a parent compound that requires transformation within the body in order to release the parent compound. In certain cases, a prodrug has improved physical and/or delivery properties over the parent compound. Prodrugs are typically designed to enhance pharmaceutically and/or pharmacokinetically based properties associated with the parent compound. The advantage of a prodrug can lie in its physical properties, such as enhanced water solubility for parenteral administration at physiological pH compared to the parent compound, or it enhances absorption from the digestive tract, or it may enhance drug stability for long-term storage. In recent years several types of bioreversible derivatives have been exploited for utilization in designing prodrugs. Using esters as a prodrug type for compounds containing a carboxyl or hydroxyl functionality is known in the art as described, for example, in *The Organic Chemistry of Drug Design and Drug Interaction* by Richard Silverman, published by Academic Press (1992).

In certain embodiments, the pharmaceutically acceptable form is a tautomer. The term "tautomer" as used herein includes two or more interconvertable compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol; amide-to-imide; lactam-to-lactim; enamine-to-imine; and enamine-to-(a different) enamine tautomerizations.

In certain embodiments, the pharmaceutically acceptable form is an isomer. The term "isomer" as used herein includes any and all geometric isomers and stereoisomers (e.g., enantiomers, diasteromers, etc.). For example, "isomer" include cis- and trans-isomers, E- and Z-isomers, R- and S-enantiomers, diastereomers, (D)-isomers, (L)-isomers, racemic mixtures thereof, and other mixtures thereof, as falling within the scope of the invention. For instance, an isomer/enantiomer may, in some embodiments, be provided substantially free of the corresponding enantiomer, and may also be referred to as "optically enriched." "Optically-enriched," as used herein, means that the compound is made up of a significantly greater proportion of one enantiomer. In certain embodiments the compound of the present invention is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

In certain embodiments, the pharmaceutically acceptable form is a polymorph. The term "polymorph" as used herein refers to a crystalline compound existing in more than one crystalline form/structure. When polymorphism exists as a result of difference in crystal packing it is called packing polymorphism. Polymorphism can also result from the existence of different conformers of the same molecule in conformational polymorphism. In pseudopolymorphism the different crystal types are the result of hydration or solvation.

A "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, and/or turkeys.

As used herein, the terms "treat," "treating" and "treatment" refer to partially or completely halting, reducing, delaying, or diminishing the severity of an infection or symptoms related to an infection from which the subject is suffering.

As used herein, the terms "prevent," "preventing" and "prevention" contemplate an action that occurs before a subject begins to suffer an infection or symptoms related to an infection.

As used herein "inhibition," "inhibiting," and "inhibit", refer to the ability of a compound to reduce, slow, halt or prevent activity of a particular biological process in a cell relative to vehicle. In certain embodiments, the biological process is in vitro (e.g., cellular assay). In certain embodiments, the biological process is in vivo.

As used herein, and unless otherwise specified, an "effective amount" refers to the minimal amount or concentration of an inventive compound or pharmaceutical composition thereof that, when administered, is sufficient in treating or preventing an infection in the subject. In certain embodiments of the present invention an "effective amount" of the inventive compound or pharmaceutical composition thereof is that amount effective for killing, inhibiting, or preventing, the growth of the causative microbial organism (e.g., a bacterium, virus, parasite, or fungus). In certain embodiments, an effective amount is the amount administered to a subject to achieve a concentration at the site of infection sufficient to inhibit the growth of the causative microbial organism. In certain embodiments, an effective amount is the amount administered to a subject to achieve the mean inhibitory concentration at the site of infection for the causative microbial organism.

As used herein, and unless otherwise specified, a "therapeutically effective amount" of a compound is an amount sufficient to provide a therapeutic benefit in the treatment of a infection or to delay or minimize one or more symptoms associated with the infection. A therapeutically effective amount of a compound means an amount of therapeutic agent, alone or in combination with other therapies, which provides a therapeutic benefit in the treatment of the infection. The term "therapeutically effective amount" can encompass an amount that improves overall therapy, reduces or avoids symptoms or causes of infection, or enhances the therapeutic efficacy of another therapeutic agent.

As used herein, and unless otherwise specified, a "prophylactically effective amount" of a compound is an amount sufficient to prevent an infection, or one or more symptoms associated with the infection or prevent its recurrence. A prophylactically effective amount of a compound means an amount of a therapeutic agent, alone or in combination with other agents, which provides a prophylactic benefit in the prevention of the infection. The term "prophylactically effective amount" can encompass an amount that improves overall prophylaxis or enhances the prophylactic efficacy of another prophylactic agent.

As used herein, "infection" refers to a microbial infection (i.e., a bacterial infection, a viral infection, a parasitic infection, or a fungal infection). In certain embodiments, the infection is a bacterial infection.

DETAILED DESCRIPTION OF CERTAIN EMBODIMENTS OF THE INVENTION

Moenomycin A is a natural product that inhibits peptidoglycan biosynthesis by binding to bacterial transglycosylases. Moenomycin A is a thousand times more potent than the antibiotic vancomycin, but poor pharmacokinetic properties related to the lipid side chain have prevented its use in humans. Removal of the natural lipid side chain completely abolishes biological activities. A comprehensive study of the effect of different side chains, optionally in combination with different sugar portions, on the antibacterial activity compared to natural moenomycin A, has been limited as most synthetic tranformations employed in the removal of the natural lipid side chain and in the addition of other different side chains have also altered other structural features of the molecule. Recently, a mild, semi-synthetic, methodology was disclosed which enabled SAR study of new moenomycins; e.g., see PCT Application Publication No. WO 2009/046314, incorporated herein by reference. In the '314 publication, the inventors explored groups of intermediate length and hydrophobicity, e.g., $C_{15}$-farnesyl, in an effort to explore the optimal length for activity and bioavailability. The inventors now believe that groups with lengths greater than $C_{15}$-farnesyl, chains substituted with halogen atoms, and chains comprising multiple aryl moieties, will provide increasingly more potent anti-bacterial compounds.

In particular, the present invention is directed to noenomycin A analogs wherein the moenocinol chain is replaced with a group G, e.g., of the Formula (I),

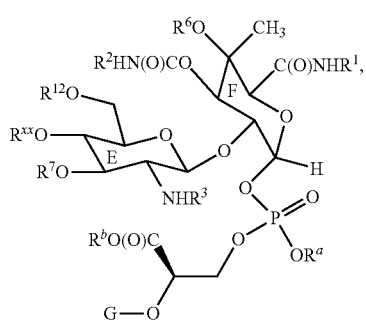

(I)

or a pharmaceutically acceptable form thereof;

wherein Rings A, B, C and D of moenomycin A are optionally present, e.g., wherein $R^{xx}$ is hydrogen, a hydroxyl protecting group, or a group of Formula:

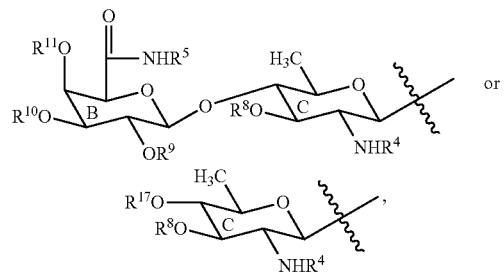

and $R^{12}$ is hydrogen, a hydroxyl protecting group, or the group (D):

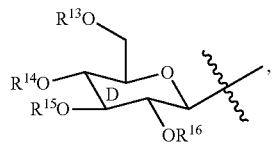

and wherein G is a group of Formula (a), (b), or (C):

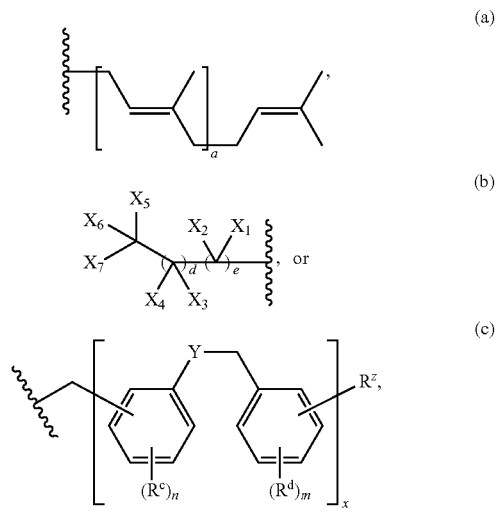

wherein:
a is 3, 4, or 5;
$X_1$, $X_2$, $X_3$, $X_4$, $X_5$, $X_6$, and $X_7$ are each independently hydrogen or halogen;
d is an integer between 1 and 25, inclusive;
e is an integer of between 2 and 25, inclusive;
provided the sum of d and e is greater than 16;
Y is —O—, —S—, —$NR^Y$—, or an optionally substituted methylene group, wherein $R^Y$ is hydrogen, optionally substituted aliphatic, or an amino protecting group;
each instance of $R^c$ is independently —F, —Br, —I, —Cl, optionally substituted aliphatic, optionally substituted heteroaliphatic, optionally substituted carbocycyl, optionally substituted heterocycyl, optionally substituted aryl, optionally substituted heteroaryl, —$OR^e$, —$SR^e$, —$NHR^e$, or —$N(R^e)_2$, wherein each instance of $R^e$ is independently hydrogen, optionally substituted aliphatic, optionally substituted heteroaliphatic, optionally substituted carbocycyl, optionally substituted heterocycyl, optionally substituted aryl, or optionally substituted heteroaryl, or two $R^e$ groups are joined to form a 5- to 6-membered optionally substituted heterocycyl or optionally substituted heteroaryl ring;

each instance of $R^d$ is independently —F, —Br, —I, —Cl, optionally substituted aliphatic, optionally substituted heteroaliphatic, optionally substituted carbocycyl, optionally substituted heterocycyl, optionally substituted aryl, optionally substituted heteroaryl, —$OR^f$, —$SR^f$, —$NHR^f$, or —$N(R^f)_2$, wherein each instance of $R^f$ is independently hydrogen, optionally substituted aliphatic, optionally substituted heteroaliphatic, optionally substituted carbocycyl, optionally substituted heterocycyl, optionally substituted aryl, or optionally substituted heteroaryl, or two $R^f$ groups are joined to form a 5- to 6-membered optionally substituted heterocycyl or optionally substituted heteroaryl ring;

$R^z$ is hydrogen, —F, —Br, —I, —Cl, optionally substituted aliphatic, optionally substituted heteroaliphatic, optionally substituted carbocycyl, optionally substituted heterocycyl, optionally substituted aryl, optionally substituted heteroaryl, —$OR^g$, —$SR^g$, —$NHR^g$, or —$N(R^g)_2$, wherein each instance of $R^g$ is independently hydrogen, optionally substituted aliphatic, optionally substituted heteroaliphatic, optionally substituted carbocycyl, optionally substituted heterocycyl, optionally substituted aryl, or optionally substituted heteroaryl or two $R^g$ groups are joined to form a 5- to 6-membered optionally substituted heterocycyl or optionally substituted heteroaryl ring;

each instance of n is, independently, 0, 1, 2, 3, or 4;
each instance of m is, independently, 0, 1, 2, 3, or 4; and
x is 1, 2, 3, 4, 5, or 6;
and wherein $R^1$, $R^2$, $R^3$, $R^4R^5$, $R^6$, $R^7$, $R^8$, $R^9$, $R^{10}$, $R^{11}$, $R^{13}$, $R^{14}$, $R^{15}$, $R^{16}$, $R^{17}$, $R^a$, and $R^b$ are as defined herein.

In certain embodiments, the present invention provides compounds wherein the sugar portion comprising Rings C, E and F, and optionally Rings A, B, and D, is derived from moenomycin A. In certain embodiments, Rings A, B and/or D are enzymatically or chemically cleaved to provide such compounds. In other embodiments, intermediate moenomycin-like compounds (e.g., without Rings A, B, and/or D) are generated from bacteria (e.g., wild type or genetically engineered bacteria) and further sythetically modified to provide compounds of the present invention.

Compounds encompassed by the present invention, e.g., compounds of the Formula (II), (III), and (IV), are described in more detail herein.

Compounds of Formula (II)

The present invention further provides compounds of Formula (II), as provided below, which include compounds comprising Rings B, C, E and F, and optionally Rings A and D, of the moenomycin A sugar scaffold.

In one aspect, the present invention provides a compound of Formula (II):

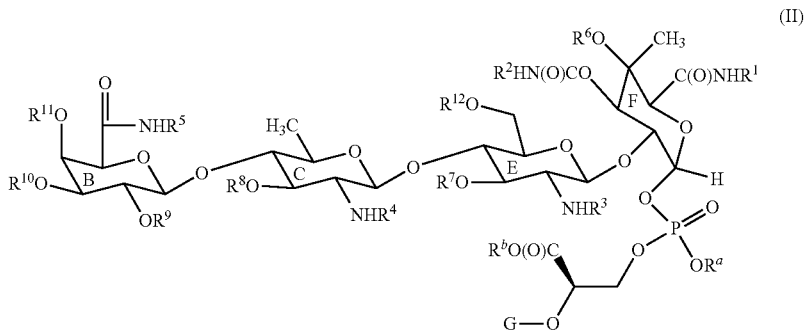

or a pharmaceutically acceptable form thereof;
wherein:
$R^1$, $R^2$, $R^3$, and $R^4$ are each independently hydrogen or an amino protecting group;
$R^5$ is hydrogen, an amino protecting group, or the group (A):

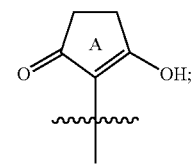

$R^6$, $R^7$, $R^8$, $R^9$, $R^{10}$, and $R^{11}$ are each independently hydrogen or a hydroxyl protecting group;
$R^{12}$ is hydrogen, a hydroxyl protecting group, or the group (D):

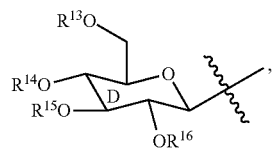

wherein $R^{13}$, $R^{14}$, $R^{15}$, and $R^{16}$ are each independently hydrogen or a hydroxyl protecting group;
$R^a$ and $R^b$ are each independently hydrogen or a hydroxyl protecting group; and wherein G is a group of Formula (a), (b), or (c) as defined herein.

As generally defined above, $R^1$, $R^2$, $R^3$, and $R^4$ are each independently hydrogen or an amino protecting group Amino protecting groups are defined herein, and include, but are not limited to, —CHO, —C(=O)$R^A$, —$CO_2R^A$, —C(=O)$SR^A$, —C(=O)N($R^B$)$_2$, —C(=O)N$R^B$SO$_2R^A$, —C(=NR$^B$)$R^A$, —C(=NR$^B$)OR$^A$, —C(=NR$^B$)N(R$^B$)$_2$, —C(=S)R$^A$, —C(=S)N(R$^A$)$_2$, —C(=S)SR$^A$, —NH$_2$, —N(OR$^B$)R$^B$, —N(R$^B$)$_2$, —NR$^B$SO$_2R^A$, —NR$^B$C(=O)R$^A$, —NR$^B$CO$_2R^A$, —NR$^B$C(=O)N(R$^B$)$_2$, —NR$^B$C(=NR$^B$)N(R$^B$)$_2$, —OH, —OR$^A$, —SO$_2R^A$, —SO$_2$OR$^A$, —SO$_2$N(R$^B$)$_2$, —S(=O)

$R^A$), —Si($R^A$)$_3$, $C_{1-10}$ alkyl, $C_{1-10}$ fluoroalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 $R^D$ groups, wherein $R^A$, $R^B$, and $R^D$ are as defined herein.

In certain embodiments, $R^1$ is hydrogen, —C(=O)$R^A$, —CO$_2R^A$, —C(=O)S$R^A$, —C(=O)N($R^B$)$_2$, —C(=O)N$R^B$SO$_2R^A$, —C(=N$R^B$)$R^A$, —C(=N$R^B$)O$R^A$, —C(=N$R^B$)N($R^B$)$_2$, —C(=S)$R^A$, —C(=S)N($R^A$)$_2$, —C(=S)S$R^A$, —SO$_2R^A$, —SO$_2$O$R^A$, —SO$_2$N($R^B$)$_2$, —S(=O)$R^A$), or —Si($R^A$)$_3$, wherein $R^A$ and $R^B$ are as defined herein. In certain embodiments, $R^1$ is hydrogen or —C(=O)$R^A$, wherein $R^A$ is as defined herein. In certain embodiments, $R^1$ is hydrogen or —C(=O)$R^A$, wherein $R^A$ is $C_{1-10}$ alkyl. In certain embodiments, $R^1$ is hydrogen or —C(=O)$R^A$, wherein $R^A$ is $C_{1-6}$ alkyl. In certain embodiments, $R^1$ is hydrogen or —C(=O)CH$_3$. In certain embodiments, $R^1$ is hydrogen. In certain embodiments, $R^1$ is —C(=O)CH$_3$.

In certain embodiments, $R^2$ is hydrogen, —C(=O)$R^A$, —CO$_2R^A$, —C(=O)S$R^A$, —C(=O)N($R^B$)$_2$, —C(=O)N$R^B$SO$_2R^A$, —C(=N$R^B$)$R^A$, —C(=N$R^B$)O$R^A$, —C(=N$R^B$)N($R^B$)$_2$, —C(=S)$R^A$, —C(=S)N($R^A$)$_2$, —C(=S)S$R^A$, —SO$_2R^A$, —SO$_2$O$R^A$, —SO$_2$N($R^B$)$_2$, —S(=O)$R^A$), or —Si($R^A$)$_3$, wherein $R^A$ and $R^B$ are as defined herein. In certain embodiments, $R^2$ is hydrogen or —C(=O)$R^A$, wherein $R^A$ is as defined herein. In certain embodiments, $R^2$ is hydrogen or —C(=O)$R^A$, wherein $R^A$ is $C_{1-10}$ alkyl. In certain embodiments, $R^2$ is hydrogen or —C(=O)$R^A$, wherein $R^A$ is $C_{1-6}$ alkyl. In certain embodiments, $R^2$ is hydrogen or —C(=O)CH$_3$. In certain embodiments, $R^2$ is hydrogen. In certain embodiments, $R^2$ is —C(=O)CH$_3$.

In certain embodiments, $R^3$ is hydrogen, —C(=O)$R^A$, —CO$_2R^A$, —C(=O)S$R^A$, —C(=O)N($R^B$)$_2$, —C(=O)N$R^B$SO$_2R^A$, —C(=N$R^B$)$R^A$, —C(=N$R^B$)O$R^A$, —C(=N$R^B$)N($R^B$)$_2$, —C(=S)$R^A$, —C(=S)N($R^A$)$_2$, —C(=S)S$R^A$, —SO$_2R^A$, —SO$_2$O$R^A$, —SO$_2$N($R^B$)$_2$, —S(=O)$R^A$), or —Si($R^A$)$_3$, wherein $R^A$ and $R^B$ are as defined herein. In certain embodiments, $R^3$ is hydrogen or —C(=O)$R^A$, wherein $R^A$ is as defined herein. In certain embodiments, $R^3$ is hydrogen or —C(=O)$R^A$, wherein $R^A$ is $C_{1-10}$ alkyl. In certain embodiments, $R^3$ is hydrogen or —C(=O)$R^A$, wherein $R^A$ is $C_{1-6}$ alkyl. In certain embodiments, $R^3$ is hydrogen or —C(=O)CH$_3$. In certain embodiments, $R^3$ is hydrogen. In certain embodiments, $R^3$ is —C(=O)CH$_3$.

In certain embodiments, $R^4$ is hydrogen, —C(=O)$R^A$, —CO$_2R^A$, —C(=O)S$R^A$, —C(=O)N($R^B$)$_2$, —C(=O)N$R^B$SO$_2R^A$, —C(=N$R^B$)$R^A$, —C(=N$R^B$)O$R^A$, —C(=N$R^B$)N($R^B$)$_2$, —C(=S)$R^A$, —C(=S)N($R^A$)$_2$, —C(=S)S$R^A$, —SO$_2R^A$, —SO$_2$O$R^A$, —SO$_2$N($R^B$)$_2$, —S(=O)$R^A$), and —Si($R^A$)$_3$, wherein $R^A$ and $R^B$ are as defined herein. In certain embodiments, $R^4$ is hydrogen or —C(=O)$R^A$, wherein $R^A$ is as defined herein. In certain embodiments, $R^4$ is hydrogen or —C(=O)$R^A$, wherein $R^A$ is $C_{1-10}$ alkyl. In certain embodiments, $R^4$ is hydrogen or —C(=O)$R^A$, wherein $R^A$ is $C_{1-6}$ alkyl. In certain embodiments, $R^4$ is hydrogen or —C(=O)CH$_3$. In certain embodiments, $R^4$ is hydrogen. In certain embodiments, $R^4$ is —C(=O)CH$_3$.

As defined generally above, $R^5$ is hydrogen, an amino protecting group, or the group (A). Amino protecting groups are defined herein, e.g., —CHO, —C(=O)$R^A$, —CO$_2R^A$, —C(=O)S$R^A$, —C(=O)N($R^B$)$_2$, —C(=O)N$R^B$SO$_2R^A$, —C(=N$R^B$)$R^A$, —C(=N$R^B$)O$R^A$, —C(=N$R^B$)N($R^B$)$_2$, —C(=S)$R^A$, —C(=S)N($R^A$)$_2$, —C(=S)S$R^A$, —NH$_2$, —N(O$R^B$)$R^B$, —N($R^B$)$_2$, —N$R^B$SO$_2R^A$, —N$R^B$C(=O)$R^A$, —N$R^B$CO$_2R^A$, —N$R^B$C(=O)N($R^B$)$_2$, —N$R^B$C(=N$R^B$)N($R^B$)$_2$, —OH, —O$R^A$, —SO$_2R^A$, —SO$_2$O$R^A$, —SO$_2$N($R^B$)$_2$, —S(=O)$R^A$), —Si($R^A$)$_3$, $C_{1-10}$ alkyl, $C_{1-10}$ fluoroalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 $R^D$ groups, wherein $R^A$, $R^B$, and $R^D$ are as defined herein.

In certain embodiments, $R^5$ is hydrogen, —C(=O)$R^A$, —CO$_2R^A$, —C(=O)S$R^A$, —C(=O)N($R^B$)$_2$, —C(=O)N$R^B$SO$_2R^A$, —C(=N$R^B$)$R^A$, —C(=N$R^B$)O$R^A$, —C(=N$R^B$)N($R^B$)$_2$, —C(=S)$R^A$, —C(=S)N($R^A$)$_2$, —C(=S)S$R^A$, —SO$_2R^A$, —SO$_2$O$R^A$, —SO$_2$N($R^B$)$_2$, —S(=O)$R^A$), and —Si($R^A$)$_3$, wherein $R^A$ and $R^B$ are as defined herein, or the group (A).

In certain embodiments, $R^5$ is hydrogen or —C(=O)$R^A$ wherein $R^A$ is as defined herein, or the group (A).

In certain embodiments, $R^5$ is hydrogen or the group (A).

In certain embodiments, $R^5$ is hydrogen.

In certain embodiments, $R^5$ is the group (A).

As defined generally above, $R^6$, $R^7$, $R^8$, $R^9$, $R^{10}$, and $R^{11}$ are each independently hydrogen or a hydroxyl protecting group. Hydroxyl protecting groups are defined herein, and include, but are not limited to, —C(=O)$R^A$, —CO$_2R^A$, —C(=O)—O—C(=O)$R^A$, —C(=O)S$R^A$, —C(=O)N($R^B$)$_2$, —C(=O)N$R^B$SO$_2R^A$, —C(=N$R^B$)$R^A$, —C(=N$R^B$)O$R^A$, —C(=N$R^B$)N($R^B$)$_2$, —C(=S)$R^A$, —C(=S)N($R^A$)$_2$, —C(=S)S$R^A$, —SO$_2R^A$, —SO$_2$O$R^A$, —SO$_2$N($R^B$)$_2$, —S(=O)$R^A$, —Si($R^A$)$_3$, $C_{1-10}$ alkyl, $C_{1-10}$ fluoroalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 $R^D$ groups, wherein $R^A$, $R^B$, and $R^D$ are as defined herein.

In certain embodiments, $R^6$ is hydrogen, —C(=O)$R^A$, —CO$_2R^A$, —C(=O)—O—C(=O)$R^A$, —C(=O)S$R^A$, —C(=O)N($R^B$)$_2$, —C(=O)N$R^B$SO$_2R^A$, —C(=N$R^B$)$R^A$, —C(=N$R^B$)O$R^A$, —C(=N$R^B$)N($R^B$)$_2$, —C(=S)$R^A$, —C(=S)N($R^A$)$_2$, —C(=S)S$R^A$, —SO$_2R^A$, —SO$_2$O$R^A$, —SO$_2$N($R^B$)$_2$, —S(=O)$R^A$, and —Si($R^A$)$_3$, wherein $R^A$ and $R^B$ are as defined herein. In certain embodiments, $R^6$ is hydrogen or —C(=O)$R^A$, wherein $R^A$ is as defined herein. In certain embodiments, $R^6$ is hydrogen or —C(=O)$R^A$, wherein $R^A$ is $C_{1-10}$ alkyl. In certain embodiments, $R^6$ is hydrogen or —C(=O)$R^A$, wherein $R^A$ is $C_{1-6}$ alkyl. In certain embodiments, $R^6$ is hydrogen or —C(=O)CH$_3$. In certain embodiments, $R^6$ is hydrogen. In certain embodiments, $R^6$ is —C(=O)CH$_3$.

In certain embodiments, $R^7$ is hydrogen, —C(=O)$R^A$, —CO$_2R^A$, —C(=O)—O—C(=O)$R^A$, —C(=O)S$R^A$, —C(=O)N($R^B$)$_2$, —C(=O)N$R^B$SO$_2R^A$, —C(=N$R^B$)$R^A$, —C(=N$R^B$)O$R^A$, —C(=N$R^B$)N($R^B$)$_2$, —C(=S)$R^A$, —C(=S)N($R^A$)$_2$, —C(=S)S$R^A$, —SO$_2R^A$, —SO$_2$O$R^A$, —SO$_2$N($R^B$)$_2$, —S(=O)$R^A$, or —Si($R^A$)$_3$, wherein $R^A$ and $R^B$ are as defined herein. In certain embodiments, $R^7$ is hydrogen or —C(=O)$R^A$, wherein $R^A$ is as defined herein. In certain embodiments, $R^7$ is hydrogen or —C(=O)$R^A$, wherein $R^A$ is $C_{1-10}$ alkyl. In certain embodiments, $R^7$ is hydrogen or —C(=O)$R^A$, wherein $R^A$ is $C_{1-6}$ alkyl. In certain embodiments, $R^7$ is hydrogen or —C(=O)CH$_3$. In certain embodiments, $R^7$ is hydrogen. In certain embodiments, $R^7$ is —C(=O)CH$_3$.

In certain embodiments, $R^8$ is hydrogen, —C(=O)$R^A$, —CO$_2R^A$, —C(=O)—O—C(=O)$R^A$, —C(=O)S$R^A$, —C(=O)N($R^B$)$_2$, —C(=O)N$R^B$SO$_2R^A$, —C(=N$R^B$)$R^A$, —C(=N$R^B$)O$R^A$, —C(=N$R^B$)N($R^B$)$_2$, —C(=S)$R^A$, —C(=S)N($R^A$)$_2$, —C(=S)S$R^A$, —SO$_2R^A$, —SO$_2$O$R^A$, —SO$_2$N($R^B$)$_2$, —S(=O)$R^A$, or —Si($R^A$)$_3$, wherein $R^A$ and $R^B$ are as defined herein. In certain embodiments, $R^8$ is hydrogen or —C(=O)$R^A$, wherein $R^A$ is as defined herein. In certain embodiments, $R^8$ is hydrogen or —C(=O)$R^A$, wherein $R^A$ is $C_{1-10}$ alkyl. In certain embodiments, $R^8$ is hydrogen or —C(=O)$R^A$, wherein $R^A$ is $C_{1-6}$ alkyl. In certain embodiments, $R^8$ is hydrogen or —C(=O)CH$_3$. In certain embodiments, $R^8$ is hydrogen. In certain embodiments, $R^8$ is —C(=O)CH$_3$.

In certain embodiments, $R^9$ is hydrogen, —C(=O)$R^A$, —CO$_2R^A$, —C(=O)—O—C(=O)$R^A$, —C(=O)S$R^A$, —C(=O)N($R^B$)$_2$, —C(=O)N$R^B$SO$_2R^A$, —C(=N$R^B$)$R^A$, —C(=N$R^B$)O$R^A$, —C(=N$R^B$)N($R^B$)$_2$, —C(=S)$R^A$, —C(=S)N($R^A$)$_2$, —C(=S)S$R^A$, —SO$_2R^A$, —SO$_2$O$R^A$, —SO$_2$N($R^B$)$_2$, —S(=O)$R^A$, or —Si($R^A$)$_3$, wherein $R^A$ and $R^B$ are as defined herein. In certain embodiments, $R^9$ is hydrogen or —C(=O)$R^A$, wherein $R^A$ is as defined herein. In certain embodiments, $R^9$ is hydrogen or —C(=O)$R^A$, wherein $R^A$ is $C_{1-10}$ alkyl. In certain embodiments, $R^9$ is hydrogen or —C(=O)$R^A$, wherein $R^A$ is $C_{1-6}$ alkyl. In certain embodiments, $R^9$ is hydrogen or —C(=O)CH$_3$. In certain embodiments, $R^9$ is hydrogen. In certain embodiments, $R^9$ is —C(=O)CH$_3$.

In certain embodiments, $R^{10}$ is hydrogen, —C(=O)$R^A$, —CO$_2R^A$, —C(=O)—O—C(=O)$R^A$, —C(=O)S$R^A$, —C(=O)N($R^B$)$_2$, —C(=O)N$R^B$SO$_2R^A$, —C(=N$R^B$)$R^A$, —C(=N$R^B$)O$R^A$, —C(=N$R^B$)N($R^B$)$_2$, —C(=S)$R^A$, —C(=S)N($R^A$)$_2$, —C(=S)S$R^A$, —SO$_2R^A$, —SO$_2$O$R^A$, —SO$_2$N($R^B$)$_2$, —S(=O)$R^A$, or —Si($R^A$)$_3$, wherein $R^A$ and $R^B$ are as defined herein. In certain embodiments, $R^{10}$ is hydrogen or —C(=O)$R^A$, wherein $R^A$ is as defined herein. In certain embodiments, $R^{10}$ is hydrogen or —C(=O)$R^A$, wherein $R^A$ is $C_{1-10}$ alkyl. In certain embodiments, $R^{10}$ is hydrogen or —C(=O)$R^A$, wherein $R^A$ is $C_{1-6}$ alkyl. In certain embodiments, $R^{10}$ is hydrogen or —C(=O)CH$_3$. In certain embodiments, $R^{10}$ is hydrogen. In certain embodiments, $R^{10}$ is —C(=O)CH$_3$.

In certain embodiments, $R^{11}$ is hydrogen, —C(=O)$R^A$, —CO$_2R^A$, —C(=O)—O—C(=O)$R^A$, —C(=O)S$R^A$, —C(=O)N($R^B$)$_2$, —C(=O)N$R^B$SO$_2R^A$, —C(=N$R^B$)$R^A$, —C(=N$R^B$)O$R^A$, —C(=N$R^B$)N($R^B$)$_2$, —C(=S)$R^A$, —C(=S)N($R^A$)$_2$, —C(=S)S$R^A$, —SO$_2R^A$, —SO$_2$O$R^A$, —SO$_2$N($R^B$)$_2$, —S(=O)$R^A$, or —Si($R^A$)$_3$, wherein $R^A$ and $R^B$ are as defined herein. In certain embodiments, $R^{11}$ is hydrogen or —C(=O)$R^A$, wherein $R^A$ is as defined herein. In certain embodiments, $R^{11}$ is hydrogen or —C(=O) $R^A$, wherein $R^A$ is $C_{1-10}$ alkyl. In certain embodiments, $R^{11}$ is hydrogen or —C(=O)$R^A$, wherein $R^A$ is $C_{1-6}$ alkyl. In certain embodiments, $R^{11}$ is hydrogen or —C(=O)CH$_3$. In certain embodiments, $R^{10}$ is hydrogen. In certain embodiments, $R^{11}$ is —C(=O)CH$_3$.

In certain embodiments, $R^1, R^2, R^3, R^4, R^6, R^7, R^8, R^9, R^{10}$ and $R^{11}$ are each independently hydrogen or —C(=O)$R^A$, wherein $R^A$ is as defined herein.

In certain embodiments, $R^1$ and $R^2$ are each hydrogen.

In certain embodiments, $R^3$ and $R^4$ are each —C(=O)$R^A$, wherein $R^A$ is as defined herein. In certain embodiments, $R^3$ and $R^4$ are each —C(=O)CH$_3$.

In certain embodiments, $R^6, R^7, R^8, R^9, R^{10}$ and $R^{11}$ are each hydrogen.

As generally defined above, $R^{12}$ is hydrogen, a hydroxyl protecting group, or the group (D), wherein $R^{13}, R^{14}, R^{15}$, and $R^{16}$ are each independently hydrogen or a hydroxyl protecting group. Hydroxyl protecting groups are defined herein, and include, but are not limited to, —C(=O)$R^A$, —CO$_2R^A$, —C(=O)—O—C(=O)$R^A$, —C(=O)S$R^A$, —C(=O)N($R^B$)$_2$, —C(=O)N$R^B$SO$_2R^A$, —C(=N$R^B$)$R^A$, —C(=N$R^B$)O$R^A$, —C(=N$R^B$)N($R^B$)$_2$, —C(=S)$R^A$, —C(=S)N($R^A$)$_2$, —C(=S)S$R^A$, —SO$_2R^A$, —SO$_2$O$R^A$, —SO$_2$N($R^B$)$_2$, —S(=O)$R^A$, —Si($R^A$)$_3$, $C_{1-10}$ alkyl, $C_{1-10}$ fluoroalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 $R^D$ groups, wherein $R^A$, $R^B$, and $R^D$ are as defined herein.

In certain embodiments, $R^{12}$ is hydrogen, —C(=O)$R^A$, —CO$_2R^A$, —C(=O)—O—C(=O)$R^A$, —C(=O)S$R^A$, —C(=O)N($R^B$)$_2$, —C(=O)N$R^B$SO$_2R^A$, —C(=N$R^B$)$R^A$, —C(=N$R^B$)O$R^A$, —C(=N$R^B$)N($R^B$)$_2$, —C(=S)$R^A$, —C(=S)N($R^A$)$_2$, —C(=S)S$R^A$, —SO$_2R^A$, —SO$_2$O$R^A$, —SO$_2$N($R^B$)$_2$, —S(=O)$R^A$, and —Si($R^A$)$_3$, wherein $R^A$ and $R^B$ are as defined herein, or the group (D), wherein $R^{13}$, $R^{14}, R^{15}$, and $R^{16}$ are each independently —C(=O)$R^A$, —CO$_2R^A$, —C(=O)—O—C(=O)$R^A$, —C(=O)S$R^A$, —C(=O)N($R^B$)$_2$, —C(=O)N$R^B$SO$_2R^A$, —C(=N$R^B$)$R^A$, —C(=N$R^B$)O$R^A$, —C(=N$R^B$)N($R^B$)$_2$, —C(=S)$R^A$, —C(=S)N($R^A$)$_2$, —C(=S)S$R^A$, —SO$_2R^A$, —SO$_2$O$R^A$, —SO$_2$N($R^B$)$_2$, —S(=O)$R^A$, or —Si($R^A$)$_3$, wherein $R^A$ and $R^B$ are as defined herein.

In certain embodiments, $R^{12}$ is hydrogen, —C(=O)$R^A$, or the group (D), wherein $R^{13}$, $R^{14}$, $R^{15}$, and $R^{16}$ are each independently hydrogen or —C(=O)$R^A$, and wherein $R^A$ is as defined herein.

In certain embodiments, $R^{12}$ is hydrogen, —C(=O)CH$_3$ or the group (D), wherein $R^{13}$, $R^{14}$, $R^{15}$, and $R^{16}$ are each independently hydrogen or —C(=O)CH$_3$.

In certain embodiments, $R^{12}$ is hydrogen. In certain embodiments, $R^{12}$ is —C(=O)CH$_3$.

In certain embodiments, $R^{12}$ is the group (D), wherein $R^{13}$, $R^{14}$, $R^{15}$, and $R^{16}$ are each independently hydrogen or —C(=O)CH$_3$. In certain embodiments, $R^{13}$, $R^{14}$, $R^{15}$, and $R^{16}$ are each hydrogen.

As generally defined above, $R^a$ and $R^b$ are each independently hydrogen or a hydroxyl protecting group. Hydroxyl protecting groups are defined herein, and include, but are not limited to, —C(=O)$R^A$, —CO$_2R^A$, —C(=O)—O—C(=O)$R^A$, —C(=O)S$R^A$, —C(=O)N($R^B$)$_2$, —C(=O)N$R^B$SO$_2R^A$, —C(=N$R^B$)$R^A$, —C(=N$R^B$)O$R^A$, —C(=N$R^B$)N($R^B$)$_2$, —C(=S)$R^A$, —C(=S)N($R^A$)$_2$, —C(=S)S$R^A$, —SO$_2R^A$, —SO$_2$O$R^A$, —SO$_2$N($R^B$)$_2$, —S(=O)$R^A$, —Si($R^A$)$_3$, $C_{1-10}$ alkyl, $C_{1-10}$ fluoroalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 $R^D$ groups, wherein $R^A$, $R^B$, and $R^D$ are as defined herein.

In certain embodiments, $R^a$ and $R^b$ are each independently hydrogen or $C_{1-10}$ alkyl. In certain embodiments, $R^a$ and $R^b$ are each independently hydrogen or $C_{1-6}$ alkyl. In certain embodiments, $R^a$ and $R^b$ are each independently hydrogen or —CH$_3$. In certain embodiments, $R^a$ is hydrogen. In certain embodiments, $R^b$ is hydrogen. In certain embodiments, both $R^a$ and $R^b$ are hydrogen.

In certain embodiments, $R^a, R^b, R^1, R^2, R^6, R^7, R^8, R^9, R^{10}$ and $R^{11}$ are each hydrogen, and $R^3$ and $R^4$ are each —C(=O)CH$_3$.

In certain embodiments, $R^a$, $R^b$, $R^1$, $R^2$, $R^6$, $R^7$, $R^8$, $R^9$, $R^{10}$ and $R^{11}$ are each hydrogen, $R^3$ and $R^4$ are each —C(=O)CH$_3$, $R^5$ is the group (A), and $R^{12}$ is the group (D) wherein $R^{13}$, $R^{14}$, $R^{15}$, and $R^{16}$ are each hydrogen.

Various sub-genera of Formula (II) are further described herein. For example, in certain embodiments, the compound of Formula (II) is a compound of Formula (II-a):

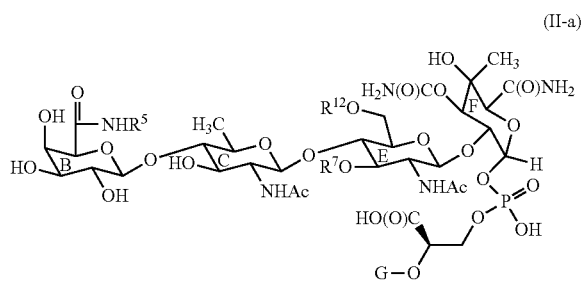

(II-a)

or a pharmaceutically acceptable form thereof; wherein G, $R^5$, and $R^{12}$ are as defined herein.

In certain embodiments the compound of Formula (II) is a compound of Formula (II-b):

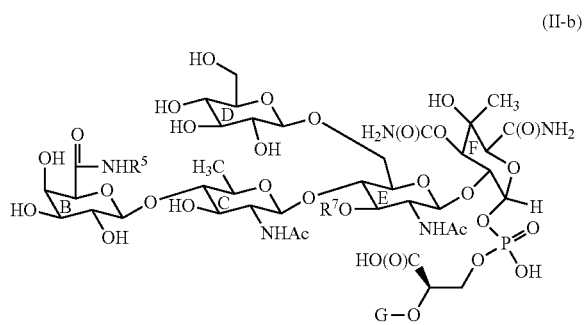

(II-b)

or a pharmaceutically acceptable form thereof; wherein G is as defined herein.

Compounds of Formula (III)

The present invention further provides compounds of Formula (III), as provided below, which include compounds comprising Rings C, E and F, and optionally Ring D, of the moenomycin A sugar scaffold.

For example, in one aspect, the present invention provides a compound of Formula (III):

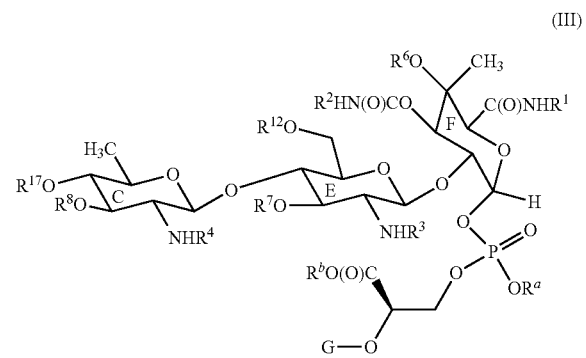

(III)

or a pharmaceutically acceptable form thereof; wherein $R^1$, $R^2$, $R^3$, $R^4$, $R^6$, $R^7$, $R^8$, $R^{12}$, $R^a$, and $R^b$, are as defined above and herein; G is a group of Formula (a), (b), or (c) as defined above and herein; and $R^{17}$ is hydrogen or a hydroxyl protecting group.

Hydroxyl protecting groups are defined herein, and include, but are not limited to, —C(=O)$R^A$, —CO$_2R^A$, —C(=O)—O—C(=O)$R^A$, —C(=O)S$R^A$, —C(=O)N($R^B$)$_2$, —C(=O)N$R^B$SO$_2R^A$, —C(=N$R^B$)$R^A$, —C(=N$R^B$)O$R^A$, —C(=N$R^B$)N($R^B$)$_2$, —C(=S)$R^A$, —C(=S)N($R^A$)$_2$, —C(=S)S$R^A$, —SO$_2R^A$, —SO$_2$O$R^A$, —SO$_2$N($R^B$)$_2$, —S(=O)$R^A$, —Si($R^A$)$_3$, C$_{1-10}$ alkyl, C$_{1-10}$ fluoroalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 $R^D$ groups, wherein $R^A$, $R^B$, and $R^D$ are as defined herein.

In certain embodiments, $R^{17}$ is hydrogen, —C(=O)$R^A$, —CO$_2R^A$, —C(=O)—O—C(=O)$R^A$, —C(=O)S$R^A$, —C(=O)N($R^B$)$_2$, —C(=O)N$R^B$SO$_2R^A$, —C(=N$R^B$)$R^A$, —C(=N$R^B$)O$R^A$, —C(=N$R^B$)N($R^B$)$_2$, —C(=S)$R^A$, —C(=S)N($R^A$)$_2$, —C(=S)S$R^A$, —SO$_2R^A$, —SO$_2$O$R^A$, —SO$_2$N($R^B$)$_2$, —S(=O)$R^A$, or —Si($R^A$)$_3$, wherein $R^A$ and $R^B$ are as defined herein. In certain embodiments, $R^{17}$ is hydrogen or —C(=O)$R^A$, wherein $R^A$ is as defined herein. In certain embodiments, $R^{17}$ is hydrogen or —C(=O)$R^A$, wherein $R^A$ is C$_{1-10}$ alkyl. In certain embodiments, $R^{17}$ is hydrogen or —C(=O)$R^A$, wherein $R^A$ is C$_{1-6}$ alkyl. In certain embodiments, $R^{17}$ is hydrogen or —C(=O)CH$_3$. In certain embodiments, $R^{17}$ is hydrogen. In certain embodiments, $R^{17}$ is —C(=O)CH$_3$.

In certain embodiments, $R^a$, $R^b$, $R^1$, $R^2$, $R^6$, $R^7$, $R^8$, and $R^{17}$ are each hydrogen, and $R^3$ and $R^4$ are each —C(=O)CH$_3$.

In certain embodiments, $R^a$, $R^b$, $R^1$, $R^2$, $R^6$, $R^7$, $R^8$, and $R^{17}$ are each hydrogen, $R^3$ and $R^4$ are each —C(=O)CH$_3$, and $R^{12}$ is the group (D) wherein $R^{13}$, $R^{14}$, $R^{15}$, and $R^{16}$ are each hydrogen.

Various sub-genera of Formula (III) are further described below and herein. For example, in certain embodiments, the compound of Formula (III) is of Formula (III-a):

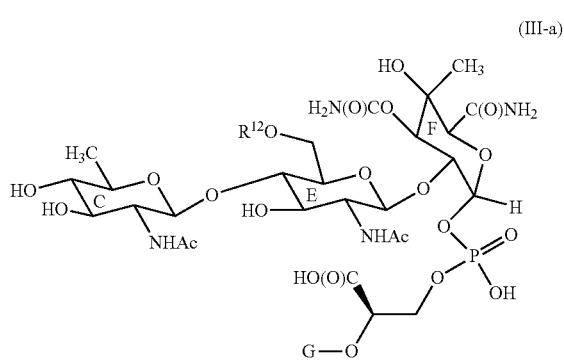

(III-a)

or a pharmaceutically acceptable form thereof; wherein $R^{12}$ and G are as defined herein.

In yet other embodiments, the compound of the Formula (III) is of Formula (III-b):

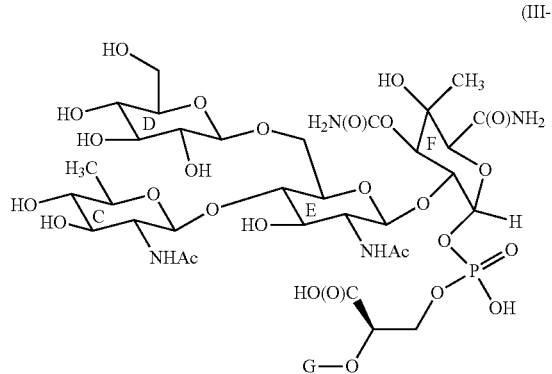

or a pharmaceutically acceptable form thereof; wherein G is as defined herein.

Compounds of Formula (IV)

The present invention further provides compounds of Formula (IV), as provided below, which include compounds comprising Rings E and F, and optionally Ring D, of the moenomycin A sugar scaffold.

For example, in one aspect, provided is a compound of Formula (IV):

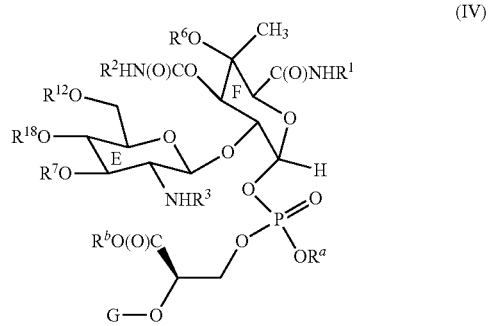

or a pharmaceutically acceptable form thereof; wherein $R^1$, $R^2$, $R^3$, $R^6$, $R^7$, $R^{12}$, $R^a$, and $R^b$ are as defined above and herein; G is a group of Formula (a), (b), or (c) as defined above and herein; and $R^{18}$ is hydrogen or a hydroxyl protecting group.

Hydroxyl protecting groups are defined herein, and include, but are not limited to, $-C(=O)R^A$, $-CO_2R^A$, $-C(=O)-O-C(=O)R^A$, $-C(=O)SR^A$, $-C(=O)N(R^B)_2$, $-C(=O)NR^BSO_2R^A$, $-C(=NR^B)R^A$, $-C(=NR^B)OR^A$, $-C(=NR^B)N(R^B)_2$, $-C(=S)R^A$, $-C(=S)N(R^A)_2$, $-C(=S)SR^A$, $-SO_2R^A$, $-SO_2OR^A$, $-SO_2N(R^B)_2$, $-S(=O)R^A$, $-Si(R^A)_3$, $C_{1-10}$ alkyl, $C_{1-10}$ fluoroalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 $R^D$ groups, wherein $R^A$, $R^B$, and $R^D$ are as defined herein.

In certain embodiments, $R^{18}$ is hydrogen, $-C(=O)R^A$, $-CO_2R^A$, $-C(=O)-O-C(=O)R^A$, $-C(=O)SR^A$, $-C(=O)N(R^B)_2$, $-C(=O)NR^BSO_2R^A$, $-C(=NR^B)R^A$, $-C(=NR^B)OR^A$, $-C(=NR^B)N(R^B)_2$, $-C(=S)R^A$, $-C(=S)N(R^A)_2$, $-C(=S)SR^A$, $-SO_2R^A$, $-SO_2OR^A$, $-SO_2N(R^B)_2$, $-S(=O)R^A$, and $-Si(R^A)_3$, wherein $R^A$ and $R^B$ are as defined herein. In certain embodiments, $R^{18}$ is hydrogen or $-C(=O)R^A$, wherein $R^A$ is as defined herein. In certain embodiments, $R^{18}$ is hydrogen or $-C(=O)R^A$, wherein $R^A$ is $C_{1-10}$ alkyl. In certain embodiments, $R^{18}$ is hydrogen or $-C(=O)R^A$, wherein $R^A$ is $C_{1-6}$ alkyl. In certain embodiments, $R^{18}$ is hydrogen or $-C(=O)CH_3$. In certain embodiments, $R^{18}$ is hydrogen. In certain embodiments, $R^{18}$ is $-C(=O)CH_3$.

In certain embodiments $R^a$, $R^b$, $R^1$, $R^2$, $R^6$, $R^7$, and $R^{18}$ are each hydrogen, and $R^3$ is $-C(=O)CH_3$.

In certain embodiments $R^a$, $R^b$, $R^1$, $R^2$, $R^6$, $R^7$, and $R^{18}$ are each hydrogen, $R^3$ is $-C(=O)CH_3$, and $R^{12}$ is the group (D) wherein $R^{13}$, $R^{14}$, $R^{15}$, and $R^{16}$ are each hydrogen.

Various sub-genera of Formula (IV) are further described herein.

For example, in certain embodiments, the compound of Formula (IV) is a compound of Formula (IV-a):

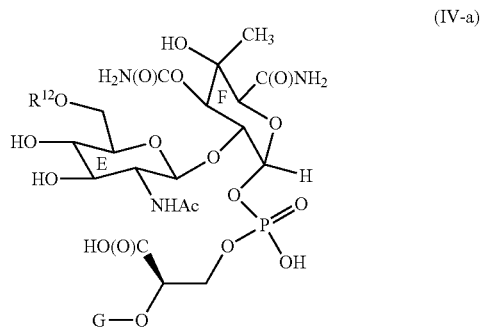

or a pharmaceutically acceptable form thereof; wherein $R^{12}$ and G are as defined herein.

In yet other embodiments the compound of Formula (IV) is of Formula (IV-b):

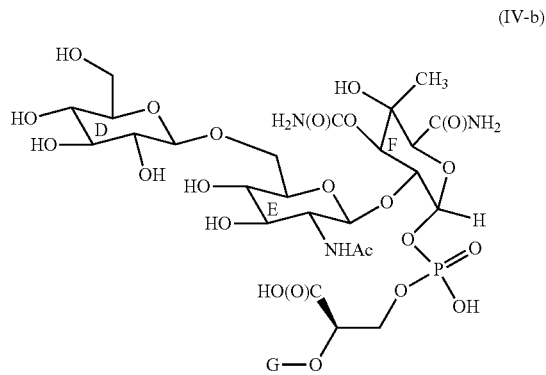

or a pharmaceutically acceptable form thereof; wherein G is as defined herein.

Group G of Formula (a)

As generally described herein, in certain embodiments, compounds of Formula (I), (II), (III), and (IV) include a group G of Formula (a):

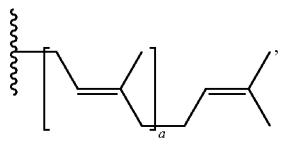

wherein a is 3, 4, or 5.

For example, in certain embodiments, the group G a group selected from the group consisting of:

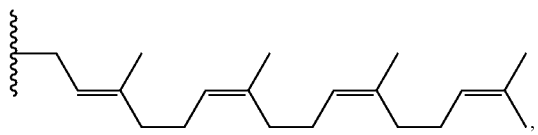

wherein a is 3;

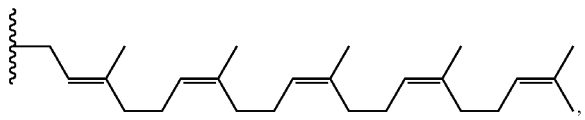

wherein a is 4; or

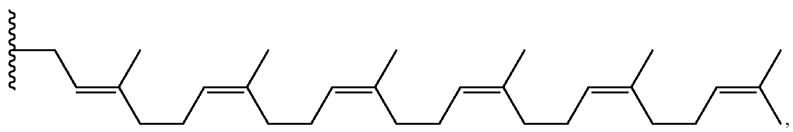

wherein a is 5.

Group G of Formula (b)

As generally described herein, in certain embodiments, compounds of Formula (I), (II), (III), and (IV) include a group G of Formula (b):

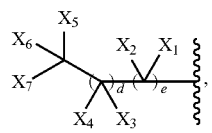

wherein:

$X_1$, $X_2$, $X_3$, $X_4$, $X_5$, $X_6$, and $X_7$ are each independently hydrogen or halogen;

d is an integer between 1 and 25, inclusive; and e is an integer of between 2 and 25, inclusive;

provided the sum of d and e is greater than 16.

In certain embodiments, e is 2, 3, 4, 5, 6, 7, 8, 9, 10, 11, 12, 13, 14, 15, 16, 17, 18, 19, 20, 21, 22, 23 24, or 25. In certain embodiments, d is 1, 2, 3, 4, 5, 6, 7, 8, 9, 10, 11, 12, 13, 14, 15, 16, 17, 18, 19, 20, 21, 22, 23 24, or 25. Any particular combination of e or d is contemplated, provided the sum of d and e is greater than 16.

For example, in certain embodiments, e is 16 or an integer greater than 16, and d is 1 or an integer greater than 1. In certain embodiments, e is 15, and d is 2 or an integer greater than 2. In certain embodiments, e is 14, and d is 3 or an integer greater than 3. In certain embodiments, e is 13, and d is 4 or an integer greater than 4. In certain embodiments, e is 12, and d is 5 or an integer greater than 5. In certain embodiments, e is 11, and d is 6 or an integer greater than 6. In certain embodiments, e is 10, and d is 7 or an integer greater than 7. In certain embodiments, e is 9, and d is 8 or an integer greater than 8. In certain embodiments, e is 8, and d is 9 or an integer greater than 9. In certain embodiments, e is 7, and d is 10 or an integer greater than 10. In certain embodiments, e is 6, and d is 11 or an integer greater than 11. In certain embodiments, e is 5, and d is 12 or an integer greater than 12. In certain embodiments, e is 4, and d is 13 or an integer greater than 13. In certain embodiments, e is 3, and d is 14 or an integer greater than 14. In certain embodiments, e is 2, and d is 15 or an integer greater than 15.

In certain embodiments, e is 10, and d is 7 or an integer greater than 7, e.g., d is 7, 8, 9, 10, 11, 12, 13, 14, 15, 16, 17, 18, 19, 20, 21, 22, 23 24, or 25. In certain embodiments, e is 10 and d is 7. In certain embodiments, e is 10 and d is 8. In certain embodiments, e is 10 and d is 9. In certain embodiments, e is 10 and d is 10. In certain embodiments, e is 10 and d is 11. In certain embodiments, e is 10 and d is 12. In certain embodiments, e is 10 and d is 13. In certain embodiments, e is 10 and d is 14. In certain embodiments, e is 10 and d is 15.

In certain embodiments, at least one of $X_1$, $X_2$, $X_3$, $X_4$, $X_5$, $X_6$, or $X_7$ is halogen, e.g., fluoro. In certain embodiments, at least two of $X_1$, $X_2$, $X_3$, $X_4$, $X_5$, $X_6$, or $X_7$ is halogen. In certain embodiments, at least three of $X_1$, $X_2$, $X_3$, $X_4$, $X_5$, $X_6$, or $X_7$ is halogen. In certain embodiments, at least four of $X_1$, $X_2$, $X_3$, $X_4$, $X_5$, $X_6$, or $X_7$ is halogen. In certain embodiments, at least five of $X_1$, $X_2$, $X_3$, $X_4$, $X_5$, $X_6$, or $X_7$ is halogen. In certain embodiments, at least six of $X_1$, $X_2$, $X_3$, $X_4$, $X_5$, $X_6$, or $X_7$ is halogen.

In certain embodiments, each instance of $X_1$ and $X_2$ is hydrogen. In certain embodiments, each instance of $X_1$ and $X_2$ is halogen, e.g., fluoro.

In certain embodiments, each instance of $X_3$ and $X_4$ is hydrogen. In certain embodiments, each instance of $X_3$ and $X_4$ is halogen, e.g., fluoro.

In certain embodiments, each instance of $X_5$, $X_6$, and $X_7$ is hydrogen. In certain embodiments, each instance of $X_5$, $X_6$, and $X_7$ is halogen, e.g., fluoro.

In certain embodiments, each instance of $X_1$ and $X_2$ is fluoro, optionally wherein each instance of $X_3$ and $X_4$ is fluoro and/or each instance of $X_5$, $X_6$, and $X_7$ is fluoro. In certain embodiments, $X_1$ and $X_2$ are each fluoro, $X_3$ and $X_4$ are each hydrogen, and $X_5$, $X_6$, and $X_7$ are each hydrogen. In certain embodiments, $X_1$ and $X_2$ are each fluoro, $X_3$ and $X_4$ are each fluoro, and $X_5$, $X_6$, and $X_7$ are each hydrogen. In certain embodiments, $X_1$ and $X_2$ are each fluoro, $X_3$ and $X_4$ are each hydrogen, and $X_5$, $X_6$, and $X_7$ are each fluoro. In certain embodiments, $X_1$ and $X_2$ are each fluoro, $X_3$ and $X_4$ are each fluoro, and $X_5$, $X_6$, and $X_7$ are each fluoro.

Alternatively, in certain embodiments, each instance of $X_3$ and $X_4$ is fluoro, optionally wherein each instance of $X_1$ and $X_2$ is fluoro and/or each instance of $X_5$, $X_6$, and $X_7$ is fluoro. In certain embodiments, $X_3$ and $X_4$ are each fluoro, $X_1$ and $X_2$ are each hydrogen, and $X_5$, $X_6$, and $X_7$ are each hydrogen. In certain embodiments, $X_3$ and $X_4$ are each fluoro, $X_1$ and $X_2$ are each hydrogen, and $X_5$, $X_6$, and $X_7$ are each fluoro. In certain embodiments, $X_3$ and $X_4$ are each fluoro, $X_1$ and $X_2$ are each fluoro, and $X_5$, $X_6$, and $X_7$ are each hydrogen. In certain embodiments, $X_3$ and $X_4$ are each fluoro, $X_1$ and $X_2$ are each fluoro, and $X_5$, $X_6$, and $X_7$ are each fluoro.

Exemplary fluoroalkyl groups of formula (b), wherein $X_1$ and $X_2$ are hydrogen and $X_3$, $X_4$, $X_5$, $X_6$, and $X_7$ are each fluoro include, but are not limited to:

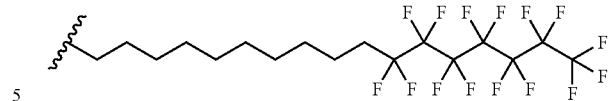

wherein e is 10, and d is 7;

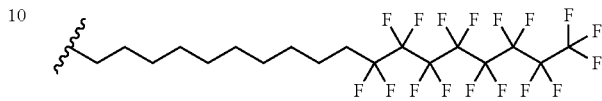

wherein e is 10, and d is 8;

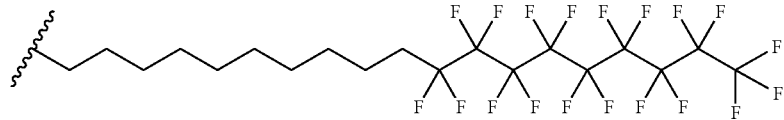

wherein e is 10, and d is 9;

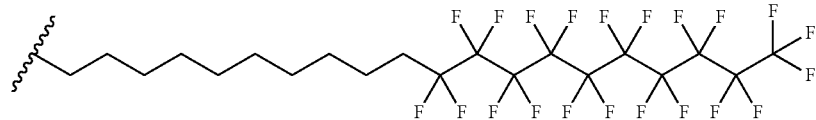

wherein e is 10, and d is 10;

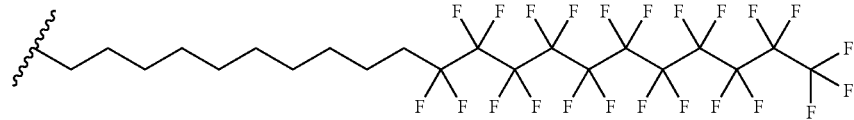

wherein e is 10, and d is 11;

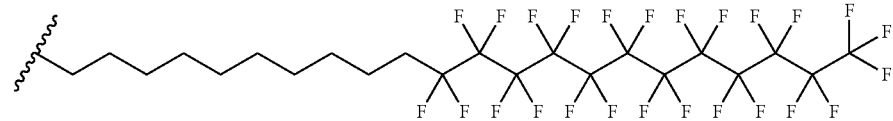

wherein e is 10, and d is 12;

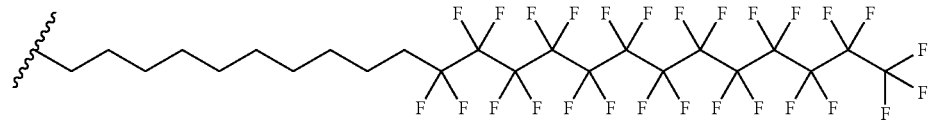

wherein e is 10, and d is 13;

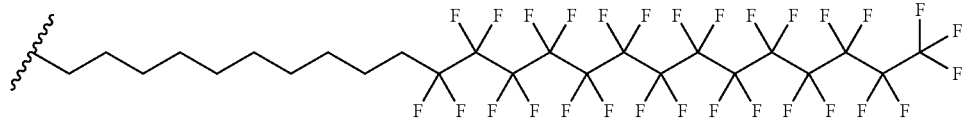
wherein e is 10, and d is 14; and
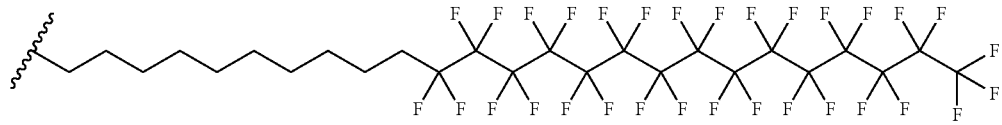
wherein e is 10, and d is 15.
Exemplary fluoroalkyl groups of formula (b), wherein each instance of $X_1$, $X_2$, $X_3$, $X_4$, $X_5$, $X_6$, and $X_7$ is fluoro, include but are not limited to:
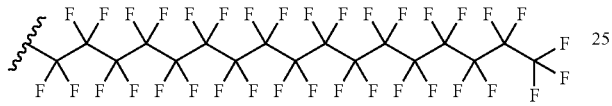
wherein e is 10, and d is 7;
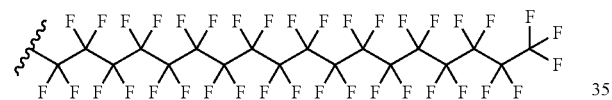
wherein e is 10, and d is 8;
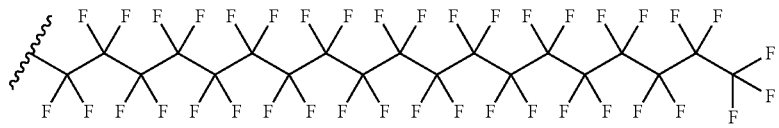
wherein e is 10, and d is 9;
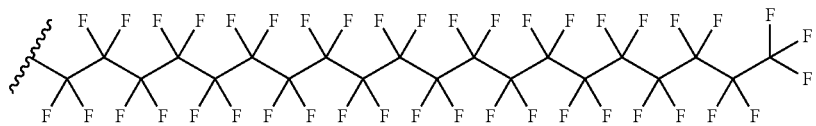
wherein e is 10, and d is 10;
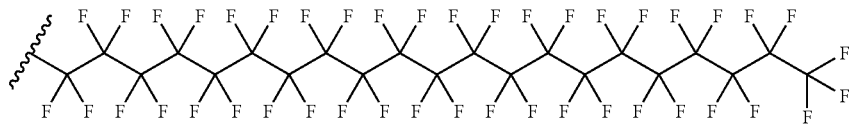
wherein e is 10, and d is 11;

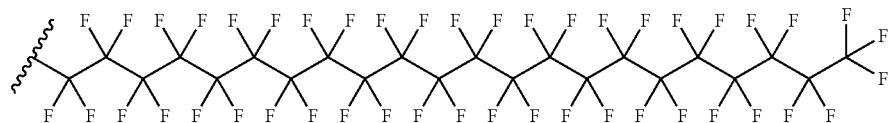

wherein e is 10, and d is 12;

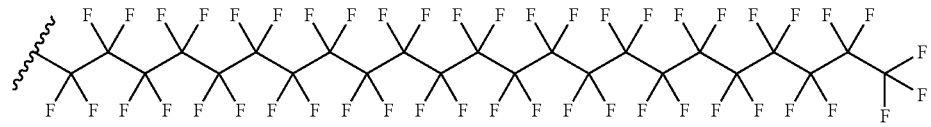

wherein e is 10, and d is 13;

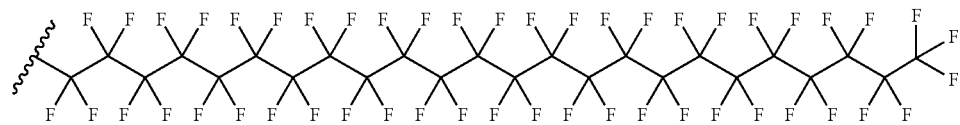

wherein e is 10, and d is 14; and

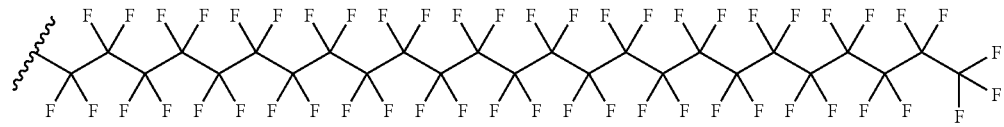

wherein e is 10, and d is 15.

Group G of Formula (c)

As generally described herein, in certain embodiments, compounds of Formula (I), (II), (III), and (IV) include a group G of Formula (c):

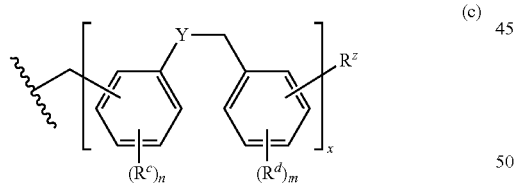

wherein:
Y is —O—, —S—, —NR$^Y$—, or an optionally substituted methylene group, wherein R$^Y$ is hydrogen, optionally substituted aliphatic, or an amino protecting group;
each instance of R$^c$ is independently —F, —Br, —I, —Cl, optionally substituted aliphatic, optionally substituted heteroaliphatic, optionally substituted carbocycyl, optionally substituted heterocycyl, optionally substituted aryl, optionally substituted heteroaryl, —OR$^e$, —SR$^e$, —NHR$^e$, and —N(R$^e$)$_2$, wherein each instance of R$^e$ is independently hydrogen, optionally substituted aliphatic, optionally substituted heteroaliphatic, optionally substituted carbocycyl, optionally substituted heterocycyl, optionally substituted aryl, or optionally substituted heteroaryl, or two R$^e$ groups are joined to form a 5- to 6-membered optionally substituted heterocycyl or optionally substituted heteroaryl ring;
each instance of R$^d$ is independently —F, —Br, —I, —Cl, optionally substituted aliphatic, optionally substituted heteroaliphatic, optionally substituted carbocycyl, optionally substituted heterocycyl, optionally substituted aryl, optionally substituted heteroaryl, —OR$^f$, —SR$^f$, —NHR$^f$, or —N(R$^f$)$_2$, wherein each instance of R$^f$ is independently hydrogen, optionally substituted aliphatic, optionally substituted heteroaliphatic, optionally substituted carbocycyl, optionally substituted heterocycyl, optionally substituted aryl, or optionally substituted heteroaryl, or two R$^f$ groups are joined to form a 5- to 6-membered optionally substituted heterocycyl or optionally substituted heteroaryl ring;
R$^z$ is hydrogen, —F, —Br, —I, —Cl, optionally substituted aliphatic, optionally substituted heteroaliphatic, optionally substituted carbocycyl, optionally substituted heterocycyl, optionally substituted aryl, optionally substituted heteroaryl, —OR$^g$, —SR$^g$, —NHR$^g$, or —N(R$^g$)$_2$, wherein each instance of R$^g$ is independently hydrogen, optionally substituted aliphatic, optionally substituted heteroaliphatic, optionally substituted carbocycyl, optionally substituted heterocycyl, optionally substituted aryl, or optionally substituted heteroaryl or two R$^g$ groups are joined to form a 5- to 6-membered optionally substituted heterocycyl or optionally substituted heteroaryl ring;
each instance of n is, independently, 0, 1, 2, 3, or 4;
each instance of m is, independently, 0, 1, 2, 3, or 4; and
x is 1, 2, 3, 4, 5, or 6.

As generally defined above, Y is —O—, —S—, —NR$^Y$—, or an optionally substituted methylene group, wherein R$^Y$ is hydrogen, optionally substituted aliphatic, or an amino protecting group. In certain embodiments, Y is —O—. In certain embodiments, Y is —S—. In certain embodiments, Y is —NR$^Y$—. In certain embodiments, Y is an optionally substituted methylene group, e.g., —CH$_2$—.

As generally defined above, each instance of R$^c$ is independently —F, —Br, —I, —Cl, optionally substituted aliphatic, optionally substituted heteroaliphatic, optionally substituted carbocycyl, optionally substituted heterocycyl, optionally substituted aryl, optionally substituted heteroaryl, —OR$^e$, —SR$^e$, —NHR$^e$, or —N(R$^e$)$_2$, wherein each instance of R$^e$ is independently hydrogen, optionally substituted aliphatic, optionally substituted heteroaliphatic, optionally substituted carbocycyl, heterocycyl, optionally substituted aryl, or optionally substituted heteroaryl, or two R$^e$ groups are joined to form a 5- to 6-membered optionally substituted heterocycyl or optionally substituted heteroaryl ring; and n is 0, 1, 2, 3, or 4.

In certain embodiments, each instance of R$^c$ is independently —F, —Br, —I, —Cl, optionally substituted aliphatic, optionally substituted heteroaliphatic, optionally substituted carbocycyl, optionally substituted heterocycyl, optionally substituted aryl, optionally substituted heteroaryl, —OR$^e$, —SR$^e$, —NHR$^e$, or —N(R$^e$)$_2$, wherein each instance of R$^e$ is independently hydrogen, optionally substituted aliphatic, optionally substituted heteroaliphatic, optionally substituted carbocycyl, optionally substituted heterocycyl, optionally substituted aryl, or optionally substituted heteroaryl, or two R$^e$ groups are joined to form a 5- to 6-membered optionally substituted heterocycyl or optionally substituted heteroaryl ring; wherein each instance of aliphatic, heteroaliphatic, carbocycyl, heterocycyl, aryl and heteroaryl is independently unsubstituted or substituted with 1, 2, 3, 4, 5, 6, 7, 8, 9, 10, or more substituents, as defined herein. In certain embodiments, each instance of aliphatic, heteroaliphatic, carbocycyl, heterocycyl, aryl and heteroaryl is independently unsubstituted or substituted with C$_{1-6}$alkyl, C$_{1-6}$fluoroalkyl or halogen.

In certain embodiments, each instance of R$^c$ is independently —F, aliphatic, heteroaliphatic, carbocycyl, heterocycyl, aryl, or heteroaryl, wherein each instance of aliphatic, heteroaliphatic, carbocycyl, heterocycyl, aryl and heteroaryl is independently unsubstituted or substituted with C$_{1-6}$alkyl, C$_{1-6}$fluoroalkyl or halogen.

In certain embodiments, each instance of R$^c$ is independently —F or alkyl, wherein each instance of alkyl is independently unsubstituted or substituted with C$_{1-6}$alkyl, C$_{1-6}$fluoroalkyl or halogen.

In certain embodiments, n is 0 or 1. In certain embodiments, n is 0. In certain embodiments, n is 1. In certain embodiments, n is 2.

As generally defined above, each instance of R$^d$ is independently —F, —Br, —I, —Cl, optionally substituted aliphatic, optionally substituted heteroaliphatic, optionally substituted carbocycyl, optionally substituted heterocycyl, optionally substituted aryl, optionally substituted heteroaryl, —OR$^f$, —SR$^f$, —NHR$^f$, or —N(R$^f$)$_2$, wherein each instance of R$^f$ is independently hydrogen, optionally substituted aliphatic, optionally substituted heteroaliphatic, optionally substituted carbocycyl, optionally substituted heterocycyl, optionally substituted aryl, or optionally substituted heteroaryl, or two R$^f$ groups are joined to form a 5- to 6-membered optionally substituted heterocycyl or optionally substituted heteroaryl ring; and m is 0, 1, 2, 3, or 4.

In certain embodiments, each instance of R$^d$ is independently —F, —Br, —I, —Cl, optionally substituted aliphatic, optionally substituted heteroaliphatic, optionally substituted carbocycyl, optionally substituted heterocycyl, optionally substituted aryl, optionally substituted heteroaryl, —OR$^f$, —SR$^f$, —NHR$^f$, or —N(R$^f$)$_2$, wherein each instance of R$^f$ is independently hydrogen, optionally substituted aliphatic, optionally substituted heteroaliphatic, optionally substituted carbocycyl, optionally substituted heterocycyl, optionally substituted aryl, or optionally substituted heteroaryl, or two R$^f$ groups are joined to form a 5- to 6-membered optionally substituted heterocycyl or optionally substituted heteroaryl ring; wherein each instance of aliphatic, heteroaliphatic, carbocycyl, heterocycyl, aryl and heteroaryl is independently unsubstituted or substituted with 1, 2, 3, 4, 5, 6, 7, 8, 9, 10, or more substituents, as defined herein. In certain embodiments, each instance of aliphatic, heteroaliphatic, carbocycyl, heterocycyl, aryl and heteroaryl is independently unsubstituted or substituted with C$_{1-6}$alkyl, C$_{1-6}$fluoroalkyl or halogen.

In certain embodiments, each instance of R$^d$ is independently —F, aliphatic, heteroaliphatic, carbocycyl, heterocycyl, aryl, or heteroaryl, wherein each instance of aliphatic, heteroaliphatic, carbocycyl, heterocycyl, aryl, and heteroaryl is independently unsubstituted or substituted with C$_{1-6}$alkyl, C$_{1-6}$fluoroalkyl or halogen.

In certain embodiments, each instance of R$^d$ is independently —F or alkyl, wherein each instance of alkyl is independently unsubstituted or substituted with C$_{1-6}$alkyl, C$_{1-6}$fluoroalkyl, or halogen.

In certain embodiments, m is 0 or 1. In certain embodiments, m is 0. In certain embodiments, m is 1. In certain embodiments, m is 2.

In certain embodiments, R$^z$ is an ortho, meta, or para substituent to the —OCH$_2$-linking group. In certain embodiments, R$^z$ is a meta substituent.

As generally defined above, R$^z$ is hydrogen, —F, —Br, —I, —Cl, optionally substituted aliphatic, heteroaliphatic, optionally substituted carbocycyl, optionally substituted heterocycyl, optionally substituted aryl, optionally substituted heteroaryl, —OR$^g$, —SR$^g$, —NHR$^g$, or —N(R$^g$)$_2$, wherein each instance of R$^g$ is independently hydrogen, optionally substituted aliphatic, optionally substituted heteroaliphatic, optionally substituted carbocycyl, optionally substituted heterocycyl, optionally substituted aryl, or optionally substituted heteroaryl or two R$^g$ groups are joined to form a 5- to 6-membered optionally substituted heterocycyl or optionally substituted heteroaryl ring.

In certain embodiments, R$^z$ is hydrogen, —F, —Br, —I, —Cl, optionally substituted aliphatic, heteroaliphatic, optionally substituted carbocycyl, optionally substituted heterocycyl, optionally substituted aryl, optionally substituted heteroaryl, —OR$^g$, —SR$^g$, —NHR$^g$, or —N(R$^g$)$_2$, wherein each instance of R$^g$ is independently hydrogen, optionally substituted aliphatic, optionally substituted heteroaliphatic, optionally substituted carbocycyl, optionally substituted heterocycyl, optionally substituted aryl, or optionally substituted heteroaryl or two R$^g$ groups are joined to form a 5- to 6-membered optionally substituted heterocycyl or optionally substituted heteroaryl ring, wherein each instance of aliphatic, heteroaliphatic, carbocycyl, heterocycyl, aryl and heteroaryl is independently unsubstituted or substituted with 1, 2, 3, 4, 5, 6, 7, 8, 9, 10, or more substituents, as defined herein. In certain embodiments, each instance of aliphatic, heteroaliphatic, carbocycyl, heterocycyl, aryl and heteroaryl is independently unsubstituted or substituted with C$_{1-6}$alkyl, C$_{1-6}$fluoroalkyl or halogen.

In certain embodiments, R$^z$ is hydrogen, alkyl, alkenyl, alkynyl, carbocycyl, heterocycyl, aryl, heteroaryl, —OR$^g$, —SR$^g$, —NHR$^g$, or —N(R$^g$)$_2$, wherein each instance of R$^g$ is independently hydrogen, alkyl, alkenyl, alkynyl, carbocycyl, heterocycyl, aryl, heteroaryl, or two $R^g$ groups are joined to form a 5- to 6-membered heterocycyl or heteroaryl ring, and wherein each instance of alkyl, alkenyl, alkynyl, carbocycyl, heterocycyl, aryl, and heteroaryl, is independently unsubstituted or substituted with $C_{1-6}$alkyl, $C_{1-6}$fluoroalkyl or halogen.

In certain embodiments, $R^z$ is hydrogen or aryl, wherein aryl is unsubstituted or substituted with $C_{1-6}$alkyl, $C_{1-6}$fluoroalkyl or halogen.

As generally depicted above, x is 1, 2, 3, 4, 5, or 6. In certain embodiments, x is 1 or 2. In certain embodiments, x is 1. In certain embodiments, x is 2.

It is understood that each repeat unit of formula (c), when x is greater than 1, can optionally differ from one another, arising from differences in the independent variables Y, $R^c$, $R^d$, n and m, as well as different substitution patterns on and between each repeating unit. Thus, in further defining the compounds of the present invention, it is also generally helpful to further designate Y, $R^c$, $R^d$, n and m, with a sequential number corresponding to the first, second, third, fourth, fifth or sixth sequential group from which it is formally a member, e.g., Y, $R^c$, $R^d$, n, m and x can also be referred to as $Y^1 R^{c1}$, $R^{d1}$, n1 and m1 for the first group in the sequence; $Y^2$, $R^{c2}$, $R^{d2}$, n2 and m2 for the second optional repeating unit in the sequence; $Y^3$, $R^{c3}$, $R^{d3}$, n3 and m3 for the third optional repeating unit in the sequence; $Y^4$, $R^{c4}$, $R^{d4}$, n4 and m4 for the fourth optional repeating unit in the sequence; $Y^5$, $R^{c5}$, $R^{d5}$, n5 and m5 for the fifth optional repeating unit in the sequence; and $Y^6$, $R^{c6}$, $R^{d6}$, n6 and m6 for the sixth optional repeating unit in the sequence.

For example, in certain embodiments, the group of Formula (c) is of the formula:

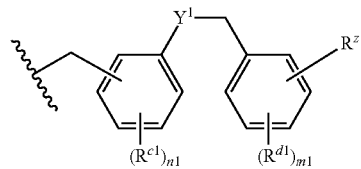

wherein x is 1;

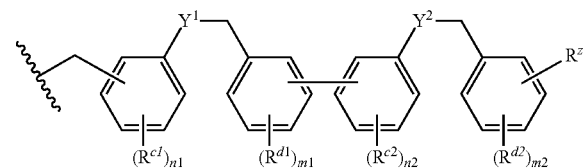

wherein x is 2;

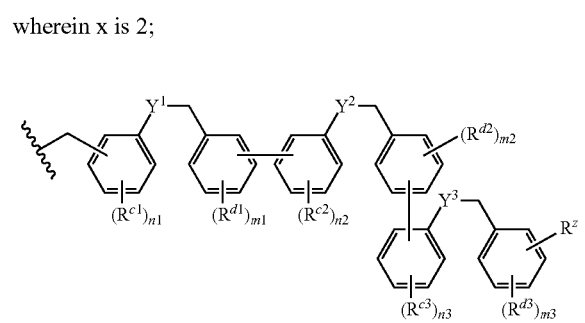

wherein x is 3;

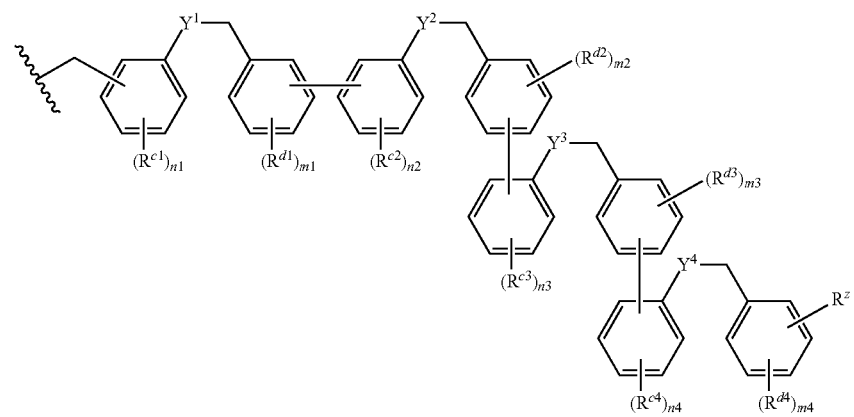

wherein x is 4;

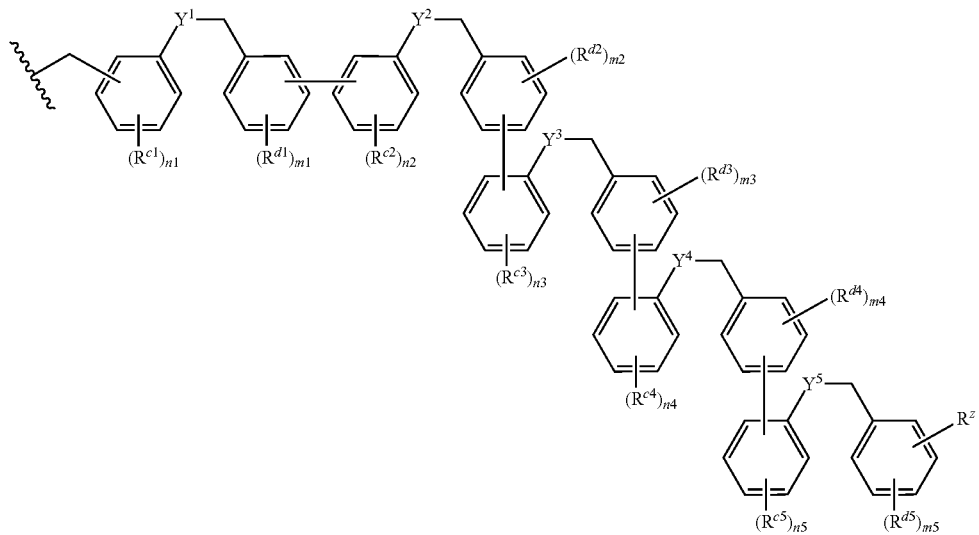

wherein x is 5; or

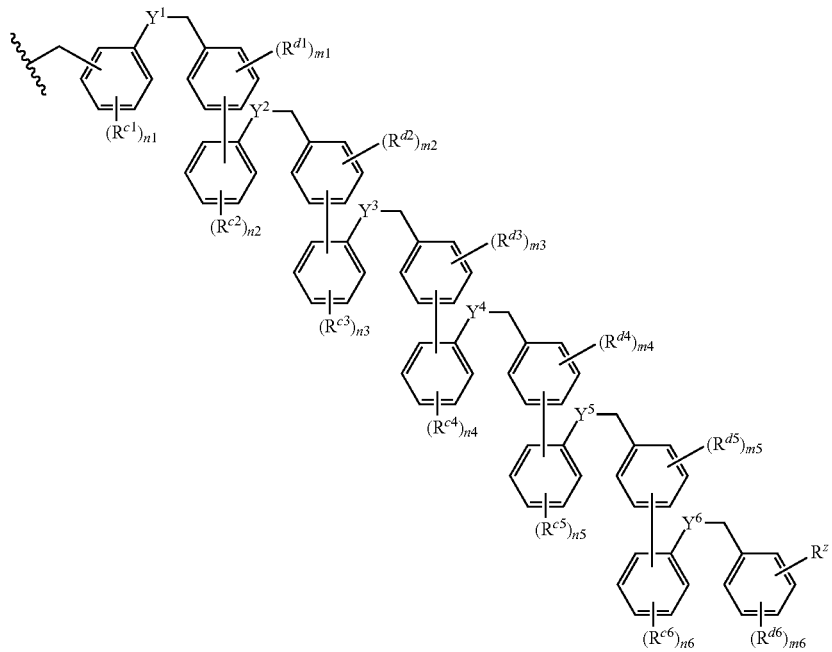

wherein x is 6;
wherein:
$R^{c1}$, $R^{c2}$, $R^{c3}$, $R^{c4}$, $R^{c5}$, and $R^{c6}$ each independently correspond to the definition and various embodiments of $R^c$;

$R^{d1}$, $R^{d2}$, $R^{d3}$, $R^{d4}$, $R^{d5}$, and $R^{d6}$ each independently correspond to the definition and various embodiments of $R^d$;

n1, n2, n3, n4, n5, and n6 each independently correspond to the definition and various embodiments of n;

m1, m2, m3, m4, m5, and m6 each independently correspond to the definition and various embodiments of m;

$Y^1$, $Y^2$, $Y^3$, $Y^4$, $Y^5$, and $Y^6$, each independently correspond to the definition and various embodiments of Y; and $R^z$ is as defined herein.

In certain embodiments, the group of Formula (c) is of the formula:

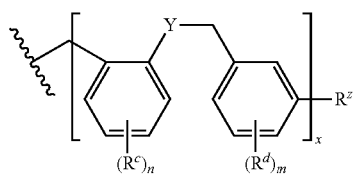

wherein Y, $R^z$, $R^c$, $R^d$, m, n, and x are as defined herein.

In certain embodiments, the group of Formula (c) is:
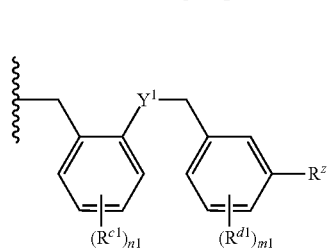
wherein x is 1;
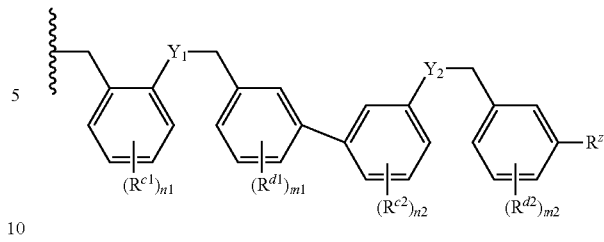
wherein x is 2;
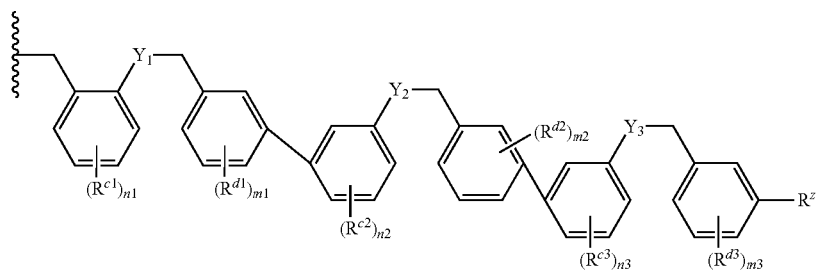
wherein x is 3:
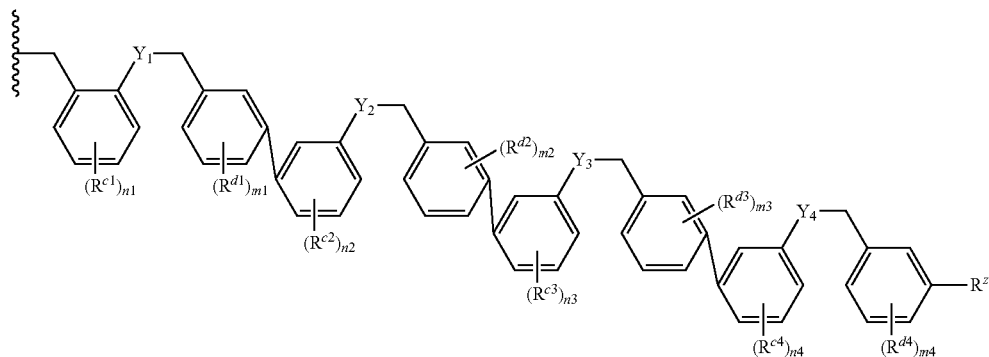
wherein x is 4;
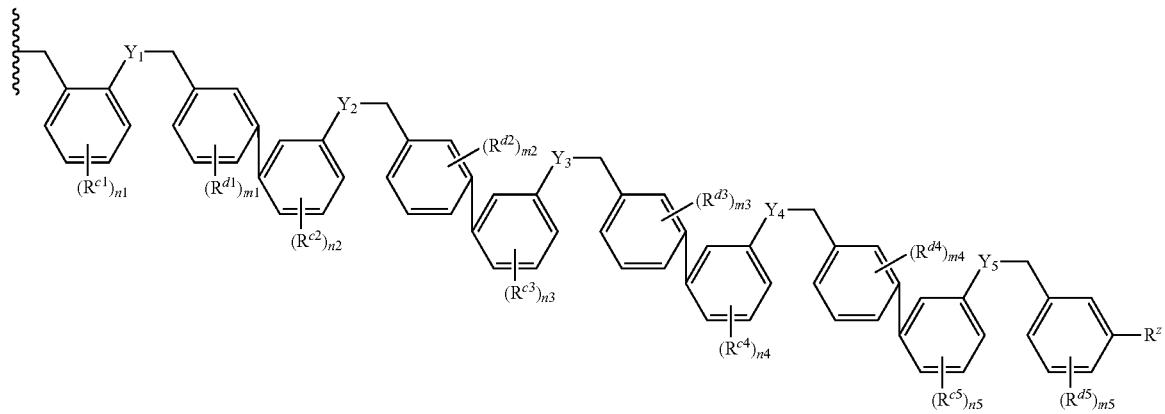
wherein x is 5; or

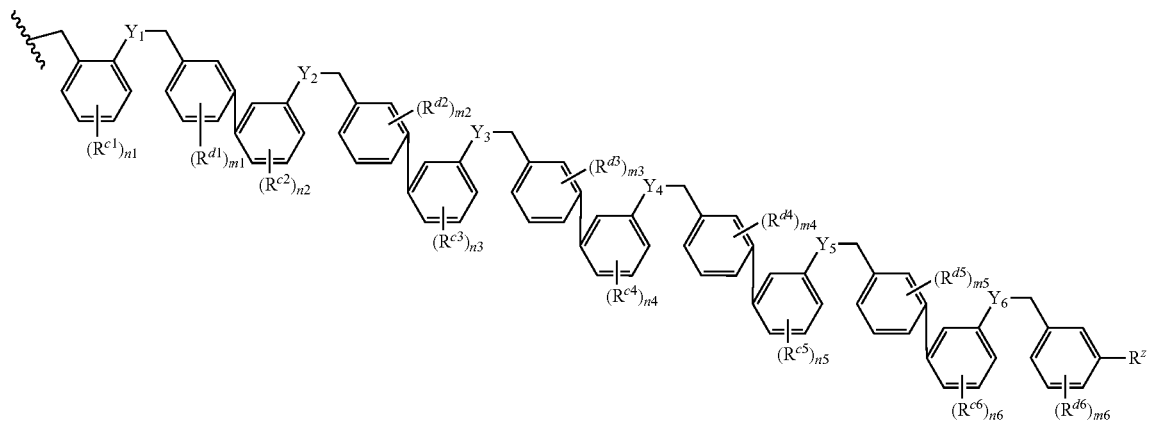

wherein x is 6;
wherein:

$R^{c1}$, $R^{c2}$, $R^{c3}$, $R^{c4}$, $R^{c5}$, and $R^{c6}$ each independently correspond to the definition and various embodiments of $R^c$;

$R^{d1}$, $R^{d2}$, $R^{d3}$, $R^{d4}$, $R^{d5}$, and $R^{d6}$ each independently correspond to the definition and various embodiments of $R^d$;

n1, n2, n3, n4, n5, and n6 each independently correspond to the definition and various embodiments of n;

m1, m2, m3, m4, m5, and m6 each independently correspond to the definition and various embodiments of m;

$Y^1$, $Y^2$, $Y^3$, $Y^4$, $Y^5$, and $Y^6$, each independently correspond to the definition and various embodiments of Y;

and $R^z$ is as defined herein.

In certain embodiments, each of n, n1, n2, n3, n4, n5, and n6 is 0.

In certain embodiments, each of m, m1, m2, m3, m4, m5, and m6 is 0.

In certain embodiments, each of Y, $Y^1$, $Y^2$, $Y^3$, $Y^4$, $Y^5$, and $Y^6$ and —O—.

Specifically Contemplated Embodiments

Compounds of the present invention specifically contemplated include, but are not limited to, compounds having the following structure:

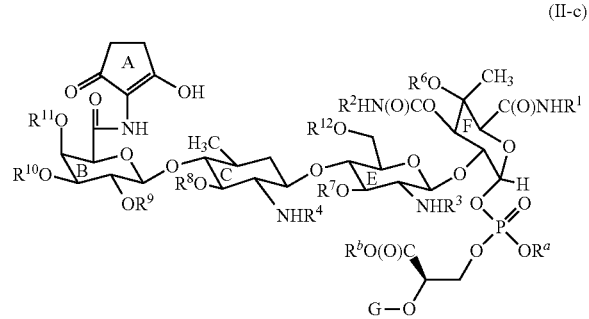

(II-c)

or a pharmaceutically acceptable form thereof;
wherein G is selected from the group consisting of

Pharmaceutical Compositions

The present invention also provides pharmaceutical compositions comprising an effective amount of a compound of Formula (I), (II), (III), or (IV), or a pharmaceutically acceptable form thereof, and, optionally, a pharmaceutically acceptable excipient.

Pharmaceutically acceptable excipients include any and all solvents, diluents or other liquid vehicles, dispersion or suspension aids, surface active agents, isotonic agents, thickening or emulsifying agents, preservatives, solid binders, lubricants and the like, as suited to the particular dosage form desired. General considerations in formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy*, 21st Edition (Lippincott Williams & Wilkins, 2005).

Pharmaceutical compositions described herein can be prepared by any method known in the art of pharmacology. In general, such preparatory methods include the steps of bringing the compound of the present invention (the "active ingredient") into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite (aluminum silicate) and Veegum (magnesium aluminum silicate)), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate (Tween 20), polyoxyethylene sorbitan (Tween 60), polyoxyethylene sorbitan monooleate (Tween 80), sorbitan monopalmitate (Span 40), sorbitan monostearate (Span 60), sorbitan tristearate (Span 65), glyceryl monooleate, sorbitan monooleate (Span 80)), polyoxyethylene esters (e.g. polyoxyethylene monostearate (Myrj 45), polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether (Brij 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F-68, Poloxamer P188, cetrimonium bromide, cetylpyridinium chloride, benzalkonium chloride, docusate sodium, etc. and/or combinations thereof.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of fish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, etc., and/or combinations thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an antioxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor, alcohols, oils, modified oils, glycols, polysorbates, cyclodextrins, polymers, and combinations thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the conjugates of this invention with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinyl-pyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredients can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Dosage forms for topical and/or transdermal administration of a compound of this invention may include ointments, pastes, creams, lotions, gels, powders, solutions, sprays, inhalants and/or patches. Generally, the active ingredient is admixed under sterile conditions with a pharmaceutically acceptable carrier and/or any needed preservatives and/or buffers as can be required. Additionally, the present invention contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes can be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition of the invention can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant can be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) and as much as 100% (w/w) of the active ingredient, and may comprise one or more of the additional ingredients described herein. A pharmaceutical composition of the invention can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition of the invention can be prepared, packaged, and/or sold in a formulation for ophthalmic administration. Such formulations may, for example, be in the form of eye drops including, for example, a 0.1/1.0% (w/w) solution and/or suspension of the active ingredient in an aqueous or oily liquid carrier. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this invention.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Still further encompassed by the invention are kits (e.g., pharmaceutical packs). The kits provided may comprise an inventive pharmaceutical composition or compound and a container (e.g., a vial, ampule, bottle, syringe, and/or dispenser package, or other suitable container). In some embodiments, provided kits may optionally further include a second container comprising a pharmaceutical excipient for dilution or suspension of an inventive pharmaceutical composition or compound. In some embodiments, the inventive pharmaceutical composition or compound provided in the container and the second container are combined to form one unit dosage form.

Optionally, a single container may comprise one or more compartments for containing an inventive pharmaceutical composition or compound, and/or a pharmaceutically acceptable excipient for suspension or dilution. In some embodiments, a single container can be appropriate for modification such that the container may receive a physical modification so as to allow combination of compartments and/or components of individual compartments. For example, a foil or plastic bag may comprise two or more compartments separated by a perforated seal which can be broken so as to allow combination of contents of two individual compartments once the signal to break the seal is generated. A kit may thus comprise such multi-compartment containers providing an inventive pharmaceutical composition or compound and one or more pharmaceutically acceptable excipients.

Optionally, instructions for use are additionally provided in such kits of the invention. Such instructions may provide, generally, for example, instructions for dosage and administration. In other embodiments, instructions may further provide additional detail relating to specialized instructions for particular containers and/or systems for administration. Still further, instructions may provide specialized instructions for use in conjunction and/or in combination with an additional therapeutic agent.

Methods of Use and Treatment

The present invention also provides methods of treating or preventing an infection comprising administering to a subject an effective amount a compound of Formula (I), (II), (III), or (IV), or a pharmaceutically acceptable form thereof. In certain embodiments, the infection is a bacterial infection. In certain embodiments, the bacterial infection is caused by a Gram-positive bacterium. In certain embodiments, the bacterial infection is caused by a Gram-negative bacterium.

The present invention also provides methods of inhibiting microbial growth, e.g., bacterial, viral, parasitic, or fungal growth, comprising contacting a microbial organism, e.g., a bacterium, a virus, a parasite, or a fungus, with an effective amount of a compound of Formula (I), (II), (III), or (IV), or a pharmaceutically acceptable form thereof. In certain embodiments, the method is an in vitro or in situ method. In certain embodiments, the microbial organism is a bacterium. In certain embodiments, the bacterium is a Gram-positive bacterium. In certain embodiments, the bacterium is a Gram-negative bacterium.

In certain embodiments, the bacterial infection being treated or prevented is caused by Gram-negative bacteria. Exemplary Gram-negative bacteria include, but are not limited to, *Escherichia coli, Salmonella* (e.g., *Salmonella enteritidis*, and *Salmonella typhi*), *Hemophilus influenzae, Klebsiella pneumoniae, Legionella pneumophila, Pseudomonas aeruginosa, Proteus mirabilis, Enterobacter cloacae, Serratia marcescens, Helicobacter pylori, Pseudomonas, Moraxella* (e.g., *Moraxella catarrhalis*), *Helicobacter, Stenotrophomonas, Bdellovibrio*, acetic acid bacteria, *Legionella*, and *Neisseria* (e.g., *Neisseria gonorrhoeae, Neisseria meningitidis*).

In certain embodiments, the infection being treated or prevented is caused by Gram-positive bacteria. Exemplary Gram-positive bacteria include, but are not limited to, Streptococci bacteria such as *Streptococcus* Group A, *Streptococcus* Group B, *Streptococcus* Group G (e.g., *Streptococcus anginosus, Streptococcus pneumoniae*), *Streptococcus viridans, Streptococcus pyogenes* (e.g., ATCC8668); Staphylococci bacteria such as *Staphylococcus aureaus* (e.g., *Staphylococcus aureus* (e.g., ATCC29213), *Staphylococcus aureus* (e.g., ATCC43300) MSA), and *Staphylococcus saprophyticus; Micrococcus* bacteria such as *Micrococcus luteus* (e.g., ATCC272); and *Enterococcus* bacteria such as *Enterococcus faecalis* (e.g., ATCC29212) and *Enterococcus faecalis* (e.g., ATCC51299).

In certain embodiments, the bacterial infection being treated or prevented is caused by vancomycin-resistant bacteria. In certain embodiments, the bacterial infection is caused by vancomycin-resistant Gram-negative or Gram-positive bacteria. In certain embodiments, the bacterial infection is caused by vancomycin-resistant Gram-positive bacteria. In certain embodiments, the bacterial infection is caused by vancomycin-resistant *Staphylococcus aureus*. In certain embodiments, the bacterial infection is caused by vancomycin-resistant Gram-positive enterococci (VRE). In certain embodiments, the bacterial infection is caused by methicillin-resistant bacteria. In certain embodiments, the bacterial infection is caused by methicillin-resistant *Staphylococcus aureus* (MRSA).

The compounds and pharmaceutical compositions described herein may be used to treat any infection including, but not limited to, anthrax, bacterial meningitis, botulism, brucellosis, campylobacteriosis, cholera, diphtheria, gonorrhea, impetigo, legionellosis, leprosy (Hansen's disease), leptospirosis, listeriosis, lyme disease, melioidosis, MRSA infection, nocardiosis, pertussis (whooping cough), plague, pneumococcal pneumonia, psittacosis, Q fever, rocky mountain spotted fever (RMSF), scarlet fever, shigellosis, syphilis, tetanus, trachoma, tuberculosis, tularemia, typhoid fever, typhus, urinary tract infection (UTI), skin infections, gastrointestinal infections, genito-urinary infections, and systemic infections.

Particularly useful compounds of the present invention include those with biological activity. In certain embodiments, the compounds of the invention exhibit antibacterial activity. For example, the compound may have a mean inhibitory concentration, with respect to a particular bacteria, of less than 50 µg/mL, less than 25 µg/mL, less than 5 µg/mL, or less than 1 µg/mL.

A method for treating an infection is provided comprising administering an effective amount of an inventive compound, or a pharmaceutical composition thereof, to a subject in need thereof, in such amounts and for such time as is necessary to achieve the desired result.

The compounds and compositions for use in methods of the present invention may be administered in such amounts, time, and route deemed necessary in order to achieve the desired result. The exact amount required will vary from subject to subject, depending on the species, age, and general condition of the subject, the severity of the infection, the particular compound, its mode of administration, its mode of activity, and the like. The compounds of the invention are preferably formulated in dosage unit form for ease of administration and uniformity of dosage. It will be understood, however, that the total daily usage of the compounds and compositions of the present invention will be decided by the attending physician within the scope of sound medical judgment. The specific therapeutically effective dose level for any particular subject will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

In some embodiments, an effective amount of an inventive compound is delivered to the subject prior to, simultaneously with, and/or after diagnosis of an infection. In some embodiments, a therapeutic amount of an inventive composition is delivered to the subject prior to, simultaneously with, and/or after onset of symptoms associated with an infection. In some embodiments, the amount of inventive compound is sufficient to treat, alleviate, ameliorate, relieve, delay onset of, inhibit progression of, reduce severity of, and/or reduce incidence of one or more symptoms or features associated with the infection.

The inventive compounds and compositions of the present invention may be administered by any route. In some embodiments, the inventive compounds and compositions are administered via a variety of routes, including oral, intravenous, intramuscular, intraarterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, enteral, sublingual; by intratracheal instillation, bronchial instillation, and/or inhalation; and/or as an oral spray, nasal spray, and/or aerosol. Specifically contemplated routes are systemic intravenous injection, regional administration via blood and/or lymph supply, and/or direct administration to an affected site. In general the most appropriate route of administration will depend upon a variety of factors including the nature of the agent (e.g., its stability in the environment of the gastrointestinal tract), the condition of the subject (e.g., whether the subject is able to tolerate oral administration), etc. At present the oral and/or nasal spray and/or aerosol route is most commonly used to deliver therapeutic agents directly to the lungs and/or respiratory system. However, the invention encompasses the delivery of the inventive pharmaceutical composition by any appropriate route taking into consideration likely advances in the sciences of drug delivery.

The exact amount of a compound required to achieve an effective amount at a desired site in the subject will vary from subject to subject, depending on species, age, and general condition of a subject, severity of the side effects or disorder, identity of the particular compound(s), mode of administration, and the like. In certain embodiments of the present invention, an effective amount of an inventive compound for administration one or more times a day to a 70 kg adult human may comprise about 0.001 mg/kg to about 100 mg/kg of an inventive compound per unit dosage form. It will be appreciated that dose ranges as described herein provide guidance for the administration of inventive pharmaceutical compositions to an adult. The amount to be administered to, for example, a child or an adolescent can be determined by a medical practitioner or person skilled in the art and can be lower or the same as that administered to an adult.

In certain embodiments, the compounds of the invention may be administered at dosage levels sufficient to deliver from about 0.001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, and from about 1 mg/kg to about 25 mg/kg, of subject body weight per day, one or more times a day, to obtain the desired therapeutic effect. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations).

It will be also appreciated that an inventive compound or composition thereof, as described above and herein, can be administered in combination with one or more additional therapeutically active agents ("agent"). By "in combination with," it is not intended to imply that the compound and agent must be administered at the same time and/or formulated for delivery together, although these methods of delivery are within the scope of the invention. The inventive compound can be administered concurrently with, prior to, or subsequent to, the administration an agent. In general, each compound or agent used in combination will be administered at a dose and/or on a time schedule determined for that compound or agent.

In will further be appreciated that the additional therapeutically active agent utilized in this combination may be administered together in a single composition or administered separately in different compositions.

In general, it is expected that additional therapeutically active agents utilized in combination be utilized at levels that do not exceed the levels at which they are utilized individually. In some embodiments, the levels utilized in combination will be lower than those utilized individually.

The particular combination to employ in a regimen will take into account compatibility of the inventive compound with the additional therapeutically active agent and/or the desired therapeutic effect to be achieved.

It will also be appreciated that the therapy employed may achieve a desired effect for the same disorder (for example, an inventive compound may be administered in combination with another antibacterial agent), and/or they may achieve different effects (e.g., control of any adverse effects). For example, an agent may improve the bioavailability, reduce and/or modify the metabolism, inhibit the excretion, and/or modify the distribution of the inventive compound within the body of the subject.

Therapeutically active agents include, but are not limited to, organic molecules that are drug compounds, peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, and vitamins. Therapeutically active agents include any substance used as a medicine for treatment, prevention, delay, reduction or amelioration of a disease, condition, or disorder, and refers to a substance that is useful for therapy, including prophylactic and therapeutic treatment. A therapeutically active agent also includes a compound that increases the effect or effectiveness of another compound, for example, by enhancing potency or reducing adverse effects of the other compound.

For example, in certain embodiments, an additional therapeutically active agent is another antibacterial agent. Exemplary antibacterial agents include, but are not limited to, aminoglycosides, glycoproteins (e.g. vancomycin, teicoplanin), penicillins, cephalosporins, carbapenems (e.g., imipenem, cilastin, ertapenem), chloramphenicol, macrolides (e.g., erythromycin), lincosamides (e.g., lincomycin, clindamycin), fusidic acid, tetracyclines, streptogramins, quinolones (e.g., fluoroquinolones, ciprofloxacin, levofloxacin), rifampicin, nitrofurans, polymyxins, daptomycin, sulphonamides, diaminopyrimidines etc.

Methods of Synthesis

As generally described above, the present invention provides compounds of Formula (I), (II), (III), and (IV), wherein the sugar portion comprising Rings E and F, and optionally Rings A, B, C, and D, is derived from moenomycin A. Thus, in certain embodiments, the present invention provides methods of synthesis of these compounds from the natural product moenomycin A. The methods described herein include the use of synthetic methods (i.e., building up, adding groups) as well as degradative methods (i.e., breaking down, removing groups) to arrive at compounds of the present invention. For example, Rings A, B, C and/or D of moenomycin A may optionally be cleaved using one or more degradative steps. The degraded compound may then be further synthetically modified (e.g., using a combination of degradative and synthetic steps) to provide a compound of Formula (I), (II), (III), or (IV).

In one aspect, the present invention provides a method of synthesizing a compound of Formula (II) comprising the steps of:

(i) providing moenomycin A;

(ii) removing the phosphoglycerate linker and moenocinol chain of moenomycin A, and optionally Rings A and/or D, to provide a saccharide group of Formula (II-S1):

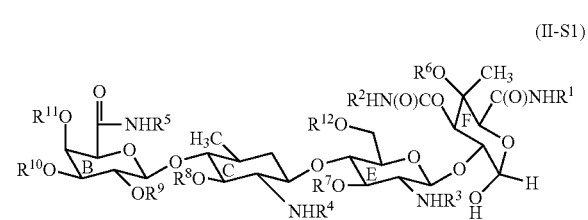

(II-S1)

wherein $R^1$, $R^2$, $R^3$, $R^4$, $R^5$, $R^6$, $R^7$, $R^8$, $R^9$, $R^{10}$, $R^{11}$, and $R^{12}$ are as defined herein;

(iii) reacting (II-S1) with a phosphitylation agent to provide a H-phosphonate diester of Formula (II-S2):

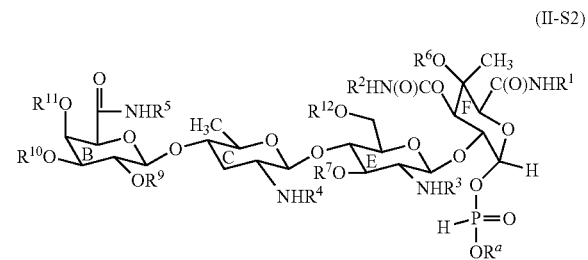

(II-S2)

wherein $R^a$ is as defined herein; and (iv) coupling (II-S2) with a compound of Formula (P1):

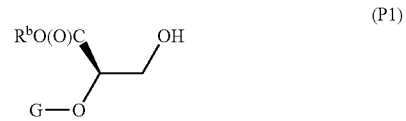

(P1)

wherein $R^b$ and G are as defined herein, to provide a compound of Formula (II) or a pharmaceutically acceptable form thereof.

In another aspect, the present invention provides a method of synthesizing a compound of Formula (III) comprising the steps of:

(i) providing moenomycin A;

(ii) removing the phosphoglycerate linker, moenocinol chain, and Rings A and B of moenomycin A, and optionally Ring D, to provide a saccharide group of Formula (III-S1):

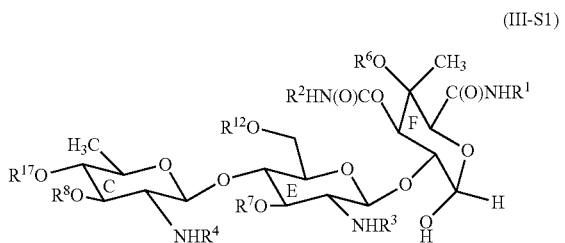
(III-S1)

wherein $R^1$, $R^2$, $R^3$, $R^4$, $R^6$, $R^7$, $R^8$, $R^{17}$, and $R^{12}$ are as defined herein;

(iii) reacting (III-S1) with a phosphitylation agent to provide a H-phosphonate diester of the formula (III-S2):

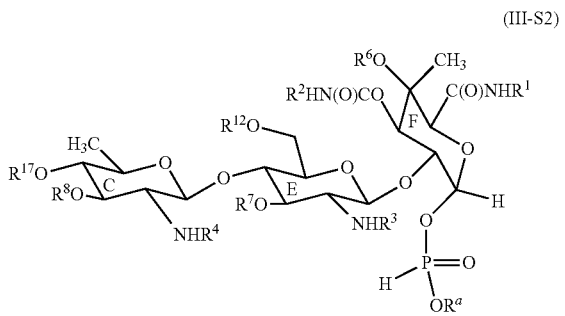
(III-S2)

wherein $R^a$ is as defined herein; and (iv) coupling (III-S2) with a compound of Formula (P1):

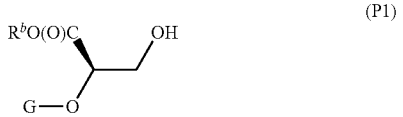
(P1)

wherein $R^b$ and G are as defined herein, to provide a compound of Formula (III), or a pharmaceutically acceptable form thereof.

In yet another aspect, the present invention provides a method of synthesizing a compound of Formula (IV) comprising the steps of:
(i) providing moenomycin A;
(ii) removing the phosphoglycerate linker, moenocinol chain, and Rings A, B and C of moenomycin A, and optionally Ring D, to provide a saccharide group of Formula (IV-S1):

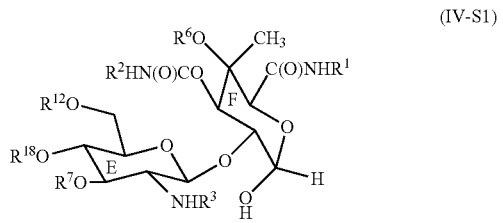
(IV-S1)

wherein $R^1$, $R^2$, $R^3$, $R^6$, $R^7$, $R^{18}$, and $R^{12}$ are as defined herein;
(iii) reacting (IV-S1) with a phosphitylation agent to provide an H-phosphonate diester of Formula (IV-S2):

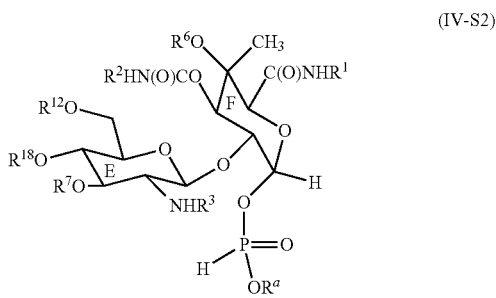
(IV-S2)

wherein $R^a$ is as defined herein; and
(iv) coupling (IV-S2) with a compound of Formula (P1):

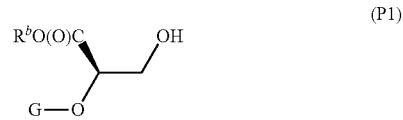
(P1)

wherein $R^b$ and G are as defined herein, to provide a compound of Formula (IV), or a pharmaceutically acceptable form thereof.

In certain embodiments, step (ii) of the any of the above methods comprises removing the moenocinol chain, followed by removal of the phosphoglycerate linker.

In certain embodiments, step (ii) comprises removing the moenocinol chain using a Lewis acid. Exemplary Lewis acids include, but are not limited to, $AlCl_3$, $BF_3OEt_3$, and TMSOTf.

In certain embodiments, step (ii) comprises removing the phosphoglycerate linker using a base. In certain embodiments, the base is an inorganic base. Exemplary inorganic bases include, but are not limited to, NaOH, KOH, LiOH, $Ca(OH)_2$, $Mg(OH)_2$, $Na_2CO_3$, $NaHCO_3$, $K_2CO_3$ and $KHCO_3$.

Phosphitylation agents are well-known reagents in the art; see Garegg et al., Chem. Scr. (1985) 25:280-282 and Westerduin et al., Tet. Lett. (1986) 27:6271-6274, incorporated herein by reference. Exemplary phosphitylation agents include, but are not limited to, 2-benzo[d]-1,2-oxaphosphophepin-2,5-dione compounds (e.g., 2-methoxybenzo[d]-1,3,2-dioxaphosphorin-4-one, 2-chloro-benzo[d]-1,3,2-dioxaphosphorin-4-one, 2-R-benzo[d]-1-1,3,2-dioxaphosphorin-4-one), and tris(1,1,1,3,3,3-hexafluoro-2-propyl)phosphite.

In certain embodiments, step (ii) of any of the above methods comprises removing Rings A, B, C and/or D of moenomycin A. In certain embodiments, step (ii) of the above methods comprises first removing Rings A, B, C and/or D of moenomycin A, followed by removing the moenocinol chain, followed by removal of the phosphoglycerate linker. In certain embodiments, the step of removing Rings A, B, C and/or D comprises one or more enzymatic degradative reactions. In certain embodiments, the step of removing Rings A, B, C and/or D comprises a combination of enzymatic degradative and enzymatic synthetic reactions.

Examples of enzymatic degradative reactions are well known in the art; see for example, U.S. Pat. Nos. 5,206,405; 5,260,206; 5,315,038; and 5,506,140, each of which is incorporated herein by reference. For example, the enzymatic degradative step may be catalyzed by an enzyme (e.g., lipase, esterase, transferase, etc.). The enzymatic degradative step may be accomplished using an enzyme, a cell lysate, a cell, a cell culture, or the like. The cell or enzyme may be a wild-type or genetically engineered cell or enzyme.

Examples of enzymatic synthetic reactions useful in preparing the inventive compounds are also known in the art; see for example, WO 2008/021367, incorporated herein by reference. For example, the enzymatic synthetic step may be catalyzed by an enzyme (e.g., lipase, esterase, ligase, synthase, transferase, epimerase, etc.). The enzymatic synthetic step may be accomplished using an enzyme, using a cell lysate, using a cell, using a cell culture, or the like. The cell or enzyme may be a wild-type or genetically engineered cell or enzyme.

In certain embodiments, step (iv) of any of the above methods comprises coupling a H-phosphonate diester with a compound of the formula (P1). In certain embodiments, the method comprises use of a coupling agent used in H-phosphate chemistry; e.g., see Stawinski, In *Handbook of Organophosphorus Chemistry*, R. Engel (Ed.), pp. 377-434, Marcel Dekker, New York (1992), and Kraszewski and Stawinski, *Trends Org. Chem.* (2003) 10:1, incorporated herein by reference. Exemplary coupling reagents include, but are not limited to, adamantanecarbonyl chloride and 1,3-dimethyl-2-chloro-imidazolinium chloride (DMCI).

EXAMPLES

In order that the invention described herein may be more fully understood, the following examples are set forth. It should be understood that these examples are for illustrative purposes only and are not to be construed as limiting this invention in any manner.

Synthetic Methods
Preparation of 2,5-Di-O-Alkyl-D-Mannitol

To a stirred suspension of 60% NaH (3 equiv.), washed twice with petroleum ether, in anhydrous DMF (8 mL/mmol-starting material (SM)) was added 1,3:4,6-di-O,O-(4-methoxybenzylidene)-D-mannitol (1 equiv., SM) at room temperature. After being stirred for 30 min, the mixture was treated with a 1.2 M solution of alkylating reagents (2.4 equiv., Br, Cl, and methane- or p-toluene-sulfonate for R=allyl, benzyl, and n-alkyl groups, respectively) in anhydrous DMF and a catalytic amount of tetrabutylammonium iodide for allyl-Br, bromide for benzyl-Cl, or 15-Crown-5 for n-alkyl sulfonates. The resulting mixture was stirred for 18 h at rt for allyl-Br and benzyl-Cl or 70° C. for n-alkyl sulfonates, and then poured into sat. aq. $NH_4Cl$ (8 mL/mmol-SM). The immiscible mixture was extracted twice with $Et_2O$ and the combined organic phases were washed with water, brine, dried over $MgSO_4$, and then concentrated in vacuo. The crude ether was used for the next reaction without further purification.

For allyl and benzyl derivatives, a stirred solution of the residue in THF-$H_2O$ (4:1, 8 mL/mmol-SM) was treated with AcOH (170 equiv.) at room temperature. After being stirred at 55° C. for 2 d, the mixture was cooled to 0° C. and basified with 4 M aq. $K_2CO_3$ (90 equiv.). The immiscible mixture was extracted twice with $CHCl_3$ and the combined organic phases were washed with brine, dried over $MgSO_4$, and then concentrated in vacuo. The residue was purified by silica gel chromatography (petroleum ether:EtOAc=1:3 to 0:1) to give 2,5-di-O-allyl or benzyl-D-mannitol.

For n-alkyl derivatives, a stirred solution of the residue in EtOH (12 mL/mmol-SM) was treated with 3 M aq. HCl (12 equiv.) at room temperature. After being stirred at 70° C. for 3 h, the mixture was cooled to room temperature and basified with 4 M aq. $K_2CO_3$ (16 equiv.). The immiscible mixture was extracted twice with $CHCl_3$ and the combined organic phases were washed with brine, dried over $MgSO_4$, and then concentrated in vacuo. The residue was purified by recrystallization from $Et_2O$/EtOAc to give 2,5-di-O-n-alkyl-D-mannitol.

Preparation of Methyl 2-O-Alkyl-D-Glycerate

To a 5.5 M solution of 2,5-di-O-alkyl-D-mannitol (1 equiv., SM) in THF-$H_2O$ (9:1) was added $NaIO_4$ (1.2 equiv.) at room temperature and the mixture was stirred at 50° C. for 1 h. The resulting inorganic salt was removed by filtration through a pad of silica gel and washed with EtOAc. The filtrate was concentrated in vacuo and the crude aldehyde was used for the next reaction.

To a stirred solution of the residue in t-BuOH (20 mL/mmol-SM) were added 2-methyl-2-butene (100 equiv.) and a solution of 80% $NaClO_2$ (12 equiv.) and $NaH_2PO_4 \cdot H_2O$ (10 equiv.) in $H_2O$ (8 mL/mmol-SM) at 0° C. successively. The resulting yellow mixture was allowed to warm to room temperature for 6 h, during which it turned into clear. Then, the mixture was cooled to 0° C. again and treated with 2.5 M aq. $Na_2SO_3$ (25 equiv.) to reduce an excess of $NaClO_2$. The mixture was acidified with 10% aq. citric acid (10 mL/mmol-SM) and extracted twice with $CHCl_3$ and the combined organic phases were washed with brine, dried over $MgSO_4$, and then concentrated in vacuo. The crude acid was used for the next reaction without further purification.

To a stirred solution of the residue in anhydrous THF-MeOH (1:1, 10 mL/mmol-SM) was treated with 2 M $TMSCHN_2$ solution in hexanes (3.2 equiv.) at 0° C. After being stirred for 10 min, the resulting yellow mixture was decolorized by an addition of AcOH (3.2 equiv.) to consume an excess of $TMSCHN_2$. The mixture was concentrated in vacuo and the residue was purified by silica gel chromatography (petroleum ether:EtOAc=4:1 to 3:2) to give methyl 2-O-alkyl-D-glycerate.

Preparation of Methyl 2-O-Fluoroalkyl-D-Glycerate

To a stirred 0.9 M solution of methyl 2-O-(9-decenyl)-D-glycerate (1 equiv., SM), prepared from 1,3:4,6-di-O,O-(4-methoxybenzylidene)-D-mannitol and 9-decenyl p-toluenesulfonate in the above-mentioned 5 steps, in hexane were added perfluorooctyl iodide (1.2 equiv.) and 1 M $Et_3B$ solution in hexanes (0.2 equiv.) at room temperature under air. The reaction mixture was stirred at the same temperature for 1.5 h, then perfluorooctyl iodide (0.3 equiv.) and 1 M $Et_3B$ solution in hexanes (0.1 equiv.) were added again. After being stirred for 30 min, the solution was diluted with $Et_2O$ and poured into a mixture of sat. aq. $NaHCO_3$ and 10% aq. $Na_2S_2O_3 \cdot 5H_2O$. The mixture was extracted twice with $Et_2O$ and the combined organic phases were washed with brine, dried over $MgSO_4$, and then concentrated in vacuo. The crude iodide was used for the next reaction without further purification.

To a solution of the residue in MeOH (10 mL/mmol-SM) were added $NaHCO_3$ (1.5 equiv.) and 10% PdC (mg/mg-SM). The resulting mixture was stirred at room temperature for 13 h under $H_2$ atmosphere (1 atm). PdC was removed by filtration through a pad of Celite and washed with EtOAc. The filtrate was concentrated in vacuo and the residue was purified by silica gel chromatography (petroleum ether:EtOAc=3:1 to 7:3) to give methyl 2-O-fluoroalkyl-D-glycerate.

Preparation of 0.2 M Phosphoramidite Solution

To a 0.2 M solution of methyl 2-O-alkyl-D-glycerate (1 equiv.) in anhydrous $CH_3CN$ were added N,N-diisopropylethylamine (1.5 equiv.) and ClP(OCE)Ni—$Pr_2$ (1.2 equiv.) at room temperature successively. The reaction mixture was stirred for 1 h and directly used for the next coupling reaction.

Preparation of Nonaacetyl Moenomycin A Pentasaccharide Phosphate

To a mixture of nonaacetyl moenomycin A pentasaccharide lactol (1 equiv., SM), azeotropically dried from toluene, and flame-dried MS-3A (2.8 g/mmol-SM) was added 0.34 M 1H-tetrazole solution in CH$_3$CN (6 equiv.) at room temperature. After being stirred for 15 min to remove a trace amount of water, the suspension was cooled to 0° C. and treated with 0.2 M phosphoramidite solution in CH$_3$CN (2 equiv.). The reaction mixture was allowed to warm to room temperature for 1 h, cooled to 0° C. again, and then treated with 5.5 M t-BuO$_2$H solution in decane (12 equiv.) to oxidize the resulting phosphite intermediate into the corresponding phosphate. After being stirred below 10° C. for 1 h, the mixture was treated with P(OMe)$_3$ (12 equiv.) to reduce an excess of t-BuO$_2$H. Then, MS-3A was removed by filtration through a pad of Celite and washed with MeOH. The filtrate was concentrated in vacuo and the residue was roughly purified by silica gel chromatography (EtOAc:MeOH containing 0.5% AcOH=7:1 to 4:1) to give nonaacetyl moenomycin A pentasaccharide phosphate.

Moenomycin A Lipid Analogues, Ammonium Salt

To a stirred 6 mM solution of nonaacetyl moenomycin A pentasaccharide phosphate (1 equiv.) in THF-MeOH—H$_2$O (3:1:1) was added 1 M aq. LiOH.H$_2$O (12 equiv.) at 0° C. The reaction mixture was allowed to warm to room temperature for 2.5 h, and then neutralized with DOWEX 50WX2-100 (NH$_4^+$ form, 120 equiv.). The resin was removed by filtration with sintered glass funnel and washed with MeOH. The filtrate was concentrated in vacuo and the residue was purified by reversed-phase HPLC (Agilent Technologies 1200 series HPLC instrument (flow-rate: 1.5 mL/min using a Phenomenex Luna 5 mm C18 column (250×10.0 mm)) to give moenomycin A lipid analogues as a white solid.

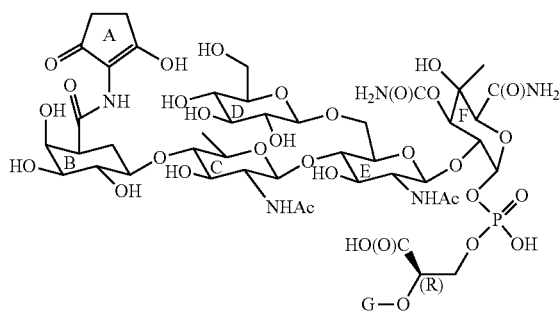

MHz, CD$_3$OD): δ 5.95 (m, 1H), 5.40 (t, J=6.4 Hz, 1H), 5.12-5.08 (m, 4H), 4.55-4.40 (m, 5H), 4.30-4.11 (m, 8H), 3.92-3.90 (m, 2H), 3.77-3.43 (m, 14H), 3.36-3.22 (m, 2H), 2.54 (s, 4H), 2.10-1.94 (m, 18H), 1.77 (s, 3H), 1.66 (s, 3H), 1.61 (s, 3H), 1.59 (2s, 6H), 1.43 (d, J=5.9 Hz, 3H), 1.24 (s, 3H). $^{13}$C NMR (125 MHz, D$_2$O): δ 199.8, 174.7, 174.3, 172.7, 169.9, 158.3, 142.4, 135.8, 135.0, 131.3, 124.6, 124.5, 124.0, 120.7, 110.6, 103.3, 103.1, 102.4, 101.4, 94.6, 83.0, 79.5, 77.7, 76.4, 76.3, 76.0, 74.9, 73.7, 73.2, 73.1, 72.6, 72.4, 72.2, 71.4, 70.7, 69.9, 69.2, 68.6, 66.7, 61.0, 55.9, 55.2, 39.7, 32.0, 30.3, 29.8, 26.7, 26.6, 25.6, 23.4, 22.7, 17.5, 17.0, 15.9, 15.8, 15.2. $^{31}$P NMR (162 MHz, CD$_3$OD): δ −1.52. HRMS (ESI) calcd for C$_{64}$H$_{99}$N$_5$O$_{34}$P [M−NH$_4$]$^+$ 1512.5915, found 1512.5899.

Compound (1c)

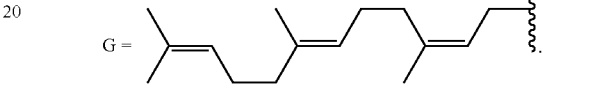

N$_1$-[(2-Hydroxy-5-oxo-cyclopenten-1-yl)-(5S)-β-D-galactopyranuronamide]-(1→4)-2-acetamide-2,6-dideoxy-β-D-gluopyranosyl-(1→4)-[β-D-glucopyranosyl-(1→6)]-2-acetamido-2-deoxy-β-D-glucopyranosyl)-(1→2)-3-O-carbamoyl-1-O—{[(R)-2-carboxy-2-((2Z,6E)-3,7,11-trimethyl-dodeca-2,6,10-trien-1-yloxy)ethoxy]hydroxyphosphoryl}-4-C-methyl-α-D-glucopyranuronamide, Ammonium salt (1c). Retention time: 28.6 min (1.5 mL/min, gradient 0-45% CH$_3$CN/0.1 wt % aq. NH$_4$HCO$_3$ over 30 min) $^1$H NMR (400 MHz, D$_2$O): δ 5.79 (m, 1H), 5.42 (m, 1H), 5.16 (m, 2H), 5.03 (d, J=10.2 Hz, 1H), 4.65-4.44 (m, 5H), 4.32-4.11 (m, 8H), 3.95-3.48 (m, 16H), 3.43-3.29 (m, 2H), 2.45 (s, 4H), 2.15-2.02 (m, 14H), 1.78 (s, 3H), 1.69 (s, 3H), 1.62 (2s, 6H), 1.41 (d, J=5.5 Hz, 3H), 1.23 (s, 3H). $^{13}$C NMR (125 MHz, D$_2$O): δ 199.8, 175.4, 174.7, 174.4, 172.9, 169.9, 158.3, 143.6, 137.0, 133.5, 124.6, 124.1, 120.3, 110.6, 103.3, 103.0, 102.4, 101.4, 94.6, 83.3, 79.9, 78.1, 76.6, 76.2, 76.0, 75.1, 74.9, 73.7, 73.31, 73.26, 73.0, 72.6, 72.4, 72.2, 71.4, 70.8, 69.9, 69.1, 68.8, 66.7, 66.5, 60.9, 55.9, 55.2, 39.0, 31.5, 30.2, 26.1, 26.0, 25.1, 23.0, 22.6, 22.5, 17.3, 16.9, 15.5, 14.9. $^{31}$P NMR (162 MHz, D$_2$O): δ −1.08. HRMS (ESI) calcd for C$_{59}$H$_{91}$N$_5$O$_{34}$P [M−NH$_4$]$^+$ 1444.5289, found 1444.5257.

Compound (1b)

G = <span>/\\/\\/\\/\\/\\/\\</span>

N$_1$-[(2-Hydroxy-5-oxo-cyclopenten-1-yl)-(5S)-β-D-galactopyranuronamide]-(1→4)-2-acetamide-2,6-dideoxy-β-D-gluopyranosyl-(1→4)-[β-D-glucopyranosyl-(1→6)]-2-acetamido-2-deoxy-β-D-glucopyranosyl)-(1→2)-3-O-carbamoyl-1-O—{[(R)-2-carboxy-2-((2Z,6E,10E)-3,7,11,15-tetramethyl-hexadeca-2,6,10,14-tetraen-1-yloxy)ethoxy]hydroxyphosphoryl}-4-C-methyl-α-D-glucopyranuronamide, Ammonium salt (1b)

Retention time: 28.9 min (1.5 mL/min, gradient 0-60% CH$_3$CN/0.1 wt % aq. NH$_4$HCO$_3$ over 30 min). $^1$H NMR (400

Compound (1d)

G = <span>\\/\\/\\/\\/\\/\\/\\/\\/\\</span>

N$_1$-[(2-Hydroxy-5-oxo-cyclopenten-1-yl)-(5S)-β-D-galactopyranuronamide]-(1→4)-2-acetamide-2,6-dideoxy-β-D-gluopyranosyl-(1→4)-[β-D-glucopyranosyl-(1→6)]-2-acetamido-2-deoxy-β-D-glucopyranosyl)-(1→2)-3-O-carbamoyl-1-O—{[(R)-2-carboxy-2-(eicosan-1-yloxy)ethoxy]hydroxyphosphoryl}-4-C-methyl-α-D-glucopyranuronamide, Ammonium salt (1d). Retention time: 27.8 min (1.5 mL/min, gradient 0-80% CH$_3$CN/0.1 wt % aq. NH$_4$HCO$_3$ over 30 min). $^1$H NMR (400 MHz, CD$_3$OD): δ 5.95 (m, 1H), 5.10 (d, J=10.2 Hz, 1H), 4.55-4.04 (m, 13H), 3.93-3.90 (m, 2H), 3.75-3.24 (m, 16H), 2.54 (s, 4H), 2.05 (s, 3H), 2.03 (s, 3H), 1.64-1.62 (m, 2H), 1.43 (d, J=6.2 Hz, 3H), 1.41-1.28 (m, 34H), 1.24 (s, 3H), 0.89 (t, J=6.8 Hz, 3H). $^{13}$C NMR (125 MHz, D$_2$O): δ 199.6, 174.6, 174.4, 172.6, 169.8, 158.3, 110.7, 103.2, 103.1, 102.5, 101.4, 94.7, 82.9, 79.5, 79.1, 76.3, 76.1, 75.0, 73.6, 73.2, 72.4, 72.3, 71.3, 70.7, 69.9, 69.2, 68.5, 66.5, 61.0, 55.9, 55.2, 32.2, 30.1, 30.0, 29.7, 29.3, 26.0, 22.9, 22.7, 17.1, 15.3, 14.2. $^{31}$P NMR (162 MHz, CD$_3$OD): δ −1.30. HRMS (ESI) calcd for C$_{64}$H$_{107}$N$_5$O$_{34}$P [M−NH$_4$]$^+$ 1520.6541, found 1520.5525.

Compound (1e)

N$_1$-[(2-Hydroxy-5-oxo-cyclopenten-1-yl)-(5S)-β-D-galactopyranuronamide]-(1→4)-2-acetamide-2,6-dideoxy-β-D-gluopyranosyl-(1→4)-[β-D-glucopyranosyl-(1→6)]-2-acetamido-2-deoxy-β-D-glucopyranosyl)-(1→2)-3-O-carbamoyl-1-O—{[(R)-2-carboxy-2-(octadecan-1-yloxy)ethoxy]hydroxyphosphoryl}-4-C-methyl-α-D-glucopyranuronamide, Ammonium salt (1e). Retention time: 28.8 min (1.5 mL/min, gradient 0-70% CH$_3$CN/0.1 wt % aq. NH$_4$HCO$_3$ over 30 min). $^1$H NMR (400 MHz, CD$_3$OD): δ 5.99 (m, 1H), 5.09 (d, J=10.2 Hz, 1H), 4.55-4.12 (m, 13H), 3.92-3.89 (m, 2H), 3.80-3.23 (m, 16H), 2.54 (s, 4H), 2.05 (s, 3H), 2.00 (s, 3H), 1.65-1.60 (m, 2H), 1.43 (d, J=5.9 Hz, 3H), 1.38-1.28 (m, 30H), 1.24 (s, 3H), 0.89 (t, J=6.8 Hz, 3H). $^{13}$C NMR (125 MHz, D$_2$O): δ 200.0, 174.9, 174.7, 174.4, 172.6, 169.8, 158.3, 110.5, 103.2, 103.1, 102.5, 101.4, 94.7, 83.1, 79.4, 79.2, 76.3, 76.1, 74.9, 73.7, 73.2, 72.4, 72.2, 71.4, 71.2, 70.7, 69.9, 69.2, 68.5, 66.5, 61.0, 55.9, 55.1, 32.2, 30.4, 30.1, 30.0, 29.7, 29.3, 25.9, 22.9, 22.7, 17.0, 15.2, 14.2. $^{31}$P NMR (162 MHz, CD$_3$OD): δ −1.45. HRMS (ESI) calcd for C$_{62}$H$_{103}$N$_5$O$_{34}$P [M−NH$_4$]$^+$ 1492.6228, found 1492.5222.

Compound (1f)

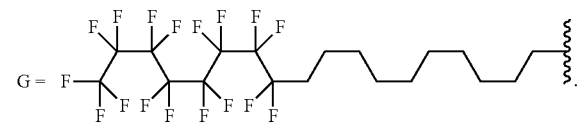

N$_1$-[(2-Hydroxy-5-oxo-cyclopenten-1-yl)-(5S)-β-D-galactopyranuronamide]-(1→4)-2-acetamide-2,6-dideoxy-β-D-gluopyranosyl-(1→4)-[β-D-glucopyranosyl-(1→6)]-2-acetamido-2-deoxy-β-D-glucopyranosyl)-(1→2)-3-O-carbamoyl-1-O—{[(R)-2-carboxy-2-(11,11,12,12,13,13,14,14,15,15,16,16,17,17,18,18,18-heptadecafluoro-octadecan-1-yloxy)ethoxy]hydroxyphosphoryl}-4-C-methyl-α-D-glucopyranuronamide, Ammonium salt (1f). Retention time: 32.3 min (1.5 mL/min, gradient 0-70% CH$_3$CN/0.1 wt % aq. NH$_4$HCO$_3$ over 35 min) $^1$H NMR (400 MHz, CD$_3$OD): δ 5.87 (dd, J=6.0, 3.5 Hz, 1H), 5.06 (d, J=10.6 Hz, 1H), 4.56-4.45 (m, 5H), 4.28-4.06 (m, 8H), 3.92-3.90 (m, 2H), 3.77-3.22 (m, 16H), 2.39 (s, 4H), 2.19-2.05 (m, 2H), 2.03 (s, 3H), 2.01 (s, 3H), 1.66-1.55 (m, 4H), 1.42 (d, J=5.9 Hz, 3H), 1.32-1.28 (m, 12H), 1.24 (s, 3H). $^{19}$F NMR (376 MHz, D$_2$O): δ −83.2 (3F), −115.8 (2F), −123.2 (2F), −123.5 (4F), −124.4 (2F), −124.9 (2F), −128.1 (2F). $^{31}$P NMR (162 MHz, CD$_3$OD): δ −1.06. HRMS (ESI) calcd for C$_{62}$H$_{86}$F$_{17}$N$_5$O$_{34}$P [M−NH$_4$]$^+$ 1798.4626, found 1798.4622.

Compound (1g)

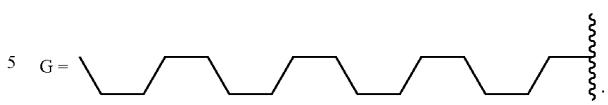

N$_1$-[(2-Hydroxy-5-oxo-cyclopenten-1-yl)-(5S)-β-D-galactopyranuronamide]-(1→4)-2-acetamide-2,6-dideoxy-β-D-gluopyranosyl-(1→4)-[β-D-glucopyranosyl-(1→6)]-2-acetamido-2-deoxy-β-D-glucopyranosyl)-(1→2)-3-O-carbamoyl-1-O—{[(R)-2-carboxy-2-(hexadecan-1-yloxy)ethoxy]hydroxyphosphoryl}-4-C-methyl-α-D-glucopyranuronamide, Ammonium salt (1 g). Retention time: 30.2 min (1.5 mL/min, gradient 0-60% CH$_3$CN/0.1 wt % aq. NH$_4$HCO$_3$ over 30 min). $^1$H NMR (400 MHz, CD$_3$OD): δ 5.97 (m, 1H), 5.09 (d, J=10.6 Hz, 1H), 4.53-4.12 (m, 13H), 3.92-3.89 (m, 2H), 3.77-3.24 (m, 16H), 2.54 (s, 4H), 2.05 (s, 3H), 2.00 (s, 3H), 1.63-1.62 (m, 2H), 1.43 (d, J=6.2 Hz, 3H), 1.40-1.28 (m, 26H), 1.24 (s, 3H), 0.89 (t, J=6.8 Hz, 3H). $^{13}$C NMR (125 MHz, D$_2$O): δ 199.7, 175.0, 174.6, 174.4, 172.6, 169.8, 158.3, 110.6, 103.2, 103.1, 102.5, 101.4, 94.7, 83.0, 79.5, 79.3, 76.4, 76.3, 76.1, 75.0, 73.7, 73.2, 73.1, 72.5, 72.4, 72.2, 71.4, 71.2, 70.7, 69.8, 69.2, 68.5, 66.5, 60.9, 55.9, 55.2, 32.1, 30.3, 30.0, 29.9, 29.6, 29.2, 25.9, 22.8, 22.7, 17.0, 15.2, 14.2. $^{31}$P NMR (162 MHz, CD$_3$OD): δ −1.54. HRMS (ESI) calcd for C$_{60}$H$_{99}$N$_5$O$_{34}$P [M−NH$_4$]$^+$ 1464.5915, found 1464.5903.

Compound (1h)

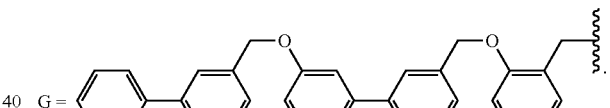

N$_1$-[(2-Hydroxy-5-oxo-cyclopenten-1-yl)-(5S)-β-D-galactopyranuronamide]-(1→4)-2-acetamide-2,6-dideoxy-β-D-gluopyranosyl-(1→4)-[β-D-glucopyranosyl-(1→6)]-2-acetamido-2-deoxy-β-D-glucopyranosyl)-(1→2)-3-O-carbamoyl-1-O—{[(R)-2-carboxy-2-(3-((3'-([1,1'-biphenyl]-3-ylmethoxy)-[1,1'-biphenyl]-3-yl)methoxy)phenylmethan-1-yloxy)ethoxy]hydroxyphosphoryl}-4-C-methyl-α-D-glucopyranuronamide, Ammonium salt (1h). Retention time: 33.3 min (1.5 mL/min, gradient 0-60% CH$_3$CN/0.1 wt % aq. NH$_4$HCO$_3$ over 35 min) $^1$H NMR (400 MHz, D$_2$O): δ 7.31-6.29 (m, 21H), 5.79 (m, 1H), 5.04 (m, 1H), 4.80-3.32 (m, 35H), 2.36 (s, 4H), 2.07 (s, 3H), 2.05 (s, 3H), 1.39 (m, 3H), 1.23 (s, 3H). $^{13}$C NMR (125 MHz, D$_2$O): δ 200.2, 174.6, 174.4, 172.5, 169.8, 158.7, 158.3, 156.0, 141.7, 140.6, 140.2, 139.9, 137.5, 137.3, 130.1129.4, 128.7, 126.6, 125.8, 121.4, 119.6, 113.7, 113.3, 113.0, 112.3, 110.4, 103.2, 103.0, 102.4, 101.4, 94.5, 83.1, 79.4, 78.7, 76.2, 76.0, 74.9, 73.6, 73.2, 72.3, 72.2, 71.3, 70.7, 69.8, 69.1, 68.5, 66.7, 60.9, 55.8, 55.1, 30.4, 22.7, 17.0, 15.2. $^{31}$P NMR (162 MHz, D$_2$O): δ −1.07. HRMS (ESI) calcd for C$_{77}$H$_{93}$N$_5$O$_{36}$P [M−NH$_4$]$^+$ 1694.5343. found 1694.5324.

Compound (1i)

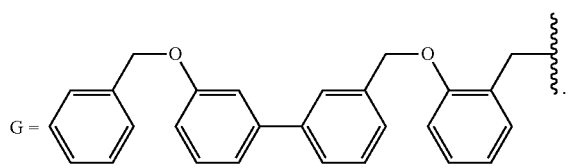

N₁-[(2-Hydroxy-5-oxo-cyclopenten-1-yl)-(5S)-β-D-galactopyranuronamide]-(1→4)-2-acetamide-2,6-dideoxy-β-D-gluopyranosyl-(1→4)-[β-D-glucopyranosyl-(1→6)]-2-acetamido-2-deoxy-β-D-glucopyranosyl)-(1→2)-3-O-carbamoyl-1-O—{[(R)-2-carboxy-2-(3-((3'-(benzyloxy)-[1,1'-biphenyl]-3-yl)methoxy)phenylmethan-1-yloxy)ethoxy]hydroxyphosphoryl}-4-C-methyl-α-D-glucopyranuronamide, Ammonium salt (1i). Retention time: 27.8 min (1.5 mL/min, gradient 0-60% $CH_3CN$/0.1 wt % aq. $NH_4HCO_3$ over 30 min) $^1$H NMR (400 MHz, $CD_3OD$): δ 7.62-7.19 (m, 14H), 7.02-6.96 (m, 3H), 5.90 (dd, J=6.2, 3.3 Hz, 1H), 5.17 (s, 2H), 5.14 (s, 2H), 5.07 (d, J=10.6 Hz, 1H), 4.87-4.09 (m, 13H), 3.91-3.88 (m, 2H), 3.73-3.21 (m, 16H), 2.35 (s, 4H), 2.01 (s, 3H), 1.99 (s, 3H), 1.36 (d, J=6.2 Hz, 3H), 1.24 (s, 3H). $^{13}$C NMR (125 MHz, $D_2O$): δ 200.5, 175.0, 174.6, 174.4, 172.5, 169.9, 158.7, 158.3, 156.1, 141.7, 140.3, 137.6, 136.6, 130.2, 129.4, 128.5, 127.9, 127.4, 126.6, 126.4, 125.9, 125.5, 121.4, 119.7, 113.6, 112.5, 110.3, 103.2, 103.1, 102.4, 101.4, 94.5, 83.2, 79.5, 78.9, 76.4, 76.2, 76.0, 75.0, 74.9, 73.7, 73.2, 73.1, 72.5, 72.4, 72.2, 71.3, 70.8, 69.8, 69.6, 69.1, 68.5, 67.1, 66.8, 60.9, 55.8, 55.2, 30.4, 30.2, 16.9, 15.1. $^{31}$P NMR (162 MHz, $CD_3OD$): δ −0.98. HRMS (ESI) calcd for $C_{71}H_{89}N_5O_{36}P$ [M−$NH_4$]$^+$ 1618.5030, found 1618.5003.

Compound (1j)

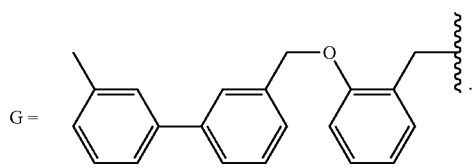

N₁-[(2-Hydroxy-5-oxo-cyclopenten-1-yl)-(5S)-β-D-galactopyranuronamide]-(1→4)-2-acetamide-2,6-dideoxy-β-D-gluopyranosyl-(1→4)-[β-D-glucopyranosyl-(1→6)]-2-acetamido-2-deoxy-β-D-glucopyranosyl)-(1→2)-3-O-carbamoyl-1-O—{[(R)-2-carboxy-2-(3-((3'-methyl-[1,1'-biphenyl]-3-yl)methoxy)phenylmethan-1-yloxy)ethoxy]hydroxyphosphoryl}-4-C-methyl-α-D-glucopyranuronamide, Ammonium salt (1j). Retention time: 28.1 min (1.5 mL/min, gradient 0-50% $CH_3CN$/0.1 wt % aq. $NH_4HCO_3$ over 30 min)

Example 1

A 96 well plate with 100 µL test medium in all wells was prepared by handheld multipipettor. A stock solution of the antibiotic or compound in DMSO (0.05~10 mg/mL, 5 µL) and the same medium (95 µL) were put together into column one, where the compound concentration doubled the highest one to be tested. Two columns were necessary for each compound to check the reproducibility. The compound was diluted by adding 100 µL from column one to column two with a 50% volume mix done three times; diluting serially across the plate was continued.

The day before the assay was scheduled to be run, strains were suspended in the test media (Brain Heart Infusion (BHI) containing 0.1% casaminoacids for S. aureus, S. epidermidis, and E. faecalis, Trypticase Soy Broth (TSB) containing 5% sheep blood for S. pneumoniae, and Lysogeny Broth (LB) for E. coli) and incubated overnight at 35-37° C. The suspension was diluted with the same media to 1%, 100 µL of which was added to each well of the MIC plate. The MIC plate was incubated at 35-37° C. for 20 h. A thiazolyl blue tetrazolium bromide (MTT) solution (1 mg/mL-water, 50 µL) was added into each well and the resulting MIC plate was incubated at 35-37° C. for a few hours to stain wells in which cell proliferated. Growth is also visible as any turbidity in wells. MIC was defined as the lowest antibiotic concentration that resulted in no growth after the incubation. See Table 1.

Example 2

Curtailing the tail portion of Moenomycin A (MmA) led to shorter half-life. Following IV (2 mpk) and SC (10 mpk) administration, significant systemic exposure to CB-186295 (Moenomycin A) was observed. The compound exhibited biphasic kinetics with distribution phase followed by elimination phase. The % SC bioavailability was 89%. The half-life following IV and SC administration were 8.7 and 7.5 days, respectively (NCA analysis). The clearance following IV administration was very low leading higher exposure (3 mL/hr/kg) and volume of distribution (Vss) was 0.5 L/kg. See Table 2.

TABLE 1

| | S. aureus 13709 25923 13709 | S. epidermidis 1228 700562 | E. faecalis 29212 33186 | S. pneumoniae 6303 #1629 | E. coli MG1655 NR698 |
|---|---|---|---|---|---|
| Vancomycin•HCl | 3.9 3.9 2.0 | 2.0 3.9 | 3.9 2.0 | 0.49 0.49 | 250 0.49 |
| 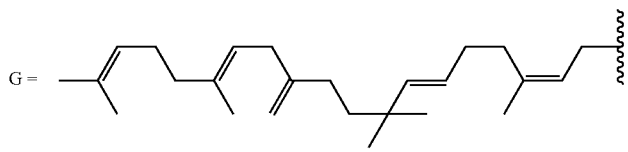<br>moenocinol (1a) | 0.16 0.16 0.078 | 0.16 0.16 | 0.16 0.16 | 1.3 1.3 | 31 0.0098 |

TABLE 1-continued
| | S. aureus 13709 25923 13709 | S. epidermidis 1228 700562 | E. faecalis 29212 33186 | S. pneumoniae 6303 #1629 | E. coli MG1655 NR698 |
|---|---|---|---|---|---|
| 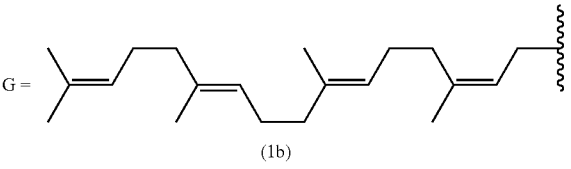 [SMILES: *C/C=C(/C)CC/C=C(\C)CC/C=C(\C)CCC=C(C)C] G = (1b) | 3.9 3.9 2.0 | 2.0 2.0 | 3.9 3.9 | 2.0 3.9 | 63 0.061 |
| 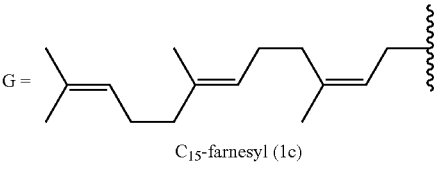 G = $C_{15}$-farnesyl (1c) | >250 >250 250 | >250 >250 | 250 >250 | 63 31 | >250 0.98 |
| 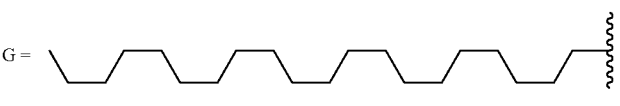 G = (1d) | 1.3 0.63 0.63 | 0.63 1.3 | 0.63 0.63 | 2.0 3.1 | 7.8 0.0049 |
| 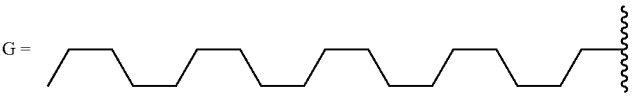 G = (1e) | 2.0 0.98 0.98 | 0.49 0.49 | 0.49 0.98 | 3.9 3.9 | 63 0.0024 |
| 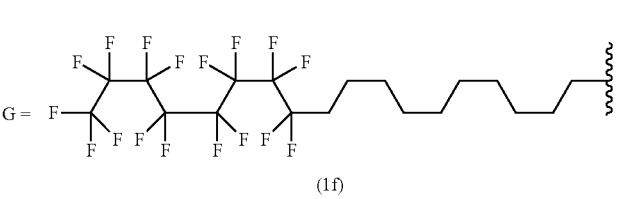 G = (1f) | 3.9 2.0 2.0 | 0.98 2.0 | 0.98 2.0 | 2.0 0.98 | 250 >0.16 |
| 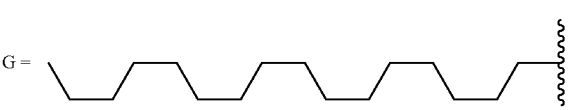 G = n-$C_{16}$-alkyl (1g) | 16 16 16 | 16 31 | 31 16 | 16 16 | 250 0.16 |
| 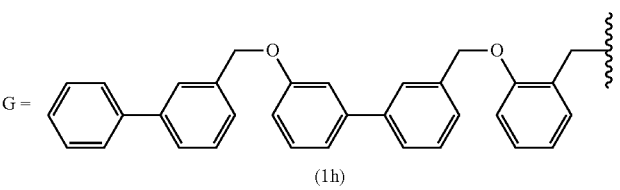 [SMILES: *Cc1ccccc1OCc1cccc(-c2cccc(OCc3cccc(-c4ccccc4)c3)c2)c1] G = (1h) | 0.39 0.20 0.20 | 0.20 0.20 | 0.39 0.78 | 0.98 2.0 | 125 0.039 |

TABLE 1-continued
| | S. aureus 13709 25923 13709 | S. epidermidis 1228 700562 | E. faecalis 29212 33186 | S. pneumoniae 6303 #1629 | E. coli MG1655 NR698 |
|---|---|---|---|---|---|
| G = 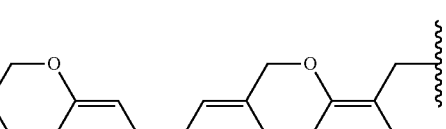 (1i) | 7.8 7.8 7.8 | 3.9 7.8 | 16 32 | 3.9 7.8 | >250 0.49 |
| G = 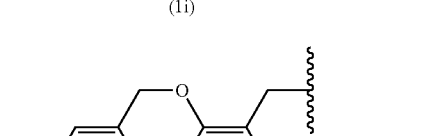 (1j) | >250 >250 >250 | 125 >250 | >250 >250 | 16 16 | >250 0.98 |
TABLE 2
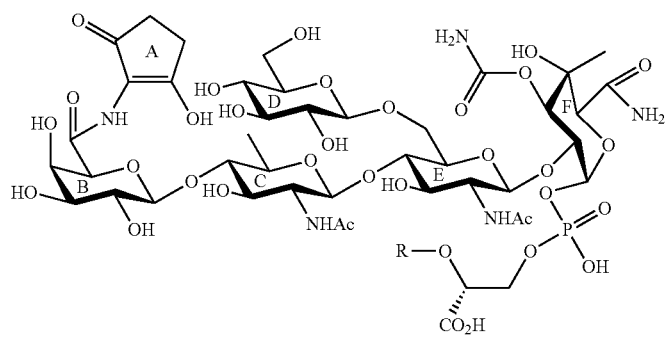
| R = | cmpd | Dose (mg/kg) | $AUC_{last}$ (ug*hr/mL) | $AUC_{inf}$ (ug*hr/mL) | $DN\_AUC_{inf}$ (ug*hr/mL)/(mg/kg) | $C_0$ (ug/mL) | $C_{max}$ (ug/mL) | $T_{max}$ (hr) | Half-life (hr) |
|---|---|---|---|---|---|---|---|---|---|
| (farnesyl-like chain) | 1a MmA | 1.44 | 366.79 | 491.94 | 341.62 | 24.70 | 19.13 | 1.00 | 32.33 |
| (polyprenyl chain) | 1b | 1.7 | 234 | 241 | 141 | 10.2 | 8.64 | 1 | 47 |
| (polyprenyl chain) | 1c | 1.16 | 28 | 35 | 27 | 9.5 | 6.67 | 1 | 2.5 |
| (alkyl chain) | 1d | 2* | 16.8 | 28.2** | 14.1** | 0.8 | 0.717 | 1 | 42.3** |

TABLE 2-continued
| R = | cmpd | | | | | | | |
|---|---|---|---|---|---|---|---|---|
| 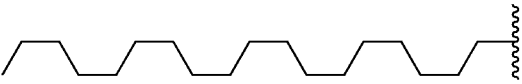 | 1e | 2* | 35.1 | 41.7 | 20.8 | 1.49 | 1.4 | 1 | 21.1 |
| 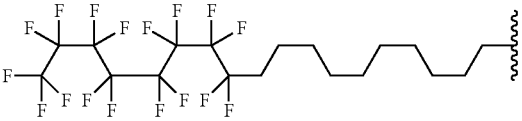 | 1f | 1.56 | 109.71 | 135.41 | 86.80 | 8.52 | 6.04 | 1.00 | 26.16 |
| 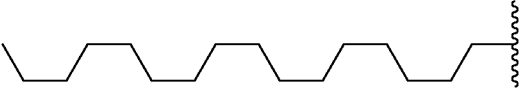 | 1g | 2* | 58.4 | 79.7 | 39.8 | 1.71 | 1.7 | 1 | 38.3 |
| 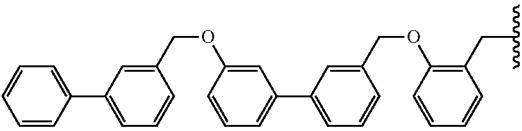 | 1h | 1.78 | 255.21 | 265.07 | 148.92 | 15.34 | 12.05 | 1.00 | 15.26 |
| 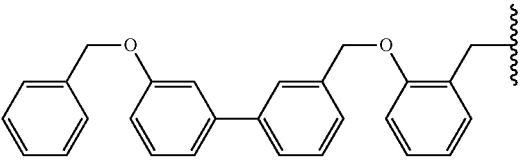 | 1i | 1.3 | 190.09 | 312.48 | 240.37 | 14.15 | 13.77 | 1.00 | 16.13 |
| R = | cmpd | MRT (hr) | Clearance (mL/min/kg) | $V_z$ (L/kg) | $V_{ss}$ (L/kg) | MIC Sa42 ug/ml | MIC Sa399 ug/ml |
|---|---|---|---|---|---|---|---|
| 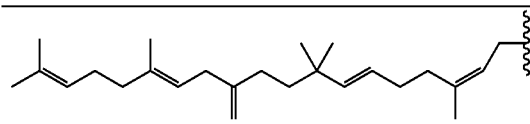 | 1a MmA | 42.94 | 0.05 | 0.14 | 0.13 | 0.25 | 0.25 |
| 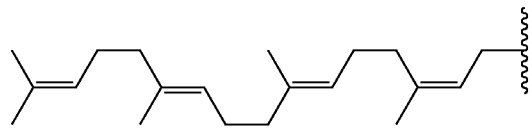 | 1b | | 0.12 | 0.48 | 0.34 | 2.5-3.1 | 5-6.3 |
| 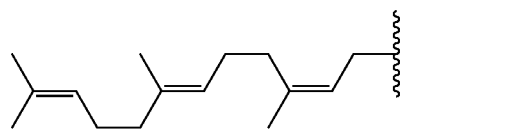 | 1c | | 0.61 | 0.14 | 0.12 | >50 | >50 |
| 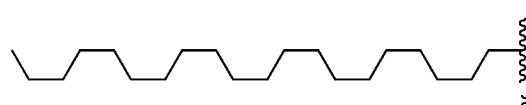 | 1d | 71.5 | 1.18 | 4.33 | 5.07 | 6.3 | 12.5 |
| 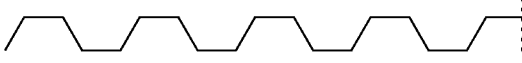 | 1e | 34.9 | 0.8 | 1.46 | 1.67 | >10 | 12.5 |
| 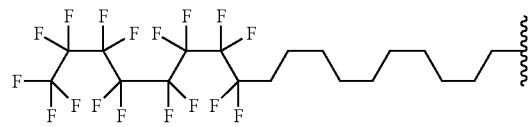 | 1f | 38.58 | 0.19 | 0.43 | 0.44 | 4 | 8 |
| 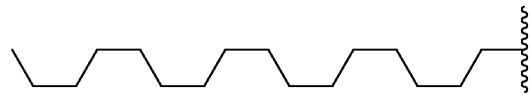 | 1g | 53 | 0.418 | 1.39 | 1.33 | ND | >10 |

TABLE 2-continued

| Structure | ID | | | | | | |
|---|---|---|---|---|---|---|---|
| (structure) | 1h | 21.67 | 0.11 | 0.15 | 0.15 | 4 | 8 |
| (structure) | 1i | 24.24 | 0.07 | 0.10 | 0.10 | 2 | 4 |

*dose solution not analyzed to determine exact dose
**R2 > 0.9 for elimination rate constant

EQUIVALENTS AND SCOPE

Those skilled in the art will recognize or be able to ascertain using no more than routine experimentation many equivalents to the specific embodiments described herein. The scope of the present embodiments described herein is not intended to be limited to the above Description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim.

Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps.

Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control.

In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

The foregoing has been a description of certain non-limiting embodiments of the invention. Those of ordinary skill in the art will appreciate that various changes and modifications to this description may be made without departing from the spirit or scope of the present invention, as defined in the following claims.

What is claimed is:

1. A compound of Formula (I):

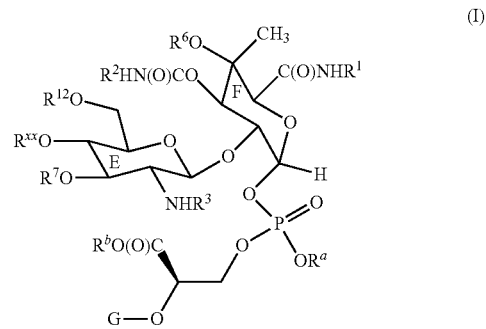

or a pharmaceutically acceptable salt, solvate, hydrate, tautomer, isomer, enantiomer, diastereomer, or polymorph thereof;

wherein:

G is a group of Formula (a), (b), or (c):

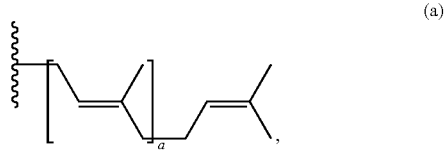

wherein a is 3, 4, or 5;

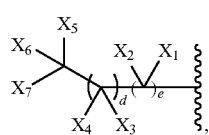
(b)

wherein:
$X_1$, $X_2$, $X_3$, $X_4$, $X_5$, $X_6$, and $X_7$ are each independently hydrogen or halogen;
d is an integer between 1 and 25, inclusive; and
e is an integer of between 2 and 25, inclusive;
provided that at least one of $X_1$, $X_2$, $X_3$, $X_4$, $X_5$, $X_6$, and $X_7$ is halogen; and
the sum of d and e is greater than 16;
or

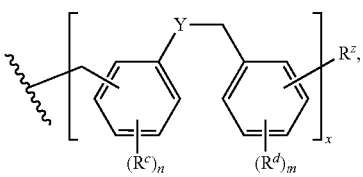
(c)

wherein:
Y is —O—, —S—, —$NR^Y$—, or an optionally substituted methylene group, wherein $R^Y$ is hydrogen, optionally substituted aliphatic, or an amino protecting group;
each instance of $R^c$ is independently —F, —Br, —I, —Cl, optionally substituted aliphatic, optionally substituted heteroaliphatic, optionally substituted carbocycyl, optionally substituted heterocycyl, optionally substituted aryl, optionally substituted heteroaryl, —$OR^e$, —$SR^e$, —$NHR^e$, or —$N(R^e)_2$, wherein each instance of $R^e$ is independently hydrogen, optionally substituted aliphatic, optionally substituted heteroaliphatic, optionally substituted carbocycyl, optionally substituted heterocycyl, optionally substituted aryl, or optionally substituted heteroaryl, or two $R^e$ groups are joined to form a 5- to 6-membered optionally substituted heterocycyl or optionally substituted heteroaryl ring;
each instance of $R^d$ is independently —F, —Br, —I, —Cl, optionally substituted aliphatic, optionally substituted heteroaliphatic, optionally substituted carbocycyl, optionally substituted heterocycyl, optionally substituted aryl, optionally substituted heteroaryl, —$OR^f$, —$SR^f$, —$NHR^f$, or —$N(R^f)_2$, wherein each instance of $R^f$ is independently hydrogen, optionally substituted aliphatic, optionally substituted heteroaliphatic, optionally substituted carbocycyl, optionally substituted heterocycyl, optionally substituted aryl, or optionally substituted heteroaryl, or two $R^f$ groups are joined to form a 5- to 6-membered optionally substituted heterocycyl or optionally substituted heteroaryl ring;
$R^z$ is hydrogen, —F, —Br, —I, —Cl, optionally substituted aliphatic, optionally substituted heteroaliphatic, optionally substituted carbocycyl, optionally substituted heterocycyl, optionally substituted aryl, optionally substituted heteroaryl, —$OR^g$, —$SR^g$, —$NHR^g$, or —$N(R^g)_2$, wherein each instance of $R^g$ is independently hydrogen, optionally substituted aliphatic, optionally substituted heteroaliphatic, optionally substituted carbocycyl, optionally substituted heterocycyl, optionally substituted aryl, or optionally substituted heteroaryl or two $R^g$ groups are joined to form a 5- to 6-membered optionally substituted heterocycyl or optionally substituted heteroaryl ring;

each instance of n is, independently, 0, 1, 2, 3, or 4;
each instance of m is, independently, 0, 1, 2, 3, or 4; and
x is 1, 2, 3, 4, 5, or 6;
$R^{xx}$ is hydrogen, a hydroxyl protecting group, or a group of Formula:

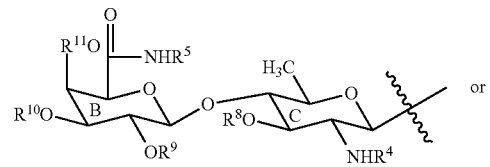

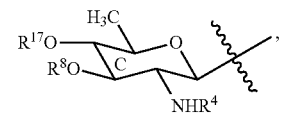

$R^{12}$ is hydrogen, a hydroxyl protecting group, or the group (D):

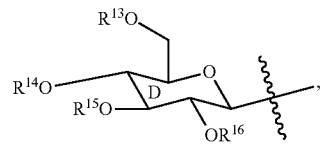

wherein $R^{13}$, $R^{14}$, $R^{15}$, $R^{16}$, and $R^{17}$ are each independently hydrogen or a hydroxyl protecting group;
$R^1$, $R^2$, $R^3$, and $R^4$ are each independently hydrogen or an amino protecting group;
$R^5$ is hydrogen, an amino protecting group, or the group (A):

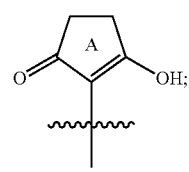

$R^6$, $R^7$, $R^8$, $R^9$, $R^{10}$, and $R^{11}$ are each independently hydrogen or a hydroxyl protecting group; and
$R^a$ and $R^b$ are each independently hydrogen or a hydroxyl protecting group.

2. The compound of claim 1 of Formula (II):

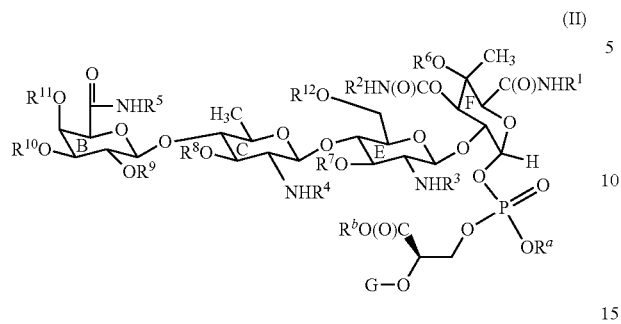

or a pharmaceutically acceptable salt, solvate, hydrate, tautomer, isomer, enantiomer, diastereomer, or polymorph thereof.

3. The compound of claim 1 of Formula (III):

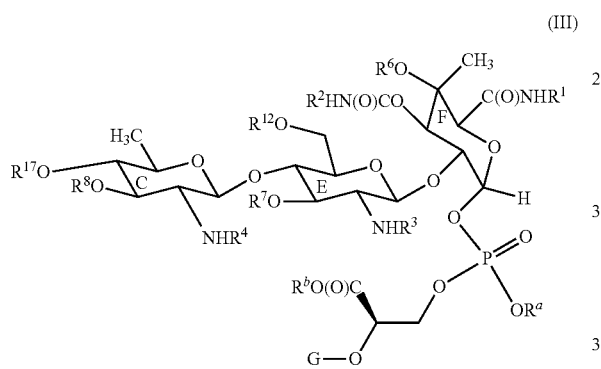

or a pharmaceutically acceptable salt, solvate, hydrate, tautomer, isomer, enantiomer, diastereomer, or polymorph thereof; wherein $R^{17}$ is hydrogen or a hydroxyl protecting group.

4. The compound of claim 1 of Formula (IV):

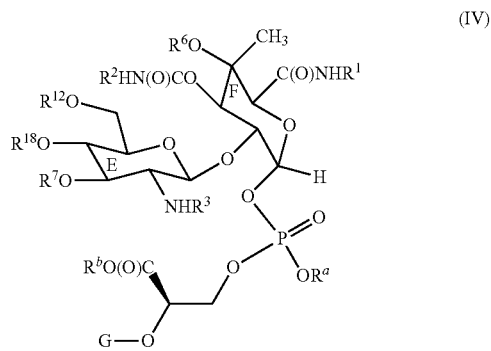

or a pharmaceutically acceptable salt, solvate, hydrate, tautomer, isomer, enantiomer, diastereomer, or polymorph thereof; wherein $R^{18}$ is hydrogen or a hydroxyl protecting group.

5. The compound of claim 1 wherein G is a group of Formula (a).

6. The compound of claim 5, wherein the group of Formula (a) is selected from the group consisting of:

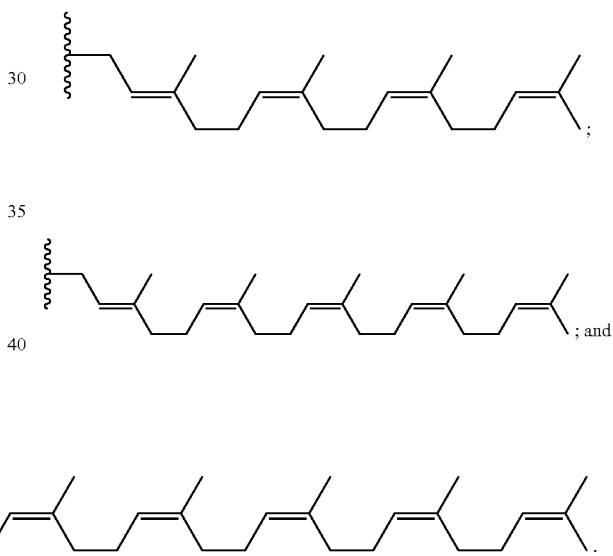

7. The compound of claim 1 wherein G is a group of Formula (b).

8. The compound of claim 7 wherein at least one of $X_1$, $X_2$, $X_3$, $X_4$, $X_5$, $X_6$, and $X_7$ is halogen.

9. The compound of claim 7 wherein $X_1$ and $X_2$ are each hydrogen, $X_3$ and $X_4$ are each fluoro, and $X_5$, $X_6$, and $X_7$ are each fluoro.

10. The compound of claim 7, wherein the group of Formula (b) is selected from the group consisting of:

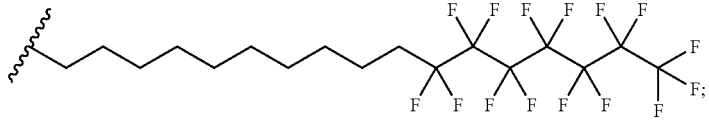 [SMILES: *CCCCCCCCCCC(F)(F)C(F)(F)C(F)(F)C(F)(F)C(F)(F)C(F)(F)C(F)(F)F]

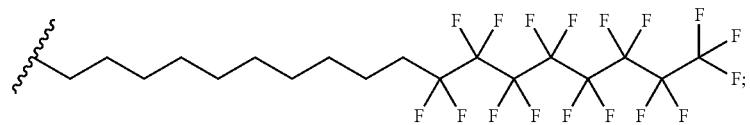 [SMILES: *CCCCCCCCCCC(F)(F)C(F)(F)C(F)(F)C(F)(F)C(F)(F)C(F)(F)C(F)(F)C(F)(F)F]
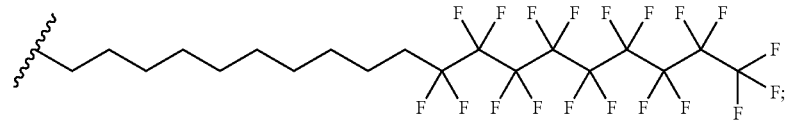 [SMILES: *CCCCCCCCCCC(F)(F)C(F)(F)C(F)(F)C(F)(F)C(F)(F)C(F)(F)C(F)(F)C(F)(F)C(F)(F)F]
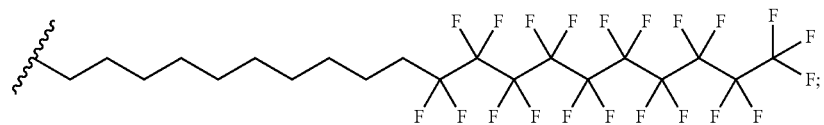 [SMILES: *CCCCCCCCCCC(F)(F)C(F)(F)C(F)(F)C(F)(F)C(F)(F)C(F)(F)C(F)(F)C(F)(F)C(F)(F)C(F)(F)F]
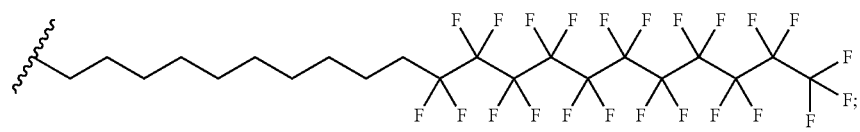 [SMILES: *CCCCCCCCCCC(F)(F)C(F)(F)C(F)(F)C(F)(F)C(F)(F)C(F)(F)C(F)(F)C(F)(F)C(F)(F)C(F)(F)C(F)(F)F]
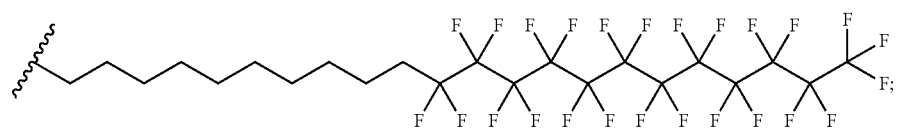 [SMILES: *CCCCCCCCCCC(F)(F)C(F)(F)C(F)(F)C(F)(F)C(F)(F)C(F)(F)C(F)(F)C(F)(F)C(F)(F)C(F)(F)C(F)(F)C(F)(F)F]
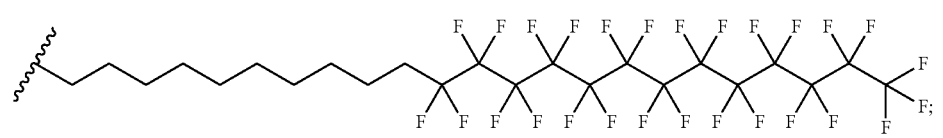 [SMILES: *CCCCCCCCCCC(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)F]
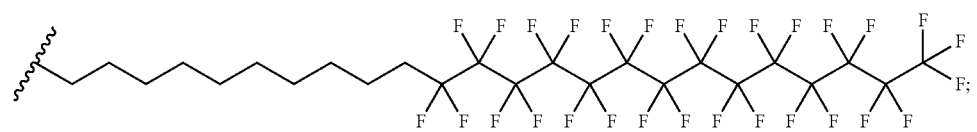 [SMILES: *CCCCCCCCCCC(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)F]

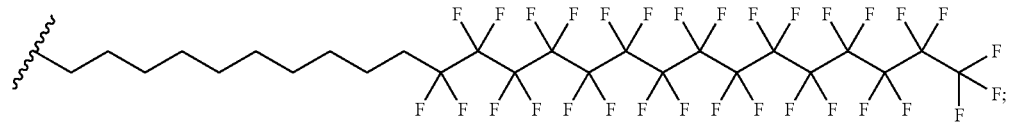 [SMILES: *CCCCCCCCCCC(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)F]
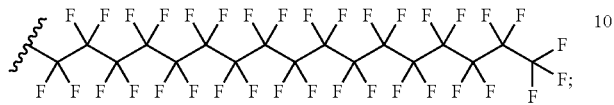
10
15
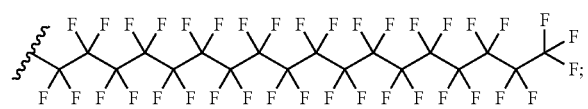
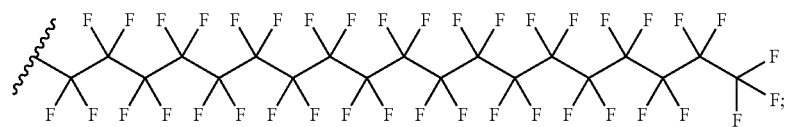 [SMILES: *C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)F]
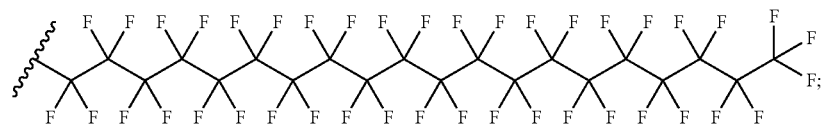 [SMILES: *C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)F]
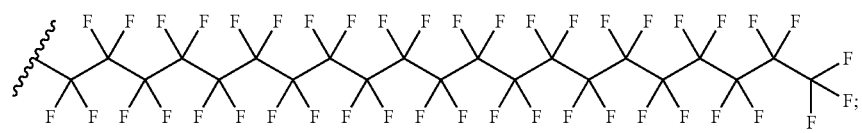 [SMILES: *C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)F]
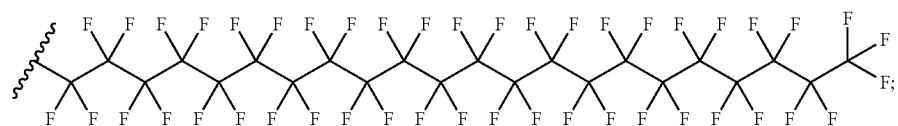 [SMILES: *C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)F]
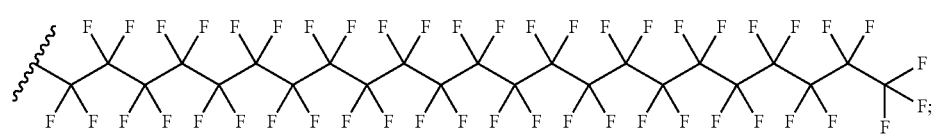 [SMILES: *C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)F]

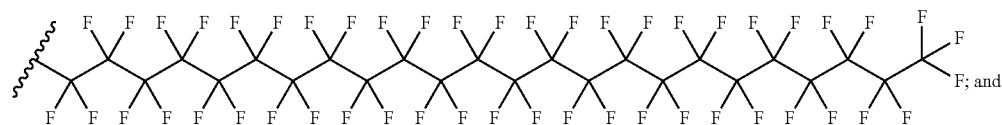
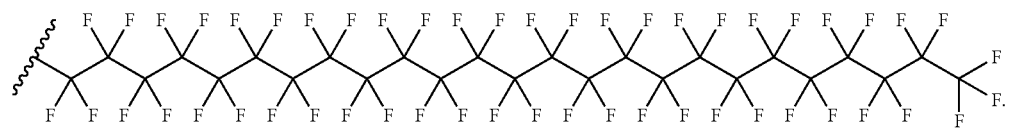 [SMILES: *C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)C(F)(F)F]
11. The compound of claim 1 wherein G is a group of Formula (c).
12. The compound of claim 11, wherein the group of Formula (c) is selected from the group consisting of:
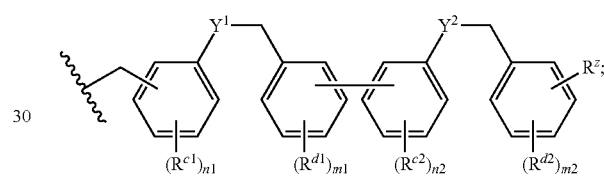
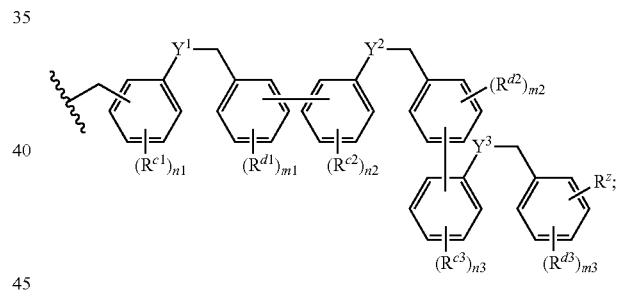
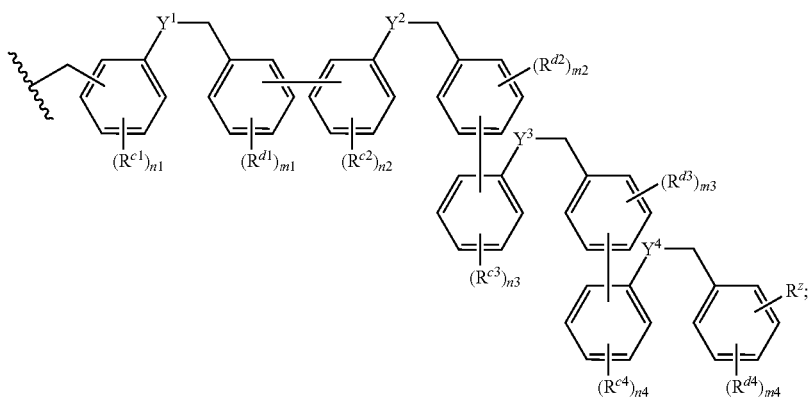

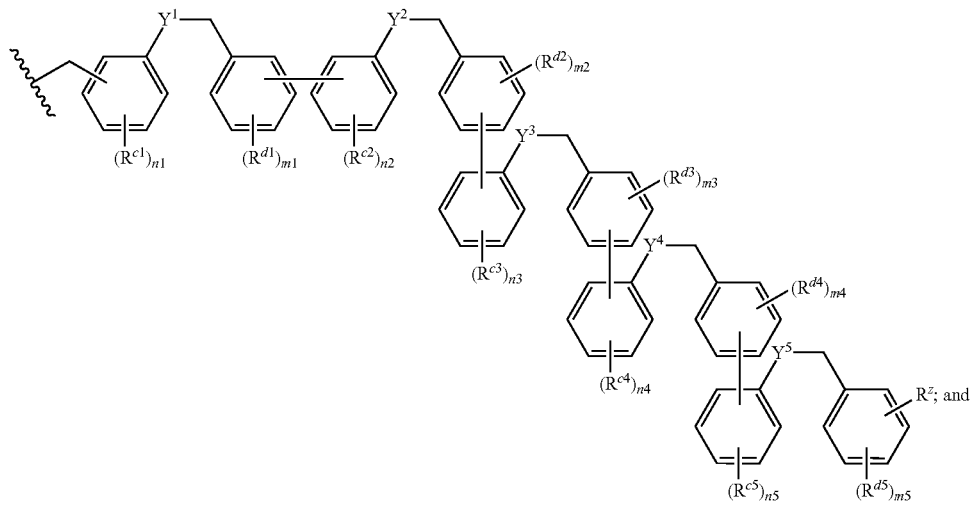

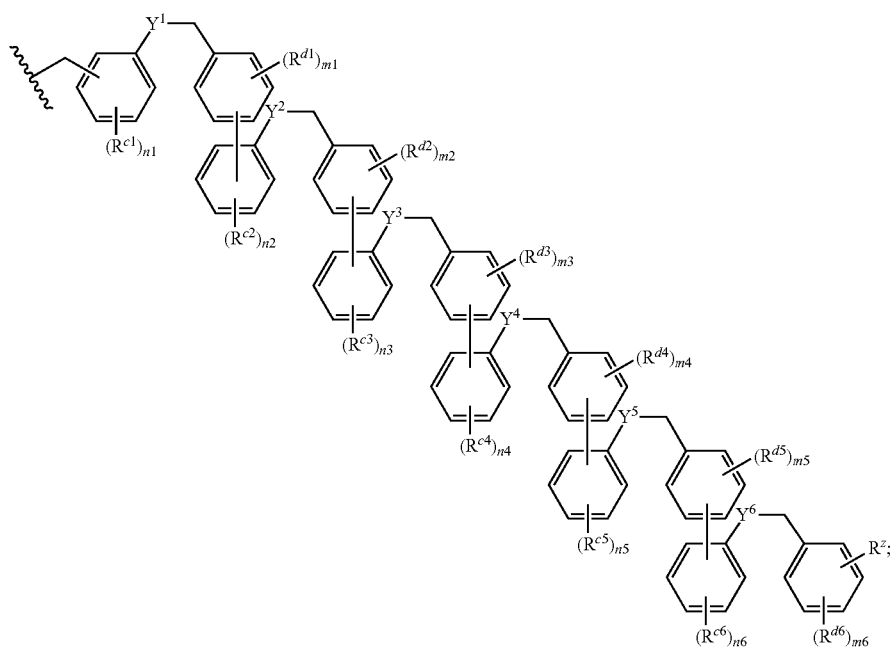

wherein:

$R^{c1}$, $R^{c2}$, $R^{c3}$, $R^{c4}$, $R^{c5}$, and $R^{c6}$, each independently —F, —Br, —I, —Cl, optionally substituted aliphatic, optionally substituted heteroaliphatic, optionally substituted carbocycyl, optionally substituted heterocycyl, optionally substituted aryl, optionally substituted heteroaryl, —$OR^e$, —$SR^e$, —$NHR^e$, or —$N(R^e)_2$, wherein each instance of $R^e$ is independently hydrogen, optionally substituted aliphatic, optionally substituted heteroaliphatic, optionally substituted carbocycyl, optionally substituted heterocycyl, optionally substituted aryl, or optionally substituted heteroaryl, or two $R^e$ groups are joined to form a 5- to 6-membered optionally substituted heterocycyl or optionally substituted heteroaryl ring;

$R^{d1}$, $R^{d2}$, $R^{d3}$, $R^{d4}$, $R^{d5}$, and $R^{d6}$, each independently —F, —Br, —I, —Cl, optionally substituted aliphatic, optionally substituted heteroaliphatic, optionally substituted carbocycyl, optionally substituted heterocycyl, optionally substituted aryl, optionally substituted heteroaryl, —$OR^f$, —$SR^f$, —$NHR^f$, or —$N(R^f)_2$, wherein each instance of $R^f$ is independently hydrogen, optionally substituted aliphatic, optionally substituted heteroaliphatic, optionally substituted carbocycyl, optionally substituted heterocycyl, optionally substituted aryl, or optionally substituted heteroaryl, or two $R^f$ groups are joined to form a 5- to 6-membered optionally substituted heterocycyl or optionally substituted heteroaryl ring;

$Y^1, Y^2, Y^3, Y^4, Y^5$, and $Y^6$, each independently corresponds to —O—, —S—, —$NR^Y$—, or an optionally substituted methylene group, wherein $R^Y$ is hydrogen, optionally substituted aliphatic, or an amino protecting group;

n1, n2, n3, n4, n5, and n6 each independently 0, 1, 2, 3, or 4; and m1, m2, m3, m4, m5, and m6 each independently 0, 1, 2, 3, or 4.

13. The compound of claim 1 wherein G is selected from the group consisting of:

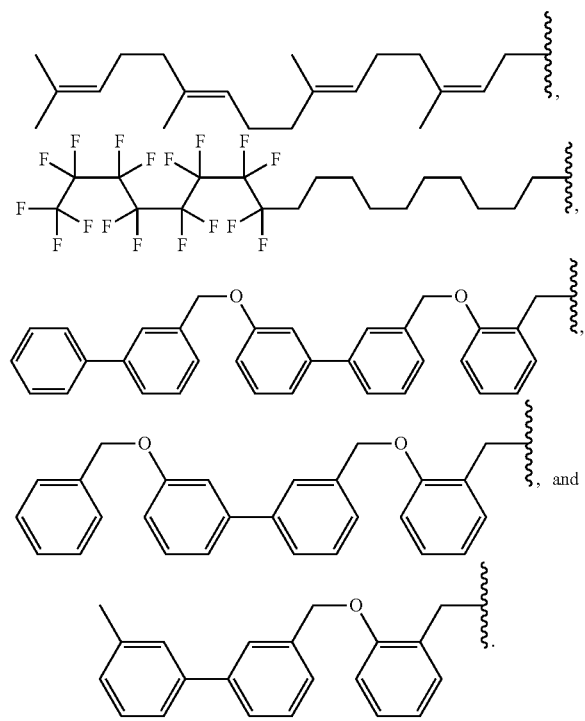

14. A pharmaceutical composition comprising an effective amount of a compound of claim 1, or a pharmaceutically acceptable salt, solvate, hydrate, tautomer, isomer, enantiomer, diastereomer, or polymorph thereof, and optionally a pharmaceutically acceptable excipient.

15. A method of treating a bacterial infection comprising administering to a subject an effective amount of a compound of claim 1, or a pharmaceutically acceptable salt, solvate, hydrate, tautomer, isomer, enantiomer, diastereomer, or polymorph thereof.

16. The method of claim 15, wherein the bacterial infection being treated is caused by Gram-positive bacteria.

17. The method of claim 15, wherein bacterial infection being treated is caused by Gram-negative bacteria.

18. The method of claim 15, wherein bacterial infection being treated is caused by vancomycin-resistant bacteria.

19. The method of claim 15, wherein bacterial infection being treated is caused by methicillin-resistant bacteria.

20. An in vitro method of inhibiting bacterial growth by contacting a bacterium with an effective amount of a compound of claim 1, or a pharmaceutically acceptable salt, solvate, hydrate, tautomer, isomer, enantiomer, diastereomer, or polymorph thereof.

21. The method of claim 15, wherein the bacterial infection being treated is caused by vancomycin-resistant *Staphylococcus aureus*, vancomycin-resistant Enterococci, or methicillin-resistant *Staphylococcus aureus*.

22. The compound of claim 1, wherein the compound is of Formula (I):

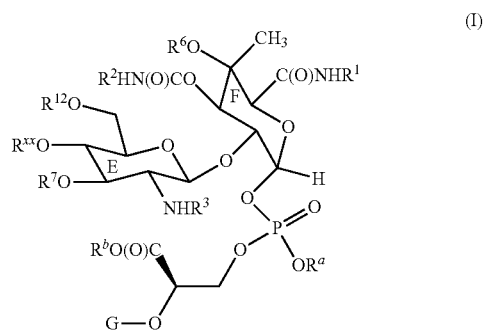

or a pharmaceutically acceptable salt.

23. A pharmaceutical composition comprising an effective amount of a compound of claim 1, or a pharmaceutically acceptable salt thereof, and optionally a pharmaceutically acceptable excipient.

24. A method of treating a bacterial infection comprising administering to a subject an effective amount of a compound of claim 1, or a pharmaceutically acceptable salt thereof.

* * * * *